(12) United States Patent
Beattie et al.

(10) Patent No.: US 7,539,579 B2
(45) Date of Patent: May 26, 2009

(54) OLIGONUCLEOTIDE PROBES FOR GENOSENSOR CHIPS

(76) Inventors: Kenneth L. Beattie, 1326 Open Range Rd., Crossville, TN (US) 38555; Mitchel J. Doktycz, 1405 Rush Limbaugh La., Knoxville, TN (US) 37932; Alfonso Mendez-Tenorio, Sur 127 No 2316 Col. Gabriel Ramos Millan, 08720 Mexico City (MX); Rogelio Maldonado-Rodriguez, Cda, Merced de las Huertas No. 28, Col. Nextitla, 11420, Mexico City (MX); Armando Guerra-Trejo, Nilo 180 Col Claveria, 02080, Mexico City (MX)

( * ) Notice: Subject to any disclaimer, the term of this patent is extended or adjusted under 35 U.S.C. 154(b) by 117 days.

(21) Appl. No.: 10/410,040

(22) Filed: Apr. 9, 2003

(65) Prior Publication Data

US 2004/0111221 A1 Jun. 10, 2004

Related U.S. Application Data

(60) Provisional application No. 60/371,113, filed on Apr. 9, 2002, now abandoned.

(51) Int. Cl.
*G06F 19/00* (2006.01)
*C12Q 1/68* (2006.01)
(52) U.S. Cl. ............................................ 702/19; 435/6
(58) Field of Classification Search .................. None
See application file for complete search history.

(56) References Cited

OTHER PUBLICATIONS

Li et al. (Bioinformatics (2001) vol. 17, pp. 1067-1076).*
Mitsuhashi, M. et al. Oligonucleotide Probe Design a new approach: *Nature*, Feb. 24, 1994, vol. 367, pp. 759-761.
Plasterer, T. et al. Primer and Probe: *Humana Press*, 1984, vol. 70, pp. 291-302.
Schütz, E. et al. Spreadsheet Software for Thermodynamic Melting Point Prediction of Oligonucleotide Hybridization with and without Mismatches: *BioTechniques*, Dec. 1999, vol. 27, No. 6, pp. 1218-1224.
Hyndman, D. et al. Software to Determine Optimal Oligonucleotide Sequences Based on Hybridization Simulation Date: *BioTechniques*, Jun. 1996, vol. 20, No. 6, pp. 1090-1097.

* cited by examiner

*Primary Examiner*—Lori A Clow
(74) *Attorney, Agent, or Firm*—Benjamin Aaron Adler

(57) ABSTRACT

Software for designing optimized sets of oligonucleotide probes for use in genosensors (oligonucleotide microarrays) is disclosed. The selection of probe sequences is based on multiple criteria including thermal stability of the probe-target pairs, similarity degree of the probes with respect to other DNA sequences, and evaluation of the secondary structure of target molecules. The programs were written in the programming language Borland Delphi by means of Object-Oriented Programming (OOP) techniques. The Genosensor Probe Design computer program disclosed herein facilitates the design of optimized arrays of probes which accurately represents the characteristics of the nucleic acid molecule under study, such as its identity or its differences in sequence or abundance with respect to other molecules.

8 Claims, 28 Drawing Sheets

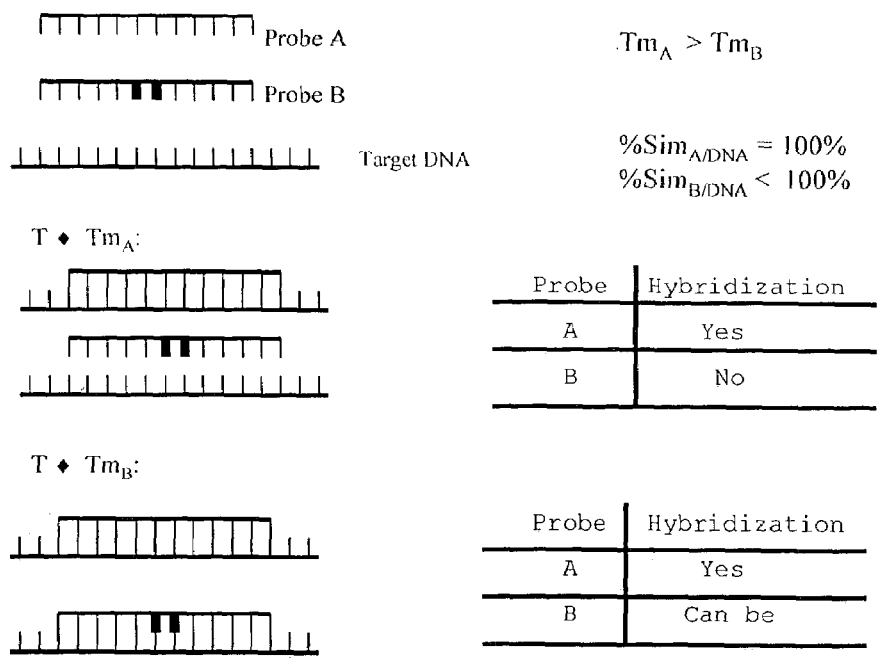
Fig. 4
Sequence specific probes
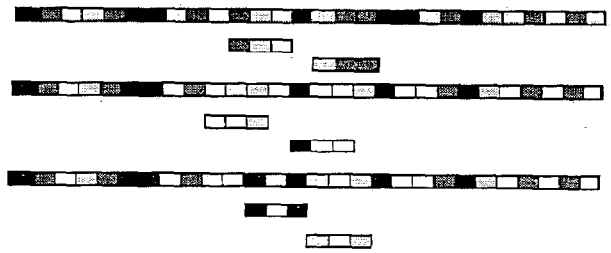
Universal primers/probes
Fig. 5

Example:

$M\_$ 5'-ACGTCGCTTGC-3'
         |||  ||||
$N\_$ 3'-TGCTCCGTACA-5'

Matching patterns and positions for each of the nearest-neighbors in the duplex.

| Step: | 1 | 2 | 3 | 4 | 5 | 6 | 7 | 8 | 9 | 10 |
|---|---|---|---|---|---|---|---|---|---|---|
| M | 11 | 10 | 9 | 8 | 7 | 6 | 5 | 4 | 3 | 2 |
| N | 1 | 2 | 3 | 4 | 5 | 6 | 7 | 8 | 9 | 10 |
| ParM (5'-3') | AC | CG | GT | TC | CG | GC | CT | TT | TG | GC |
| ParN (3'-5') | TG | GC | CT | TC | CC | CG | GT | TA | AC | CA |
| m = Len-1 | false | false | false | false | false | false | false | false | false | true |
| m = 1 | true | true | true | false | false | false | false | false | false | false |
| match1 | true | true | true | false | true | true | true | false | true | false |
| match2 | true | true | false | false | false | true | false | true | true | false |
| structure | Perfect | Perfect | SingMis | DoubInt | SingMis | Perfect | SingMis | SingMis | Perfect | EndMis3 |

Decision table

| m = Len-1 | m = 1 | match1 | match2 | Structure | $\Delta G°$ |
|---|---|---|---|---|---|
| false | true | false | true | EndMis5 | 0 |
| true | false | true | false | EndMis3 | 0 |
| false | false | false | false | DoubInt | TableNN |
| false | false | false | false | DoubEx3 | 0 |
| false | false | false | false | DoubEx5 | 0 |
| false | true | true | true | Perfect | TableNN |
| false | false | true | true | Perfect | TableNN |
| true | false | true | true | Perfect | TableNN |
| false | true | false | true | PenSing3 | TableNN |
| true | false | false | false | PenSing5 | TableNN |
| false | false | true | false | SingMis | TableNN |
| false | false | false | true | SingMis | TableNN |

```
5' -AGTGAGCTCATT-3'
    | ||||||||| |
3' -TTACTCGAGTGA-5'
```

```
5' -A              T-3'
     GTGAGCTCAT
     ||||||||
     TACTCGAGTG
3' -T              A-5'
```

(2)

```
                                       *              20              *              40              *              60              *              80
P_aeruginosa   : CTCCTACGGGAGGCAGCAGTGGGGAATATTGGACAATGGGCGCAAGCCTGATCCAGCCATGCCGCGTGTGTGAAGAAGGTCTTCG :  85
P_alcaligenes  : CTCCTACGGGAGGCAGCAGTGGGGAATATTGCACAATGGGCGAAAGCCTGATCCAGCCATGCCGCGTGTGTGAAGAAGGTCTTCG :  85
P_fluorescens  : CNCCTACGGNNGGCAGCAGCAGTGGGGAATATTGGACAATGGGCGAAAGCCTGATCCAGCCATGCCGCGTGTGTGAAGAAGCTCTTCG :  85
P_putida       : CTCCTACGGGAGGCAGCAGTGGGGAATATTGGACAATGGGCGAAAGCCTGATCCAGCCATGCCGCGTGTGTTAAGAAGGTCTTCG :  85
P_veronii      : CTCCTACGGGAGGCAGCAGTGGGGAATATTGGACAATGGGCGAAAGCCTGATCCAGCCATGCCGCGTGTGTCTCAAGAAGGTCTTCG :  85
P_syringae     : CTCCTACGGGAGGCAGCAGTGGGGAATATTGGACAATGGGCGAAAGCCTGATCCAGCCATGCCGCGTGTGTGAAGAAGGTCTTCG :  85
S_maltophilia  : CTCCTACGGGAGGCAGCAGTGGGGAATATTGGACAAGGGGCGCAAGCCTGATCCAGCCATACGGCGTGGGTGAGTGAGTTTTCG :  84
B_pumilus      : CTCCTACGGGAGGCAGCAGTAGGGGAATCTTCCGCAATGGACGAAAGTCTGACGGAGCAACGCCGCGTGAGTGATGAAGGTTTTCG :  85
Bacillus_sp    : CTCCTACGGGAGGCAGCAGTAGGGGAATCTTCCGCAATGGACGAAAGTCTGACGGAGCAACGCCGCGTGAGTGATGAAGGTTTTCG :  85
1                                                                    AAGTCTGAC
2                                                                    AGTCTGACG
3                                                                          GGAGCAACG
4                                                                                 GTGAGTGAT
5                                                                                 TGAGTGATG
6                                                                                         GGAGAAG-CC
```

```
                        180                    *
P_aeruginosa  : AACTTCGTGCTGCCAGCAGCCCGCGGGTAATAC : 197  (SEQ ID NO.6)
P_alcaligenes : AACTCTGTGTGCCAGCAGCCCGCGGTAATAC   : 198  (SEQ ID NO.7)
P_fluorescens : AACTCTGTGTGCCAGCAGCCCGCGGTAATAC   : 198  (SEQ ID NO.8)
P_putida      : AACTCTGTGTGCCAGCAGCCCGCGGTAATAC   : 198  (SEQ ID NO.9)
P_veronii     : AACTCTGTGTGCCAGCAGCCCGCGGTAATAC   : 198  (SEQ ID NO.10)
P_syringae    : AACTCTGTGTGCCAGCAGCCCGCGGTAATAC   : 198  (SEQ ID NO.11)
S_maltophilia : AACTTCGTGTGCCAGCAGCCCGCGGTAATAC   : 197  (SEQ ID NO.12)
B_pumilus     : AACTACGTGCCAGCAGCCGCCGGTAATAC     : 198  (SEQ ID NO.13)
Bacillus_sp   : AACTACGTGCCAGCAGCCGCCGGTAATAC     : 198  (SEQ ID NO.14)
```

Fig. 12C

```
                        *         20         *         40         *         60         *         80         *
P_fluorescens  : CCAGCAGCCGCGGTAATACAGAGGGTGCAAGCGTTAATCGGAATTACTGGGCGTAAAGCGCGCGTAGGTGGTTTGTTAAGTTGGATGTGA :  90
P_veronii      : CCAGCAGCCGCGGTAATACAGAGGGTGCAAGCGTTAATCGGAATTACTGGGCGTAAAGCGCGCGTAGGTGGTTAGTTAAGTTGGATGTGA :  90
P_syringae     : CCAGCAGCCGCGGTAATACAGAGGGTGCAAGCGTTAATCGGAATTACTGGGCGTAAAGCGCGCGTAGGTGGTCGTTGTTAAGTTGGATGTGA :  90
P_putida       : CCAGCAGCCGCGGTAATACAGAGGGTGCAAGCGTTAATCGGAATTACTGGGCGTAAAGCGCGCGTAGGTGGTTGTTAAGTTGGATGTGA :  90
P_aeruginosa   : CCAGCAGCCGCGGTAATACGAAGGGTGCAAGCGTTAATCGGAATTACTGGGCGTAAAGCGCGCGTAAGTGGTTCAGCAAGTTGGATGTGA :  90
P_alcaligenes  : CCAGCAGCCGCGGTAATACAGAGGGTGCAAGCGTTAATCGGAATTACTGGGCGTAAAGCGCGCGTAGGTGGTTTATTAAGTCGGATGTGA :  90
S_maltophilia  : CCAGCAGCCGCGGTAATACGGAGGGTGCAAGCGTTACTCGGAATTATTGGGCGTAAAGCGTGCGTAGGCGGTCGTTATTTAAGTCCGTTGTGA :  90
B_pumilus      : CCAGCAGCCGCGGTAATACGTAGGTGGCAAGCGTTGTCCGGAATTATTGGGCGTAAAGGGCTCGCAGGCGGTTTCTTAAGTCTGATGTGA :  90
Bacillus_sp    : CCAGCAGCCGCGGTAATACGTAGGTGGCAAGCGTTGTCCGGAATTATTGGGCGTAAAGCGCGCGCAGGCGGTCTCTTAAGTCTGATGTGA :  90
29             :                                                                                 GTGGTTCAG
30             :                                                                                 TGGTTCAGC
31             :                                                                                 GGTTCAGCA
32             :                                                                                 GTTCAGCAA
33             :                                                                                 TTCAGCAAG
34             :                                                                                AGCAAGCTT
35             :                                                                                ACCAAGTTG
36             :                                                                                GCAAGCTTG
37             :                                                                                GCAAGTTGG
38             :                                                                                CAAGCTTGA
39             :                                                                               AAGCTTGAT
40             :                                                                               AAGTCCGTT
41             :                                                                               AAGTCTCAT
42             :                                                                               AGCTTGATG
43             :                                                                               AGTCCGTTG
44             :                                                                               AGTCTGATC
45             :                                                                              GCTTGATGT
46             :                                                                              GTCCGTTGT
47             :                                                                              GTCTGATGT
48             :                                                                             CTTCATGTC
49             :                                                                             TCCGTTGTG
50             :                                                                             TCTGATGTG
```

Fig. 12D

```
                    100          *          120          *          140          *          160          *          180
P_fluorescens : AATCCCCCGGGCTCAACCTGGGAACTGCATCCAAAA-CTGACTGACTAGAGTATGGTAGAGGGTGGTGGAATTTCCTGTGTAGCGGTGAAA : 179
P_veronii    : AATCCCCGGGCTCAACCTGGGAACTGCATTCAAAA-CTGACTGACTACGAGTATGGTAGAGGGTGGTGGAATTTCCTGTGTAGCGGTGAAA : 179
P_syringae   : AATCCCCGGGCTCAACCTGGGAACTGCATCCAAAA-CTGGCAAGCTAGAGTATGGTAGAGGGTGGTGGAATTTCCTGTGTAGCGGTGAAA : 179
P_putida     : AAGCCCCCGGGCTCAACCTGGGAACTGCATCCAAAA-CTGGCAAGCTAGAGACTGAGTACGGTAGAGGGTGGTGGAATTTCCTGTGTAGCGGTGAAA : 179
P_aeruginosa : AATCCCCGGGCTCAACCTGGGAACTGCATCCAAAACTGACTGAGCTAGAGTACGGTAGAGGG-TGGTAGAATTCCTGTGTAGCGGTGAAA : 179
P_alcaligenes: AATCCCTGGGCTCAACCTGGGAACTGCCTCAAAA-CTACTGAGCTAGAGTACGGTAGAGGGTAGTGGAATTCCGTGTGTAGCGGTGAAA : 179
S_maltophilia: AAGCCTGGGCTCAACCTGGGAACTGCCTCAGTGGATA-CTGGATGACTAGAATGTGGTAGAGGGTAGCGGAATTCCACGTGTAGCGGTGAAA : 179
B_pumilus    : AAGCCCCCGGCTCAACCGGGGAGGGTCAGTGGGTCATTGAAA-CTGGGAAACTTGAGTGCACAAGAGGAGAGTGGAATTCCACGTGTAGCGGTGAAA : 179
Bacillus_sp  : AAGCCCCCGGCTCAACCGGGGAGGGTCATTGGAAA-CTGGAGACTTGAGTACAGAAGAGGAGAGTGGAATTCCACGTGTAGCGGTGAAA : 179

51                                                 GTGGATA-CT
52                                                 AAGCTACTG
53                                                 AA-CTACTGA
54                                                 AA-CTGACTG
55                                                 AGCTACTGA
56                                                 A-CTACTGAG
57                                                 A-CTGACTGA
58                                                 A-CTGGCAAG
59                                                 GCTACTGAG
60                                                 CTACTGAGC
61                                                 CTGACTGAC
62                                                 CTGGCAAGC
63                                                 CTACTGAGC
64                                                 CTGACTGAC
65                                                 CTGGATGAC
66                                                 GACTGACTA
67                                                 GCAAGCTA
68                                                 ACTGACTAG
69                                                 GCAAGCTAG
70                                                 TGAAGCTAGA
71                                                 CAAGCTAGA
72                                                 CTAGAATGT
73                                                          GTAGAGG-TG
74                                                          TAGAGG-TGG
75                                                          AGAGG-TGGT
76                                                          GAGG-TGGTA
77                                                          AGG-TGGTAG
78                                                          GG-TGGTAGA
79                                                              TGGTAGAAT
```

Fig. 12E

```
                             200           *          220           *          240           *          260           *
P_fluorescens : TGCGTTGATATAGGAAGCAACACCAGTGGCGAAGGCGACCACCTGGTGAAGGAAGGCCCTGATACGAAGCCTGGGGAGCAAACAGG : 269
P_veronii     : TGGGTAGATATAGGAAGGAACACCAGTGGCGAAGGCGACCACCTGGACTGATACTGACACTGAGACTGCGAAAGCGTGGGGAGCAAACAGG : 269
P_syringae    : TGCGTAGATATAGGAAGGAACACCAGTGGCGAAGGCGACCACCTGGACTGATACTGACACTGAGACTGCGAAAGCGTGGGGAGCAAACAGG : 269
P_putida      : TGCGTACATATAGGAAGGAACACCAGTGGCGAAGGCGACCACCTGGACTGATACTGACACTGAGACTGCGAAAGCGTGGGGAGCAAACAGG : 269
P_aeruginosa  : TGCGTAGATATAGGAAGGAACACCAGTGGCGAAGGCGACCACCTGGACTG-TACTGACACTGAGACTGCGAAAGCGTGGGGAGCAAACAGG : 268
P_alcaligenes : TGCGTAGATATAGGAAGGAACACCAGTGGCGAAGGCGACCACCTGGACTGATACTGACACTGAGACTGCGAAAGCGTGGGGAGCAAACAGG : 269
S_maltophilia : TGCGTAGAGATCAGGAATGTGGAGGAACACCAATCCATGCGAAGGCGACCAGTGACTACCTGGCAGACCACCAGCCTGAGGAGCACAACAGG : 269
B_pumilus     : TGCGTAGAGATGTGGAGGAACACCAGTGGCGAAGGCGACCCTCTGTAACTGACGCTGAGGAGCGCAAGCGTGGGGAGCGAACAGG : 269
Bacillus_sp   : TGCGTAGAGATGTGGAGGAACACCAGTGGCGAAGGCGACTCCTGGTCTGTAACTGACGCTGAAGCGCGAAAGCGTGGGAGCAAACAGG : 269

80                                                         GTGGTGAAG
81                                                                   CTCTCTGGT
82                                                                   TCTCTGGTC
83                                                                   CTCTGGTCT
84                                                                        TGGACCAAC
85                                                                            ACTG-TACTG
86                                                                            ACCAACATT
87                                                                                 CTG-TACTGA
88                                                                                    CATTGACAC

280
P_fluorescens : ATTAGATACCCTGGTAGTCCACGCC  : 294  (SEQ ID NO.15)
P_veronii     : ATTAGATACCCTGGTAGTCCACGCC  : 294  (SEQ ID NO.16)
P_syringae    : ATTAGATACCCTGGTAGTCCACGCC  : 294  (SEQ ID NO.17)
P_putida      : ATTAGATACCCTGGTAGTCCACGCC  : 294  (SEQ ID NO.18)
P_aeruginosa  : ATTAGATACCCTGGTAGTCCACGCC  : 293  (SEQ ID NO.19)
P_alcaligenes : ATTAGATACCCTGGTAGTCCACGCC  : 294  (SEQ ID NO.20)
S_maltophilia : ATTAGATACCCTGGTAGTCCACGCC  : 294  (SEQ ID NO.21)
B_pumilus     : ATTAGATACCCTGGTAGTCCACGCC  : 294  (SEQ ID NO.22)
Bacillus_sp   : ATTAGATACCCTGGTAGTCCACGCC  : 294  (SEQ ID NO.23)
```

Fig. 12F

```
Calculation of thermodynamic stability for oligonucleotides

Direct sequence:    ATCTCAAGTCAGCG
Complementary:      CACTCACTAGACAT

☐ Auto-generate complementary
Secondary structure analysis:

5'-AT TCAA TCA C  -3'
3'-TA AGAT AGT A  -5'

Description:
MN/MN    H       S       G       Structure:
AT/TA   -7.20  -20.40   -0.88   Perfect paired dinucleotide
TG/AC   -8.50  -22.70   -1.45   Perfect paired dinucleotide
GT/CA   -8.40  -22.40   -1.44   Perfect paired dinucleotide
TC/AG   -8.20  -22.20   -1.30   Perfect paired dinucleotide
CA/GA   -0.90   -4.20    0.40   Single internal mismatch
AA/AT    4.70   12.90    0.70   Single internal mismatch
AG/TC   -7.80  -21.00   -1.28   Perfect paired dinucleotide
GT/CA   -8.40  -22.40   -1.44   Perfect paired dinucleotide
TC/AG   -8.20  -22.20   -1.30   Perfect paired dinucleotide
CA/GT   -8.50  -22.70   -1.45   Perfect paired dinucleotide
AG/TC   -7.80  -21.00   -1.28   Perfect paired dinucleotide
GC/CA    0.00    0.00    0.00   5' Terminal mismatch
CG/GC    0.00    0.00    0.00   Pendulous single mismatch close to 3' end ΔH = -59.30 kcal/mol
ΔS = -166.30 cal/mol K
ΔG = -10.72 kcal/mol
```

Fig. 18

| position | Stacking | Gstk | Tmstk | junction | Gjunction | capture | Gcap | Tmcap |
|---|---|---|---|---|---|---|---|---|
| 1660 | CCTACAACCACAAATCTACCCGCTG | -33.510 | 66.7 | CCTGGAGA | -10.690 | GAGACCA | -8.610 | 17.5 |
| 1663 | GCACCTACAACCACAAATCTACCCG | -33.670 | 66.9 | CCCGCTGG | -12.660 | CTGGAGA | -8.450 | 16.3 |
| 1664 | AGCACCTACAACCACAAATCTACCC | -32.780 | 65.9 | ACCCGCTG | -12.260 | GCTGGAG | -9.390 | 23.2 |
| 1665 | AAGCACCTACAACCACAAATCTACC | -31.940 | 64.4 | TACCCGCT | -11.390 | CGCTGGA | -10.280 | 28.1 |
| 1666 | AAAGCACCTACAACCACAAATCTAC | -31.100 | 62.9 | CTACCCGC | -11.390 | CCGCTGG | -10.820 | 31.6 |
| 1677 | TTGGACCCACTAAAGCACCTACAAC | -32.900 | 66.1 | CAACCACA | -10.070 | CACAAAT | -7.220 | 9.3 |
| 1684 | CGCATGTTTGGACCCACTAAAGCAC | -34.500 | 68.0 | GCACCTAC | -10.270 | CTACAAC | -7.190 | 10.6 |
| 1687 | CTACGCATGTTTGGACCCACTAAAG | -32.670 | 65.2 | AAAGCACC | -10.250 | CACCTAC | -8.030 | 15.1 |
| 1695 | GGTCTGATCTACGCATGTTTGGACC | -33.590 | 66.7 | GACCCACT | -10.590 | CACTAAA | -6.750 | 6.4 |
| 1696 | AGGTCTGATCTACGCATGTTTGGAC | -33.030 | 66.0 | GGACCCAC | -11.150 | CCACTAA | -7.590 | 11.0 |
| 1699 | TGTAGGTCTGATCTACGCATGTTTG | -31.920 | 64.0 | TTTGGACC | -9.870 | GACCCAC | -9.310 | 22.7 |
| 1707 | CGTAAAATTGTAGGTCTGATCTACG | -30.080 | 60.6 | TACGCATG | -10.210 | CATGTTT | -7.220 | 9.3 |
| 1708 | TCGTAAAATTGTAGGTCTGATCTAC | -29.210 | 59.5 | CTACCCAT | -10.040 | GCATGTT | -8.460 | 17.0 |
| 1747 | TTATTGTCATTAATATTCTTTTCAC | -25.670 | 53.5 | TCACCTGG | -10.600 | CTGGATA | -7.330 | 8.9 |
| 1783 | GGATGAGCAACATCTTTCAAAGAAG | -30.700 | 62.0 | CAAGCTGA | -9.850 | CTGAAAC | -7.470 | 12.4 |
| 1801 | GTAGCCGCAGAGTAGGTAGGATGAG | -33.590 | 66.9 | TGAGCAAC | -10.160 | CAACATC | -7.520 | 12.5 |
| 1819 | CGATCCCAAGTGATATTAGTAGCCG | -31.670 | 63.7 | GCCGCAGA | -12.520 | CAGAGTA | -7.330 | 9.7 |
| 1820 | TCCATCCCAAGTGATATTAGTAGCC | -30.950 | 62.9 | AGCCGCAG | -12.500 | GCAGAGT | -8.990 | 20.2 |
| 1821 | ATCCATCCCAAGTGATATTAGTAGC | -29.990 | 61.2 | TAGCCGCA | -11.800 | CGCAGAG | -9.720 | 25.7 |
| 1822 | GATCCATCCCAAGTGATATTAGTAG | -29.050 | 59.5 | CTAGCCGC | -11.790 | CCGCAGA | -10.280 | 28.1 |
| 1862 | GTGTTTCAAAGAACTTGACCATGCG | -32.600 | 64.8 | TGCCGTAA | -10.720 | GTAACGT | -8.070 | 15.3 |
| 1863 | TGTGTTTCAAAGAACTTGACCATGC | -31.880 | 64.0 | ATGCGGTA | -10.600 | GGTAACG | -8.470 | 18.3 |
| 1864 | TTGTGTTTCAAAGAACTTGACCATG | -30.640 | 62.0 | CATGCGGT | -11.470 | CGGTAAC | -8.470 | 18.3 |
| 1868 | CACCTTGTGTTTCAAAGAACTTGAC | -31.030 | 62.5 | TGACCATG | -9.810 | CATGCGG | -10.030 | 27.2 |
| 1890 | TGAAAATTTTGTAACCATGCTCCAC | -30.710 | 62.1 | CCACCTTG | -10.300 | CTTGTGT | -8.060 | 14.6 |
| 1893 | TATTGAAAATTTTGTAACCATGCTC | -28.440 | 58.2 | GCTCCACC | -11.390 | CACCTTG | -8.460 | 17.8 |
| 1896 | CAATATTGAAAATTTTGTAACCATC | -26.950 | 55.6 | CATCCTCC | -10.440 | CTCCACC | -9.150 | 21.6 |

Fig. 25

OLIGONUCLEOTIDE PROBES FOR GENOSENSOR CHIPS

CROSS-REFERENCE TO RELATED APPLICATION

This non-provisional patent application claims benefit of provisional patent application U.S. Ser. No. 60/371,113, filed Apr. 9, 2002, now abandoned.

COMPUTER PROGRAM LISTING APPENDIX

Computer program listings are submitted on compact disc in compliance with 37 C.F.R. §1.96, and are incorporated by reference herein. A total of 2 compact discs (including duplicates) are submitted herein. The files on each compact disc are listed below:

| Folder | Files | Size (KB) | Date Created |
|---|---|---|---|
| | Script.doc | 48 | Apr. 9, 2003 |
| AdjustLen | About.dfm | 4 | Feb. 3, 2000 |
| | About.pas | 4 | Feb. 3, 2000 |
| | Adjust.cfg | 4 | Feb. 3, 2000 |
| | Adjust.dof | 4 | Feb. 3, 2000 |
| | Adjust.dpr | 4 | Feb. 3, 2000 |
| | Adjust.txt | 4 | Feb. 5, 2000 |
| | Analysis.pas | 8 | Feb. 5, 2000 |
| | Ddmodel.dat | 4 | Aug. 26, 1998 |
| | MainForm.dfm | 4 | Feb. 5, 2000 |
| | MainForm.pas | 8 | Feb. 5, 2000 |
| AlnClust | AlnClust.dpr | 4 | May 2, 2001 |
| | Calculate.pas | 12 | Jul. 23, 1999 |
| | Methods.dfm | 4 | Sep. 13, 1999 |
| | Methods.pas | 4 | Jul. 23, 1999 |
| | ParDlg.dfm | 4 | Jul. 23, 1999 |
| | ParDlg.pas | 4 | Jul. 23, 1999 |
| BuiltDB | Build.dpr | 4 | Feb. 15, 2002 |
| | BuiltDB.dfm | 4 | Mar. 31, 2002 |
| | BuiltDB.pas | 8 | Mar. 31, 2002 |
| | ListBx.dfm | 4 | Mar. 31, 2002 |
| | ListBx.pas | 4 | Mar. 31, 2002 |
| Data | Criteria.dat | 4 | Nov. 21, 2002 |
| | Criteriaval.dat | 4 | Nov. 21, 2002 |
| | Ddmodel.dat | 4 | Aug. 26, 1998 |
| | DDOtraLucia.dat | 4 | Feb. 16, 1999 |
| | DDSantaLucia.dat | 4 | Sep. 9, 1998 |
| | DDunified.dat | 4 | Aug. 3, 1999 |
| | Doktycz.dat | 4 | Jun. 30, 1998 |
| | InitialVal.dat | 4 | Aug. 3, 1999 |
| | Nndata.dat | 4 | Aug. 3, 1999 |
| | Prueba.dat | 4 | Feb. 16, 1999 |
| | Similar.dat | 4 | Feb. 22, 2003 |
| | SSDoktycz.dat | 4 | Jun. 30, 1998 |
| | VH.dat | 4 | Feb. 27, 2003 |
| Dialog boxes | AboutBx.dfm | 28 | Feb. 27, 2003 |
| | AboutBx.pas | 4 | Aug. 14, 1999 |
| | Aboutold.dfm | 4 | Aug. 3, 1999 |
| | Aboutold.pas | 4 | Aug. 14, 1999 |
| | AddOligoDlg.dfm | 4 | Feb. 25, 2003 |
| | AddOligoDlg.pas | 4 | Feb. 25, 2003 |
| | AddProbe.dfm | 4 | Feb. 25, 2003 |
| | AddProbe.pas | 8 | Feb. 25, 2003 |
| | BegFrm.dfm | 4 | Aug. 3, 1999 |
| | BegFrm.pas | 4 | Aug. 3, 1999 |
| | CirProDlg.dfm | 4 | Feb. 12, 2003 |
| | CirProDlg.pas | 4 | Feb. 12, 2003 |
| | CritDlg.dfm | 4 | Feb. 12, 2003 |
| | CritDlg.pas | 4 | Feb. 24, 2003 |
| | DefCrit.dfm | 4 | Nov. 22, 2002 |
| | DefCrit.pas | 4 | Feb. 12, 2003 |
| | Destiny.dfm | 4 | Feb. 25, 2003 |
| | Destiny.pas | 4 | Feb. 25, 2003 |
| | DoubDlg.dfm | 4 | Aug. 3, 1999 |
| | DoubDlg.pas | 20 | Aug. 3, 1999 |
| | FieldsDlg.dfm | 4 | Feb. 9, 2003 |
| | FieldsDlg.pas | 4 | Feb. 9, 2003 |
| | GotoDl.dfm | 4 | Aug. 3, 1999 |
| | GotoDl.pas | 4 | Aug. 3, 1999 |
| | Import.dfm | 4 | Feb. 25, 2003 |
| | Import.pas | 8 | Feb. 27, 2003 |
| | InfoDNA.dfm | 8 | Aug. 3, 1999 |
| | InfoDNA.pas | 16 | Aug. 3, 1999 |
| | OlgDlg.dfm | 8 | Feb. 25, 2003 |
| | OlgDlg.pas | 16 | Feb. 27, 2003 |

-continued

| Folder | Files | Size (KB) | Date Created |
|---|---|---|---|
| | Params.dfm | 4 | Feb. 25, 2003 |
| | Params.pas | 8 | Feb. 25, 2003 |
| | Paramsold.dfm | 4 | Nov. 23, 2002 |
| | Paramsold.pas | 4 | Nov. 23, 2002 |
| | PCRdlg.dfm | 4 | Aug. 3, 1999 |
| | PCRdlg.pas | 4 | Feb. 6, 2003 |
| | Projdlg.dfm | 4 | Feb. 27, 2003 |
| | Projdlg.pas | 8 | Feb. 27, 2003 |
| | SearchB.dfm | 4 | Aug. 3, 1999 |
| | SearchB.pas | 4 | Aug. 3, 1999 |
| | SelApp.dfm | 4 | Feb. 22, 2003 |
| | SelApp.pas | 4 | Feb. 22, 2003 |
| | SimilDlg.dfm | 4 | Feb. 21, 2003 |
| | SimilDlg.pas | 8 | Feb. 21, 2003 |
| | SimResDlg.dfm | 4 | 3, 31, 2002 |
| | SimResDlg.pas | 4 | Mar. 31, 2002 |
| | SingDlg.dfm | 4 | Aug. 3, 1999 |
| | SingDlg.pas | 8 | Aug. 3, 1999 |
| | TablesDlg.dfm | 4 | Feb. 9, 2003 |
| | TablesDlg.pas | 4 | Feb. 7, 2003 |
| | VHCONF.dfm | 4 | Feb. 27, 2003 |
| | VHCONF.pas | 4 | Feb. 27, 2003 |
| GenBank | AboutGB.dfm | 20 | Aug. 13, 1999 |
| | AboutGB.pas | 4 | Aug. 13, 1999 |
| | AnalysisGB.pas | 8 | Feb. 17, 2002 |
| | Converter.cfg | 4 | Feb. 15, 2002 |
| | Converter.dof | 4 | Feb. 15, 2002 |
| | Converter.dpr | 4 | Feb. 15, 2002 |
| | Genbank.dpr | 8 | Aug. 12, 1999 |
| | Genbank.pas | 4 | Aug. Nov. 1999 |
| | Genbank.zip | 36 | Apr. 7, 2003 |
| | Main.dfm | 4 | Feb. 18, 2002 |
| | Main.pas | 4 | Feb. 17, 2002 |
| | Working.dfm | 4 | Feb. 15, 2002 |
| | Working.pas | 4 | Feb. 15, 2002 |
| Help | Genosensor.cnt | 4 | Aug. 3, 1999 |
| | Genosensor.gid | 12 | Dec. 6, 20002 |
| | Genosensor.hlp | 128 | Aug. 3, 1999 |

-continued

| Folder | Files | Size (KB) | Date Created |
|---|---|---|---|
| | Genosensor.hpj | 4 | Aug. 3, 1999 |
| | Genosensor.rtf | 8 | Aug. 3, 1999 |
| | Genosensor.sh3 | 12 | Mar. 16, 2000 |
| | Genosensor.sn3 | 8 | Aug. 27, 1999 |
| | GPDHelp.cnt | 4 | Aug. 16, 1999 |
| | GPDHelp.gid | 12 | Dec. 6, 2002 |
| | GPDHelp.hhc | 4 | Aug. 14, 1999 |
| | GPDHelp.hhk | 4 | Aug. 14, 1999 |
| | GPDHelp.hhp | 4 | Aug. 14, 1999 |
| | GPDHelp.hlp | 88 | Aug. 16, 1999 |
| | GPDHelp.hpj | 4 | Aug. 16, 1999 |
| | GPDHelp.log | 4 | Aug. 16, 1999 |
| | GPDHelp.rtf | 8 | Aug. 16, 1999 |
| | GPDHelp.sh3 | 12 | Aug. 14, 1999 |
| | SH000000.shg | 68 | Aug. 14, 1999 |
| | SH000001.shg | 52 | Aug. 14, 1999 |
| | VHhelp.cnt | 4 | Aug. 18, 1999 |
| | VHhelp.gid | 12 | Mar. 11, 2002 |
| | VHhelp.hlp | 160 | Aug. 18, 1999 |
| | VHhelp.hpj | 4 | Aug. 18, 1999 |
| | VHhelp.log | 4 | Aug. 18, 1999 |
| | VHhelp.rtf | 32 | Aug. 18, 1999 |
| | VHhelp.sh3 | 132 | Aug. 16, 1999 |
| Libraries | Combin.pas | 8 | Apr. 3, 2002 |
| | Combinar.dpr | 4 | Sep. 29, 2001 |
| | DNAclass.pas | 20 | Feb. 27, 2003 |
| | DNAoligo.pas | 24 | Feb. 27, 2003 |
| | Formats.pas | 12 | Feb. 20, 2003 |
| | Graph2D.pas | 12 | Sep. 18, 2001 |
| | Indicar.dfm | 4 | Nov. 17, 2002 |
| | Indicar.pas | 4 | Nov. 17, 2002 |
| | OlgClass.old | 36 | Aug. 3, 1999 |
| | OlgClass.pas | 44 | Nov. 21, 2002 |
| | OlgClass2.old | 40 | Aug. 3, 1999 |
| | OOPlist.pas | 8 | Aug. 3, 1999 |
| | RichFmt.pas | 12 | Mar. 10, 2002 |
| | Rtfcolor.pas | 4 | Aug. 3, 1999 |
| | Tools.pas | 8 | Apr. 2, 2002 |

-continued

| Folder | Files | Size (KB) | Date Created |
|---|---|---|---|
| | VH.pas | 4 | Feb. 17, 2002 |
| | VHclass.pas | 8 | Feb. 17, 2002 |
| MapSeq | AnsiStr.pas | 16 | Sep. 30, 1998 |
| | Codific.dpr | 4 | Oct. 9, 1998 |
| | Codigo.pas | 8 | Oct. 2, 1998 |
| | Combina2.pas | 8 | Sep. 30, 1998 |
| | MapSeq.dpr | 8 | Mar. 29, 2002 |
| | MiniStr.pas | 16 | Nov. 30, 1998 |
| | Prueba.seq | 20 | Sep. 30, 1998 |
| | Test.seq | 4 | Nov. 30, 1998 |
| | TestDNA.seq | 4 | Sep. 29, 1998 |
| | Tools.pas | 4 | Sep. 29, 1998 |
| ProbesHom | AnalysisPH.pas | 4 | Apr. 5, 2001 |
| | Calculate.~pa | 4 | Sep. 5, 1999 |
| | Calculte.dfm | 4 | May 1, 2001 |
| | Calculate.pas | 8 | Apr. 5, 2001 |
| | DDmodel.dat | 4 | Aug. 26, 1998 |
| | OligosHepC.~tx | 4 | Sep. 5, 1999 |
| | OligosHepC2.~tx | 4 | Sep. 6, 1999 |
| | Options.dfm | 4 | Apr. 5, 2001 |
| | Options.pas | 4 | Apr. 5, 2001 |
| | ProbesHom.~dp | 4 | Jul. 27, 1999 |
| | ProbesHom.cfg | 4 | Apr. 5, 2001 |
| | ProbesHom.dof | 4 | Apr. 5, 2001 |
| | ProbesHom.dpr | 4 | Apr. 5, 2001 |
| | ProbesHom.res | 4 | Jul. 23, 1999 |
| | Results.tmp | 4 | Apr. 5, 2001 |
| | SectionD.dpr | 4 | May 19, 1999 |
| Project | DBDNAWin.dfm | 4 | Feb. 21, 2003 |
| | DBDNAWin.pas | 8 | Feb. 23, 2003 |
| | EdDNA.dfm | 8 | Aug. 14, 2002 |
| | EdDNA.pas | 16 | Feb. 21, 2003 |
| | Genosensor.dpr | 4 | Feb. 27, 2003 |
| | Genosensor.ini | 4 | Feb. 27, 2003 |
| | Homol.pas | 8 | Aug. 3, 1999 |
| | Main.dfm | 68 | Mar. 1, 2003 |
| | Main.pas | 44 | Mar. 1, 2003 |
| | OligoDB.pas | 8 | Aug. 3, 1999 |

-continued

| Folder | Files | Size (KB) | Date Created |
|---|---|---|---|
| | OligoFrm.dfm | 4 | Mar. 1, 2003 |
| | OligoFrm.pas | 8 | Mar. 1, 2003 |
| | Pjrclass.pas | 4 | Aug. 29, 2002 |
| | Prjclass.pas | 20 | Feb. 27, 2003 |
| | Simil.pas | 12 | Feb. 22, 2003 |
| | SqModule.dfm | 4 | Feb. 25, 2003 |
| | SqModule.pas | 4 | Feb. 25, 2003 |
| | Tables.pas | 12 | Feb. 25, 2003 |
| | VH_form.dfm | 4 | Feb. 27, 2003 |
| | VH_form.pas | 12 | Feb. 27, 2003 |
| | VHClass.pas | 8 | Feb. 27, 2003 |
| Stability | Complete.txt | 8 | May 13, 2001 |
| | DoubleMis.dat | 4 | May 13, 2001 |
| | DoubleMis.txt | 4 | May 12, 2001 |
| | ExtractN.cfg | 4 | May 13, 2001 |
| | InitialVal.dat | 4 | Aug. 13, 2000 |
| | Main.dfm | 4 | May 20, 2001 |
| | Main.pas | 8 | Jun. 28, 2001 |
| | NNdata.dat | 4 | Aug. 12, 2000 |
| | NNdata2.dat | 8 | May 13, 2001 |
| | OlgClass.pas | 44 | Sep. 29, 2002 |
| | Oligodes.rtf | 4 | Oct. 16, 2002 |
| | RichFmt.pas | 8 | Jun. 27, 2001 |
| | Rtfcolor.pas | 4 | Jun. 11, 2001 |
| | Stability.dpr | 4 | Oct. 16, 2002 |
| | TotalNN.txt | 4 | May 12, 2001 |
| Structure Windows | Combin.pas | 8 | Aug. 5, 1999 |
| | ConfigDlg.dfm | 4 | Jun. 25, 2001 |
| | ConfigDlg.pas | 4 | Jun. 25, 2001 |
| | DNAClassSec.pas | 20 | Jun. 20, 2001 |
| | DNAAoligoSec.pas | 24 | Jun. 20, 2001 |
| | DrawDNA.pas | 8 | Jun. 26, 2001 |
| | Estructure.cfg | 4 | Jun. 26, 2001 |
| | Estructure.dpr | 4 | Jun. 26, 2001 |
| | Formats.pas | 12 | Sep. 29, 1999 |
| | InitialVal.dat | 4 | Aug. 13, 2000 |
| | MainStruc.dfm | 36 | Jun. 26, 2001 |
| | MainStruc.pas | 8 | Jun. 26, 2001 |

-continued

| Folder | Files | Size (KB) | Date Created |
|---|---|---|---|
| | NNdata.dat | 4 | Aug. 12, 2000 |
| | OlgclassSec.pas | 40 | May 12, 2001 |
| | OOPlist.pas | 8 | Jun. 20, 2001 |
| | Results.txt | 4 | Jun. 21, 2001 |
| | SecEstructure.dfm | 4 | Jun. 25, 2001 |
| | SecEstructure.pas | 4 | Jun. 25, 2001 |
| | Secondary.pas | 8 | Jun. 20, 2001 |
| | Secundaria.cfg | 4 | Jun. 21, 2001 |
| | Secundaria.dpr | 4 | Jun. 25, 2001 |
| | Tools.pas | 8 | Apr. 3, 2000 |
| Tandem | AnalysisTan.dfm | 4 | Jul. 30, 1999 |
| | AnalysisTan.pas | 8 | Apr. 3, 2000 |
| | DDmodel.dat | 4 | Aug. 26, 1998 |
| | DDOtraLucia.dat | 4 | Feb. 16, 1999 |
| | DDSantaLucia.dat | 4 | Sep. 9, 1998 |
| | HomolTan.pas | 4 | Aug. 4, 1999 |
| | MainTan.dfm | 4 | Apr. 3, 2000 |
| | MainTan.pas | 8 | Apr. 3, 2000 |
| | ParamsTan.dfm | 4 | Aug. 3, 1999 |
| | ParamsTan.pas | 4 | Aug. 4, 1999 |
| | Tandem.cfg | 4 | Apr. 3, 2000 |
| | Tandem.dof | 4 | Apr. 3, 2000 |
| | Tandem.dpr | 4 | Aug. 4, 1999 |
| | Working.dfm | 4 | Mar. 11, 1999 |
| | Working.pas | 4 | Mar. 11, 1999 |
| VirtualHyb | Aboutbxvh.dfm | 116 | Aug. 3, 1999 |
| | Aboutbxvh.pas | 4 | Aug. 3, 1999 |
| | Analysis.pas | 4 | Mar. 31, 2002 |
| | Config.dfm | 4 | Mar. 31, 2002 |
| | Config.pas | 4 | Mar. 31, 2002 |
| | DrawDNAVH.pas | 4 | Aug. 3, 1999 |
| | InitialVal.dat | 4 | Aug. 3, 1999 |
| | MainVH.dfm | 16 | Mar. 10, 2002 |
| | MainVH.pas | 24 | Mar. 31, 2002 |
| | Mismatch.dat | 4 | Aug. 3, 1999 |
| | NNdata2.dat | 8 | Aug. 3, 1999 |
| | OOPlistVh.pas | 8 | Aug. 3, 1999 |
| | PosStbl.dat | 4 | Aug. 3, 1999 |
| | Registry.dpr | 4 | Aug. 3, 1999 |
| | Test.pas | 4 | Aug. 12, 1999 |
| | VirtualHyb.cfg | 4 | Mar. 31, 2002 |
| | VirtualHyb.dof | 4 | Mar. 31, 2002 |
| | VirtualHyb.dpr | 4 | Mar. 31, 2002 |
| | VirtualHyb.res | 4 | Aug. 15, 1999 |

BACKGROUND OF THE INVENTION

1. Field of the Invention

The present invention relates generally to the fields of molecular biology and nucleic acid analysis. More specifically, the present invention provides a novel computer program for the design of optimized sets of oligonucleotide probes for microarrays.

2. Description of the Related Art

Genosensors, also called oligonucleotide microarrays or "DNA chips," are miniature devices containing arrays of oligonucleotide probes tethered to a surface (Beattie, 1997a). By hybridizing target nucleic acid molecules to these arrays and analyzing the resultant hybridization patterns, comparative analysis of sequences can be conducted (Beattie, 1997b), such as detection of specific mutations, identification of microorganisms (Beattie, 1997a), profiling of gene expression (Duggan et al., 1999), and verification of sequencing data (Hacia, 1999). For any given DNA or RNA sequence a large number of potential probes could be derived; however, only a small subset is needed to manifest the desired characteristics of the analyte nucleic acid molecules. In order to design probes for successful use in genosensors it is necessary to minimize the probability of unspecific (mismatched) hybridization between the probe and any nucleic acid sequence other than the intended target site (Doktycz and Beattie, 1997). A computer program is needed to design probes that are useful in microarray analysis.

A computer program called Genosensor Probe Designer (GPD) is disclosed herein, which can be used for selecting the most suitable probes for a genosensor chip based upon several factors that could affect the hybridization process. These factors include thermal stability, secondary structure, and alternative binding sites within the nucleic acid analyte.

It is well known that thermal stability of duplex nucleic acids depends on nucleotide sequence, chain length and nucleic acid concentration, as well as the identity and concentration of counterions. It is possible to find optimal hybridization conditions for specific binding of any given probe with its target molecule, but when the hybridization reaction is carried out with numerous probes and target molecules (as with genosensor chips), a loss in specificity can occur. The loss occurs particularly if the thermal stabilities of arrayed probes paired with their target sequences vary widely, or if the complexity of the analyte nucleic acid is sufficiently high to present alternative, mismatch-containing hybrids. Thus, the hybridization of multiple probes with a nucleic acid analyte can produce signals that are partially or completely due to imperfectly matched hybrids (Doktycz and Beattie, 1997). This kind of ambiguous hybridization signal depends on the sequence and the identity of the non-paired bases. A complete understanding of the thermal stability of hybrids formed between probes and nucleic acid molecules requires information about the energetic contributions for all the possible interactions that can take part in the hybridization process (Doktycz and Beattie, 1997).

Furthermore, the target DNA or RNA molecules are capable of forming stable secondary structures that can make some target sequences inaccessible to hybridization with the complementary oligonucleotide probes. Moreover, large targets are also likely inhibited sterically from approaching the surface of the array (Southern et al., 1999). In order to avoid these problems, several approaches can be followed. If a reasonable prediction of the secondary structure of the target could be made, probes could be selected from regions that are not tied up in secondary structure. Effects of secondary structure could be reduced by fragmenting the nucleic acid preferably to a size close to that of the oligonucleotides on the array (Southern et al., 1999). Also, strategies of annealing with auxiliary oligonucleotides (tandem hybridization) have been proposed to eliminate interfering secondary or higher-order structures or to cover up unwanted (redundant) hybridization sites within the target DNA (Maldonado-Rodriguez et al., 1999a, 1999b; Maldonado-Rodriguez and Beattie, 2001). Finally, when genosensor chips are used to reveal differences between closely related nucleic acid sequences, the probes must be selected to specifically identify a particular sequence. In this case probes must be selected from regions with sufficient sequence variability to minimize nonspecific hybridization with related molecules. On the other hand, when probes are required for identifying a group of similar sequences, probes must be selected from conserved regions.

Several works dealing with nucleic acid sequence analysis and oligonucleotide probe design have been published previously (Bushnell et al., 1999; Galper et al., 1993; Shütz and von Ahsen, 1999; Vahrson et al., 1996; Li and Stormo, 2001; Pozhitkov and Tautz, 2002). One interesting work is Vahrson's library, called SCL-a, which is a C++ Object-Oriented library similar in some respects to that disclosed herein. Vahrson's library is specialized in the management of dynamical memory for manipulating long DNA sequences, whereas the library disclosed herein is specialized in the calculation of thermodynamic stability and the search for potential hybridization sites.

Object-Oriented support included in the Object Pascal library of Delphi is similar to that provided in C++. Classes are similar between Delphi and C++ programming languages; however, Object-Pascal language has a clearer syntax than that used by C++, and Delphi code can be easily translated to C++ if required with minimal complexity. Moreover, Delphi compiled native programs can run faster than those produced using C++ compilers.

A spreadsheet software program for thermodynamic melting point prediction of oligonucleotide hybridization based in the NN model has recently been developed (Shütz and von Ahsen, 1999). However, this program does not predict the specific hybridization patterns that could be expected with a given set of probes, and does not design sets of probes for the variety of Genosensor applications that are described herein.

Also a program for selection of optimal DNA probes for gene expression arrays has been published recently (Li and Stormo, 2001). Although this program uses criteria for selection of probes similar to those implemented in the software that is described in the present work, it is intended to select relatively long probes (more than 20 bases long) which are less convenient for single mutation discrimination. Also, an algorithm and program for selecting specific probes for species identification with microarrays has been published recently (Pozhitkov and Tautz, 2002). This algorithm considers position of mismatches which influences the selection; however, information is lacking about the experimental performance of the probes selected with this program.

Thus, in order to identify conserved or variable regions the complete alignment of the sequences under study must be conducted prior to selection of the most appropriate target regions for the subsequently designed probes. Consequently, in the design of optimized sets of oligonucleotide probes for nucleic acid analysis on genosensor arrays, careful consideration of numerous factors must be done, including the characteristics of the nucleic acid analyte, the type of analysis being performed, thermal stability of probe-target duplexes, secondary structure within the target sequence, and alternative probe binding sites within the target nucleic acid. The Genosensor Probe Designer software disclosed herein takes all of these factors into consideration.

SUMMARY OF THE INVENTION

A program for selecting optimized sets of oligonucleotide probes for use in genosensor chips (also known as oligonucleotide microarrays) is developed and disclosed herein. Selection of probes is based on thermodynamic stability, similarity degree properties and suitable parameter values for virtual hybridization. A more comprehensive analysis yielding even more confident predictions of hybridization patterns can be provided by inclusion of additional thermodynamic parameters such as the influence of dangling ends and contributions of non-standard nucleic acid interactions.

The Genosensor Probe Designer software disclosed herein was written in the programming language Borland Delphi (Borland International) Version 5.0. It can run on Windows 95, 98, Millennium, NT and XP operating systems. The computer program was developed based on the Object-Oriented Programming (OOP) methodology, and classes for representing the user interface, molecules, criteria and interactions are provided. The object-oriented feature of the Genosensor Probe Designer program facilitates the development of improved versions, accommodates among other information upgrades of the thermodynamic models.

The software developed herein was successfully tested in the laboratory, wherein a set of primers and probes directed against the 5' end region of the 16S rRNA sequences of several strains of *Pseudomonas* and other bacterial species were designed. Results from these experiments show specific hybridization patterns for each sequence tested, and criteria for selecting probes and predicting hybridization patterns were derived.

Thus, the present invention is drawn to a software system for designing and selecting oligonucleotide probes for use in DNA microarrays as well as methods of using such software to select optimal sets of oligonucleotide probes for use in DNA microarrays.

BRIEF DESCRIPTION OF THE DRAWINGS

FIG. 4 illustrates the importance of the stability of the probes at the experimental hybridization temperature. In the example two probes have similar sequence and the target site for probe A has a high degree of similarity with that of probe B. Melting temperature of probe A is designated as $Tm_A$. Probe B can hybridize ambiguously at lower temperature at the same site as probe A with a melting temperature $Tm_B$. If the experiment is carried out at a temperature close to $Tm_A$ only probe A will give a hybridization signal. However, if the experimental temperature is close to $Tm_B$ both probes can give hybridization signals.

FIG. 5 illustrates the importance of the degree of similarity between oligonucleotides and target sequences for the design of probes for Genosensors. Probes used to identify a specific DNA sequence among a collection of similar targets must be directed against the sites found to have the highest variation between the sequences. However, probes required to identify a group of similar sequences must be directed against the most conserved regions of the sequences.

FIG. 10 shows the algorithm used to estimate secondary structure between probes (SEQ ID NO: 28) and potential hybridization sites (SEQ ID NO: 29). M and N are used to design each sequence. Pairing between bases is checked by placing both sequences in an anti-parallel form. m and n are used to design positions in sequences M and N respectively. ParM and ParN designate nearest-neighbor doublets for sequences M and N. Match1 is the result for the comparison of the first base pair in a nearest-neighbor doublet, which can be true (match) or false (mismatch). Similarly Match2 is the result for the comparison of the second base pair. Matching patterns and their positions are used as flags to identify a particular substructure by means of a decision table, which is used to assign the correct free energy value associated to it. Here TableNN is the table of nearest-neighbor interactions values, and Len is the length of the duplex.

FIGS. 12A-12F shows the sequence alignments and positions of 9 mer probes 1-88 shown in Table 3 (SEQ ID NOS: 31-118) along the 16S rRNA gene sequences (SEQ ID NOS: 6-23).

In FIG. 15B spots 2-3, 6-8, 16 and 20 show a weak experimental signal and spots 21-22 and 27 show a strong experimental signal. In FIG. 15C spots 16-20 and 27 are probes with perfect match. In FIG. 15D spots 12, 14, 16, 20, and 27 are sites with DG range between −12 and −10 Kcal/mol; spots 21 and 24 are sites with DG range between −10 and −8 Kcal/mol; and spots 1, 3-4, 6-8, 15, 18, and 26 are sites with DG range between −8 and −6 Kcal/mol.

FIG. 18 shows the screen image of a program that calculates the thermal stability for perfect and mismatched hybrids. Free energy calculations use the same algorithm implemented in the VH algorithm. This function can be conveniently used for fast visualization of energetic contributions in the hybridization between any given pair of strands.

FIG. 25 shows the selection of probes for tandem hybridization (also named contiguous stacking hybridization) in the Genosensor Probe Designer Program. The GPD program has capabilities to select stacking (SEQ ID NOS: 159-185) and capture probes (SEQ ID NOS: 186-212) required for the tandem hybridization approach. The GPD program also shows the junction between the stacking and capture probes (SEQ ID NOS: 213-239).

DETAILED DESCRIPTION OF THE INVENTION

In the Object-Oriented Programming (OOP) terminology, classes are abstract data structures which encapsulate data and operations or methods used to manipulate them. Objects are instances of the classes, used for representing any item such as an oligonucleotide molecule or a window of the user interface (Vahrson et al., 1996). Classes or objects used in the program can be divided into interface and application classes or objects, depending on whether they are involved in the design of the user interface, or in the process to select the probes.

Figure 1:
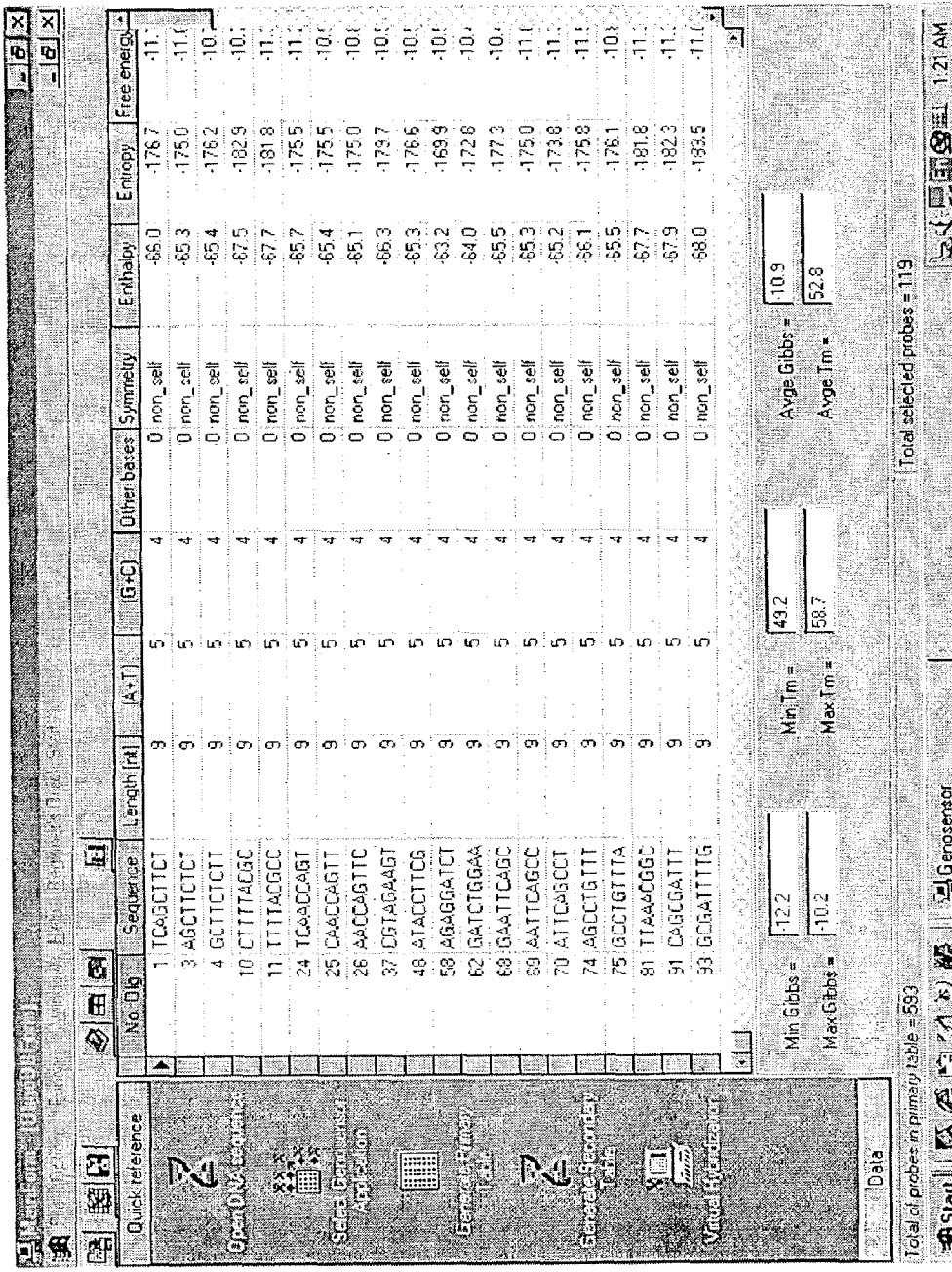
FIG. 1 shows a screen image of the Genosensor Probe Designer program running in the Windows Millenium environment. The program uses an advanced Multiple Document Interface (MDI) for its user friendliness. DNA and oligonucleotide sequences are conveniently manipulated and stored in Databases that are controlled by the Borland Database Engine (BDE).

Interface objects were developed using the Visual Component Library (VCL) provided within Delphi and the Orpheus 3.0 library (TurboPower Software Company). Both libraries have an extensive collection of Native Visual Components that permit the design of highly complex user interfaces. The user interface developed for the Genosensor Probe Designer program is based on the Multiple Document Interface (MDI) standard. FIG. 1 shows a general view of the Genosensor Probe Designer user interface.

The set of application objects is the core of the Genosensor Probe Designer program. They were developed using the Object Pascal Language provided for Delphi and these objects include all the classes for representing molecules, selection criteria, interactions between molecules and similarity degree. These objects are involved in the selection of probes. Since these objects are independent of the interface objects and the VCL, they can be used to develop other applications. Moreover, application objects can be divided into four groups. The first group of objects represents the DNA molecules involved in the hybridization process ("targets" and "probes"). The second set of objects represent interactions or processes involving the DNA molecules (e.g. the hybridization reaction). The third group includes objects which use methods based on thermodynamic criteria for rejecting or accepting probes and the fourth group contains objects with methods for evaluating similarity between targets and probes.

Figure 2:
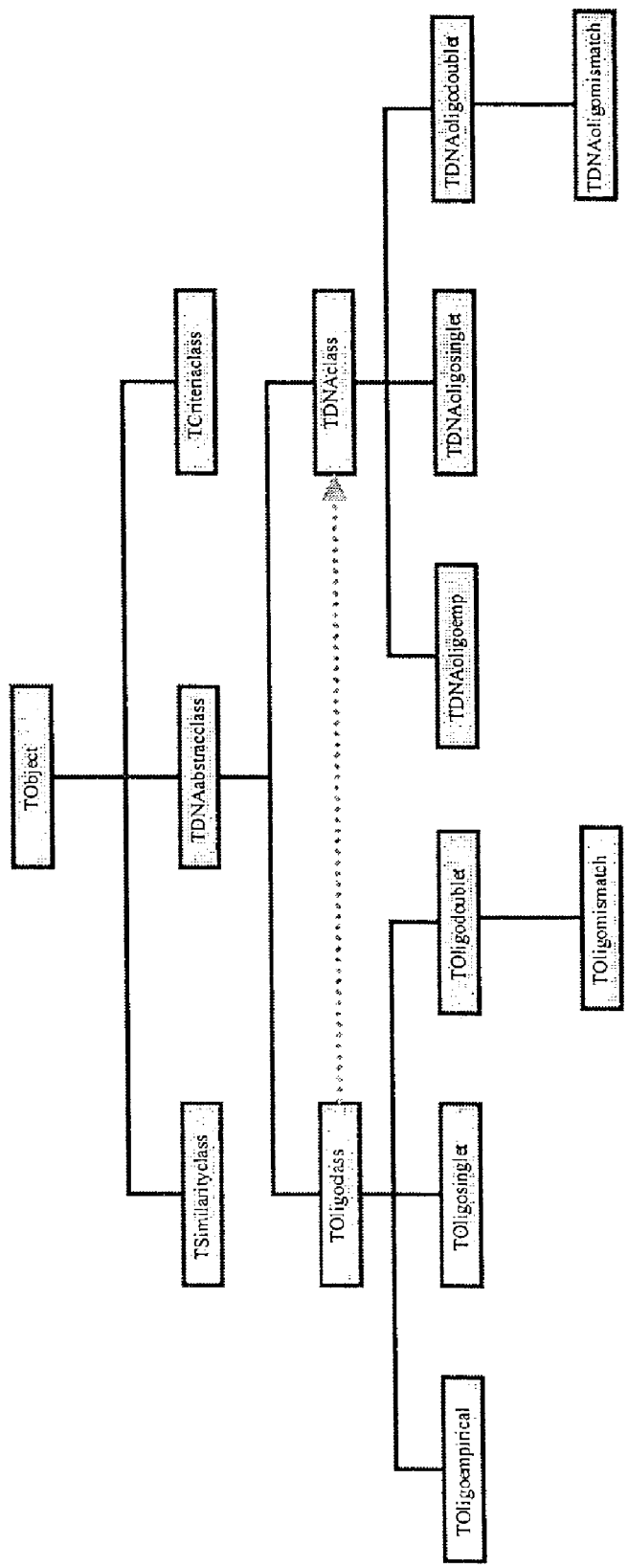
FIG. 2 shows the heredity relations between developed classes for the Genosensor Probe Designer Program. In the Delphi programming language of the Genosensor Probe Designer Program, every class is a descendant from the TObject class. One group of classes represents the molecules involved in the hybridization process. TDNAbstracclass is an abstract class, which defines all the common properties of the DNA molecules. TDNAclass and TOligoclass are abstract classes also, which define specific characteristics for long and short DNA sequences, respectively. Abstract classes are not directly used for object representation but they are used as intermediate steps for the design of other objects. TOligoclass has three descendent classes, which comprise different implementations for calculating Tm and other thermodynamic properties. A second group of classes represents the interactions between molecules, and these classes are derived from a combination of TDNAclass and TOligoclass classes. TDNAoligomismatch, like its relative, Toligomismatch, uses the doublet model to calculate the Tm and free energy. TvirtualHybridization, the most specialized class of this second group, is used to predict hybridization patterns. TCriteriaclass and TSymilarityclass are other types of classes, directly derived from the TObject class, and comprise methods and thermodynamic criteria to select probes and to evaluate similarity between target and probes, respectively. The character "T" is normally used for class referencing, while the instance of the class (the "object") is referenced using the same name as the class, omitting the "T."

FIG. 2 shows the hierarchical relationships between the objects that were developed. TDNAclass objects are computer representations of DNA molecules longer than 50 bp. These objects include characteristic DNA properties such as length, molecular weight and sequence composition, as well as methods for reading DNA sequences from data files. Sequences must be in FASTA or Genbank formats. Toligoclass objects are virtual representations of sequences with length up to 50 bp. Separate DNA objects for long sequences and oligonucleotides were developed because models to predict thermal stability for long and short nucleic acid molecules are different. For example, nucleotide sequence effects cannot be ignored in sequences shorter than 50 bp, while empirical models based on base composition alone can describe thermodynamic values such as Tm for long DNA sequences with reasonable precision. Nearest-neighbor (NN) models are better considered for describing properties of oligonucleotides (Cantor and Schimmel, 1980). Several data sets for calculating thermodynamic properties based in the nearest-neighbor model have been proposed and two main formats have been used for representing NN parameters, termed the singlet and the doublet formats (Owczarzy et al., 1997).

Singlet format considers contributions from H-bonding and stacking interactions separately and uses linearly independent equations for calculating thermodynamic properties. In the doublet format the entire NN interaction is considered in a single parameter and thermodynamic values for each of the NN base pairs are used. TOligoclass objects have descendent classes specialized for using NN parameters of both data formats. As can be seen in FIG. 2, a TOligoempirical class is also included to calculate oligonucleotide properties by using the empirical models. SantaLucia has shown a unified set of parameters (SantaLucia, 1998) which adequately describes thermodynamic properties for oligonucleotides using the doublet format and the complete set of NN parameters for energy contributions due to single mismatches and dangling ends has been published recently (Allawi and SantaLucia, 1997, 1998a, 1998b, 1998c; Peyret et al., 1999; Bommarito et al., 2000). These data sets have been implemented in the TOligomismatch class.

TDNAoligoclasses are combined classes derived from TDNAclass and TOligoclass, and were developed for describing interactions between oligonucleotides and target DNA molecules. These objects include methods for binary mapping of the DNA molecules, which are required for identifying potential sequences of probes generated from the target molecule and for evaluating similarity between oligonucleotides and target DNA sequences.

TCriteriaclass includes several criteria for rejecting or accepting oligonucleotide probes based upon their thermodynamic properties. The selection criteria are based upon user-specified [A+T] composition, [G+C] composition, melting temperature (Tm) range, enthalpy, entropy, free energy, internal repeated sequences, sequence symmetry of probes, and frequency of occurrence. The user can conveniently disable any of the evaluated properties in order to customize the selection procedure.

TSimilarityclass class includes methods for evaluating similarity between probes and targets. By using this class, specific probes can be selected by establishing convenient cut-off values for similarity between probes and sites within the target DNA sequences. To accomplish this, a search of similarity can be performed against sequences contained within Internal or External DNA databases. The naming conventions for databases are based upon considerations of whether the DNA sequences are defined within the internal DNA database that is generated when the program starts (see below). External databases can contain several DNA sequences within a single text file and they must be in FASTA format, while internal databases are composed of several text files, each containing just a single DNA sequence in FASTA or Genbank formats. Methods defined in TSimilarityclass can show very detailed information about all the sites within the DNA sequences where probes have significantly high similarity degree. This information can be useful to predict potential hybridization of the probes as well as to know whether the probes are specific for one particular DNA sequence or a set of sequences.

Figure 3:
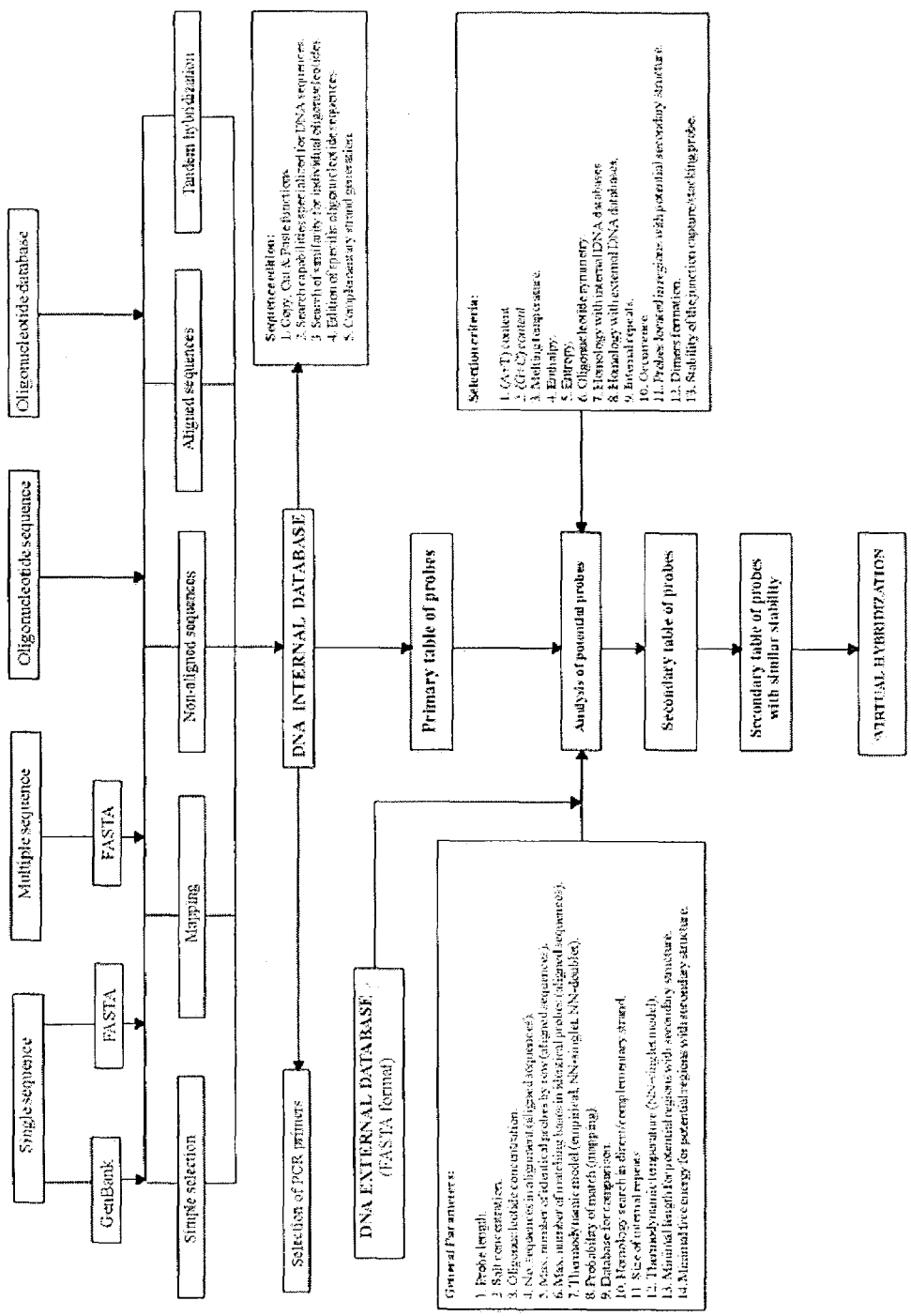
FIG. 3 summarizes the applications and functions of the Genosensor Probe Designer program. The program can use single or multiple target sequences, oligonucleotide sequences, or oligonucleotide databases.

FIG. 3 shows in detail the applications performed by the Genosensor Probe Designer program. The program can be used for automatic or manual selection of probes targeted to particular DNA sequences. For any application, input data can include target DNA sequences (single or multiple), DNA sequence databases, oligonucleotide sequences or oligonucleotide databases. Target DNA sequences must be in Genbank or FASTA formats (only FASTA format for files containing multiple sequences). For the aligned sequences analysis, sequences must be aligned first with any alignment tool such as Clustal X (Thompson et al., 1997). As soon as the initial data are read, a genosensor application can be specified.

From the sequences specified in the initial data section, an internal DNA database table is created including the entire target DNA sequences from which probes will be selected. Then, a primary table of oligonucleotides is generated containing all possible probes of a defined length that can be derived from the DNA target molecules. When the user-defined selection criteria within Tcriteriaclass are applied, a secondary table is created containing just the probes with appropriate composition and thermodynamic properties. An additional search can then be performed with the probes contained in the secondary table in order to make a further selection of specific probes. For this analysis, the program uses the methods defined in an instance of TSimilarityclass. Similarity degree is evaluated between probes and selected target DNA molecules contained in the internal DNA database (defined before) or in external DNA databases which are text files containing sequences saved in FASTA format.

An additional analysis can be made with the table of specific probes in order to obtain oligonucleotides of variable length but similar stability. This analysis adds or deletes nucleotides from one or both ends of the probe based on the flanking DNA sequence in the target site. As the length of the probes changes an additional similarity analysis can be performed in order to delete sequences that no longer have the desired specificity.

Using the final table of specific oligonucleotides, an analysis of the possible hybridization of the probes against the DNA sequences in the internal database can be performed. This analysis shows target sites for perfect hybridization, as well as sites that could be potential sites for ambiguous hybridization due to complementarity degree and stability values. This approach is called Virtual Hybridization (VH).

In order to perform the VH analysis the following rules are defined in the program:

(i) For a given probe length (L) a minimal value (minbasescom) for the number of complementary bases between probes and potential hybridization sites is defined such that $2 \leq minbasescom \leq L$.

(ii) For a given probe length (L) a minimal value (minblocksize) for the length of contiguously paired bases within potential hybridization sites is specified such that $2 \leq minblocksize \leq L$.

(iii) The complementarity degree between probes and potential hybridization sites is evaluated along the target sequences (representing all nucleic acid sequences present in the analyte). Potential Hybridization Sites are selected as sites where the number of complementary bases between the probe and the evaluated site is equal to or greater than minbasescom or sites where a block of contiguously paired bases is equal to or greater than minblocksize.

(iv) Potential hybridization sites with 100% complementarity with the probe are shown as sites with only Watson-Crick base-pairing or sites of perfect hybridization.

(v) Potential hybridization sites with less than 100% complementarity with the probe are shown as sites with some non-Watson-Crick paired bases or sites of ambiguous hybridization.

(vi) An additional analysis of the thermal stability of probes paired with their respective potential hybridization sites is performed using the NN model (including mismatch data). Free energy values calculated by this model are useful to estimate the hybridization probability. In general, at more negative $\Delta G°$ values the probability of stable pairing is higher.

(vii) $\Delta G°$ cutoff values are defined (Gcutoff). Potential hybridization sites with $\Delta G°$ values equal to or greater than Gcutoff are shown as sites of high hybridization probability.

Virtual Hybridization (VH) is an important new capability that can yield a predicted hybridization pattern from any given combination of oligonucleotide probes and target sequences. By incorporating VH analysis during the selection of probes, ambiguous hybridization can be minimized or avoided entirely, thus optimizing the effectiveness of genosensor chips. A more comprehensive implementation of the VH strategy can be provided by expansion of the predicted vs. experimental hybridization data set, utilizing a larger collection of sequence-verified targets. Currently, the program parameters are adjusted in order to show only the sites of high hybridization probability such that a virtual hybridization pattern is obtained.

The Genosensor Probe Designer software disclosed herein can use any or all of the program applications described below for selecting the probes.

In the simple selection program application a set of probes for a particular DNA sequence will be generated. Selection criteria are based only on thermodynamic and composition properties.

The mapping application is a very fast procedure for selecting all the possible probes of any size (up to 15-mers) that can be obtained from any sequence or sequences, usually a complete genomic sequence.

The non-aligned sequences application is used in order to select probes that are specific for particular sequences (which could be similar or not). However, the search procedure is time-consuming and could be slow for the analysis of long sequences.

In the aligned sequences application, DNA sequences aligned with any alignment tool such as Clustal-X are read.

Then, the alignment is scanned column by column. If oligonucleotide probes are required for hybridization with the conserved regions of the alignment, contiguous columns with identical bases in all the rows are selected until the probe size is reached. Such probes are sent to the primary table of oligonucleotides. Alternatively, probes could be required for revealing the differences between the DNA sequences included in the alignment. In the latter case, columns containing several base variations are selected and probes are derived from those columns in order to obtain a set that can be used to represent the maximum differences between the aligned sequences.

In the tandem hybridization application (Maldonado-Rodriguez and Beattie, 2001; Maldonado-Rodriguez et al., 1999a,b), short probes (typically 5-mer to 9-mer) called the "capture" probes can be selected as in the single selection application. After the secondary table of capture probes is built, longer "stacking" probes are selected contiguous to the 5' or 3' end of the capture probes. Stacking probes are typically 20-30 nucleotides or longer without restriction regarding their sequences. Alternatively, capture and stacking probes can be selected manually from specific sites within the target.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Program Details and Algorithms

Figure 6:
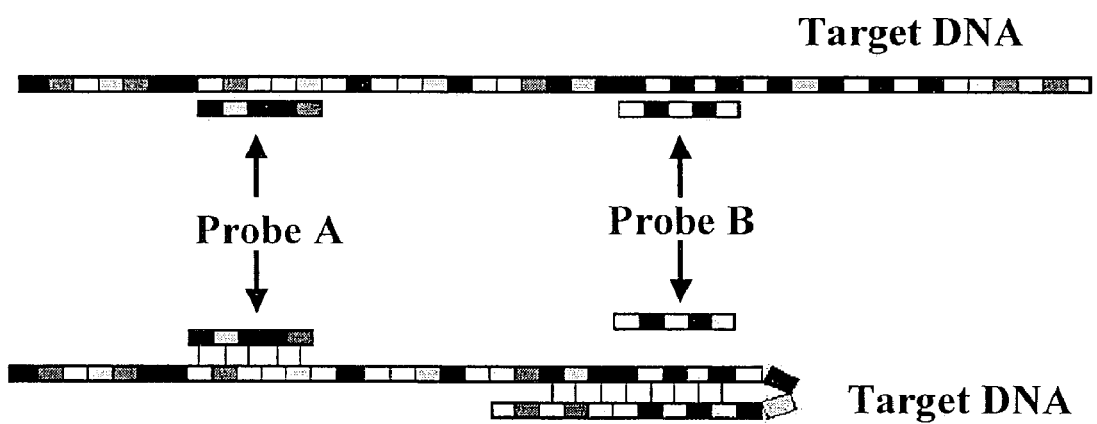
FIG. 6 illustrates the importance of the accessibility of hybridization sites in target DNA molecules. In this example, two probes are directed against different sites in the target DNA molecule. However, the secondary structure of the target can prevent probe B from accessing its target.

There are several aspects of oligonucleotide interactions which are taken into consideration in the algorithms of the Genosensor Probe Designer program. Some of these design considerations are illustrated and discussed in FIGS. 4-6.

Frequently it is important to know the occurrence of particular n-mers in a particular DNA sequence in order to be able to design probes for DNA finger printing or SBH. The occurrence of particular n-mers can be determined by searching all possible combinations of n-mers or mapping of the DNA target sequence.

The number of possible combinations of n-mers is equal to $4^n$. Therefore, there are 16 combinations for dimers. As an example, the occurrence of each dimer on the sequence: 5'-TATAGTAGAAACCACAA-3' (SEQ ID NO.1) can be searched by comparing target/pattern (using Brute search, Boyer-Moore, or Quicksearch) with the pattern sliding along the target. Searching each dimer will obtain the following results: AA=3, TA=3, AC=2, TC=0, AT=1, TT=0, AG=2, TG=0, CA=2, GA=1, CC=1, GC=0, CT=0, GT=1, CG=0, GG=0.

For mapping all the probes of a given size in a particular sequence, each probe sequence can be represented with a number in base 4: Probe=$N_1 N_2 \ldots N_m$ with $N_i=\{A, C, G, T\}$ with m<16. If A=0, C=1, G=2, and T=3 then, in the case of dimers:

| Seq base$_4$ | base$_{10}$ | Seq base$_4$ | base$_{10}$ |
|---|---|---|---|
| AA = 00 | 0 | GA = 20 | 8 |
| AC = 01 | 1 | GC = 21 | 9 |
| AG = 02 | 2 | GG = 22 | 10 |
| AT = 03 | 3 | GT = 23 | 11 |
| CA = 10 | 4 | TA = 30 | 12 |
| CC = 11 | 5 | TC = 31 | 13 |
| CG = 12 | 6 | TG = 32 | 14 |
| CG = 13 | 7 | TT = 33 | 15 |

Figure 7:
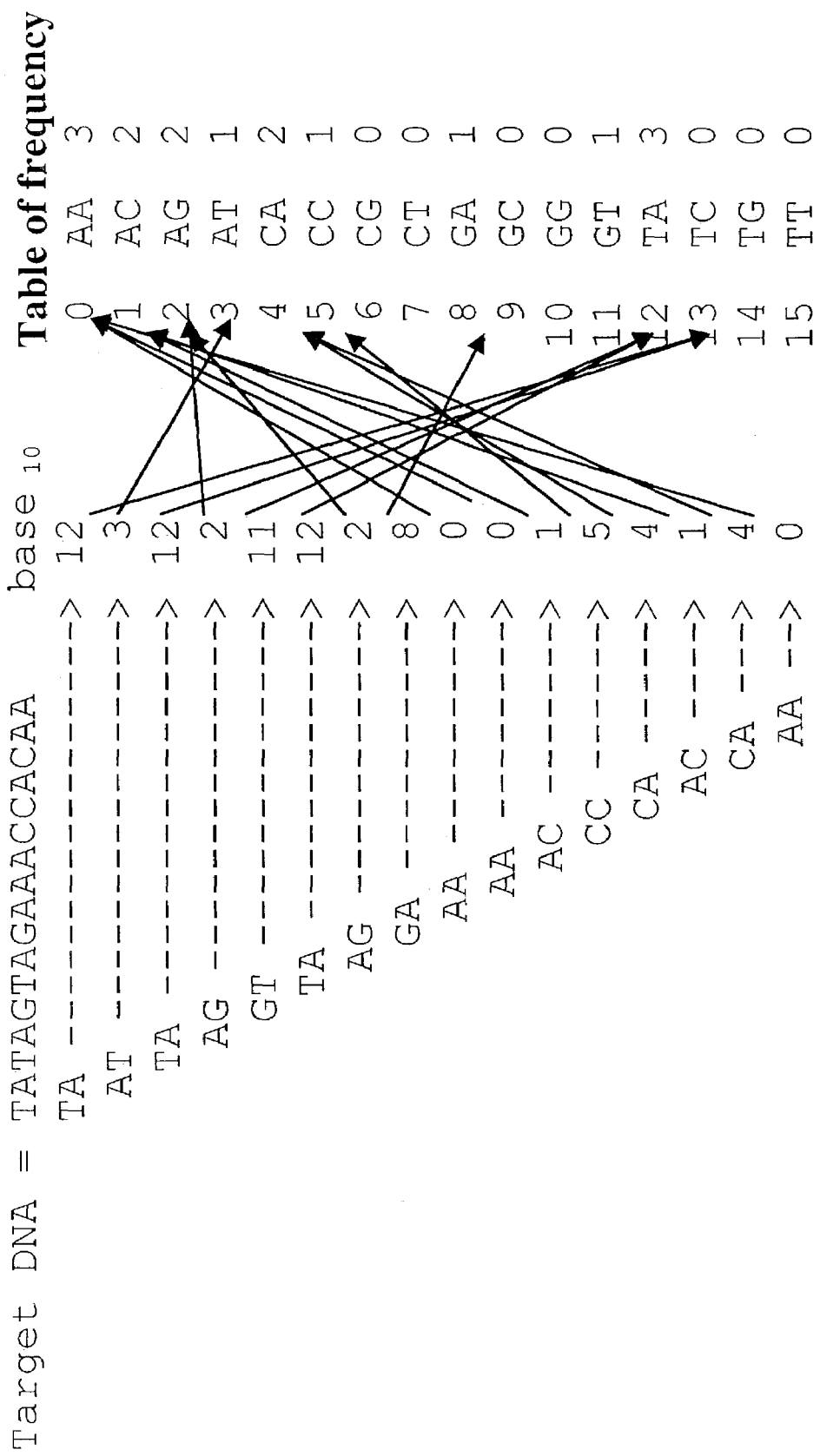
FIG. 7 shows an example of mapping all the probes of a given size in a particular sequence (SEQ ID NO: 1).
Figure 8:
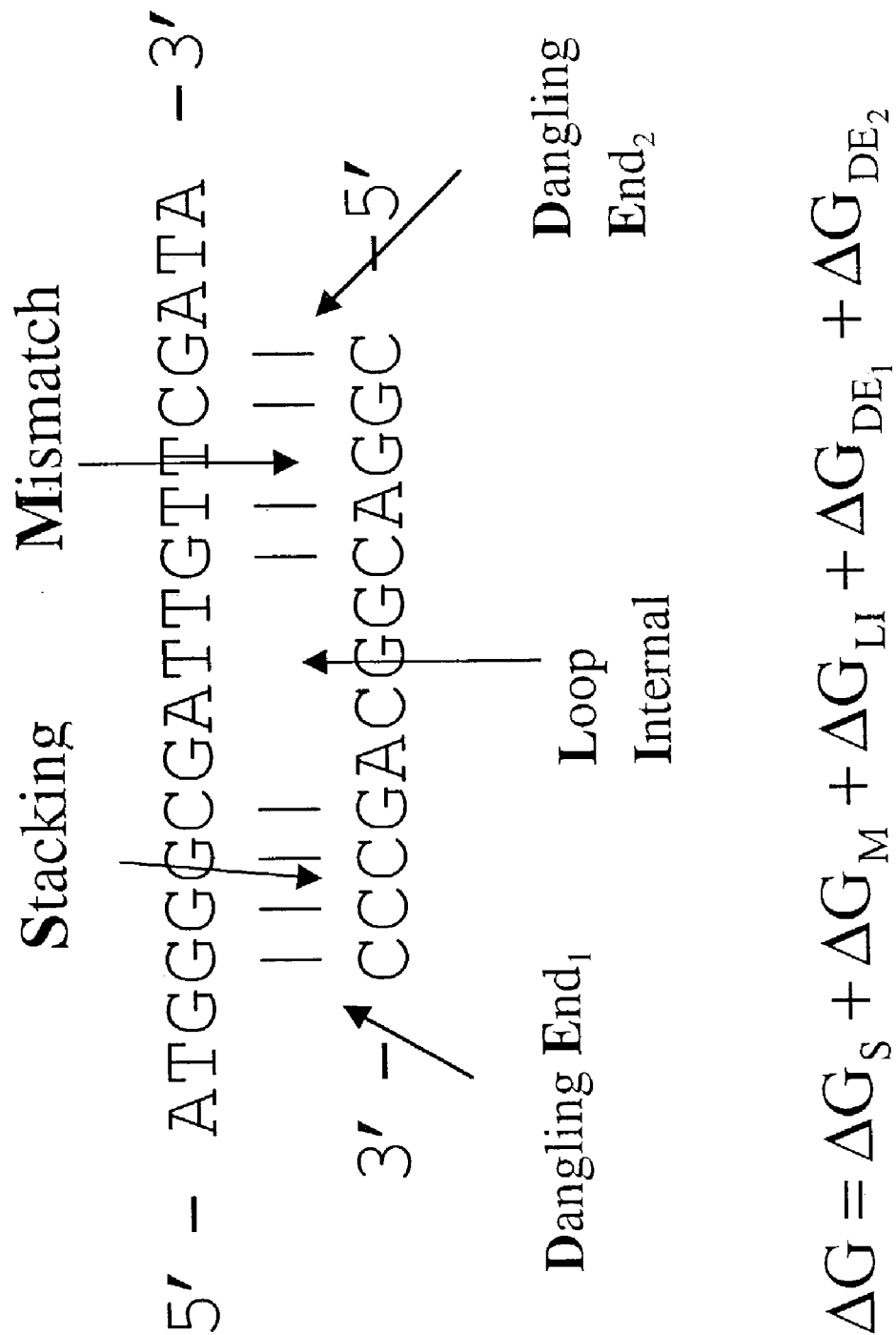
FIG. 8 shows thermodynamic properties of oligonucleotides (SEQ ID NOS: 24-25) and energetic contribution of several substructures.

And the occurrence of each dimer on the sequence: 5'-TATAGTAGAAACCACAA-3' (SEQ ID NO.1) can be mapped as shown in FIG. 7.

For ambiguous sequences, the characters R, Y, M, K, S, W, H, B, V, D, N and X are used to represent ambiguous bases in DNA sequences: R={A,C}, Y={C,T}, M={A,C}, K={G,T}, S={G,C}, W={A,T}, H={A,C,T}, B={G,T,C}, V={G,C,A}, D={G,A,T}, N or X={A,C,T,G}. If target='ACNAC' and pattern='ACTAC', then the probability of perfect match between target and pattern can be defined as: P=1/# combinations=$1/2^r 3^h 4^n$, where r=number of Rs, Ys, Ms, Ks, Ss and Ws in target; h=number of Hs, Bs, Vs, and Ds; n=number of Ns or Xs.

The searching and mapping methods described above were used for finding specific n-mer in the E. coli genome sequence (4,639,221 bp) using a Pentium 260 Mhz processor. The time of search for Quicksearch was 4.2 hours, whereas the time of search for mapping was 0.52 hour.

Also, these methods were used for finding specific n-mers in the Small Subunit rRNA Database (22,324 sequences, average size=1093 bp). This database has ambiguous bases in several sequences (9271 sequences). Using a Pentium 260 Mhz processor, the time of search for Quicksearch was 1.5 days, whereas the time of search for mapping was 0.45 hour.

Virtual Hybridization Algorithm

Accurate prediction of the thermal stability for hybridization reactions has become a very important issue in several molecular biology techniques. Reliable prediction of the free energy associated with the formation of the DNA duplex is necessary in order to select the optimal experimental conditions for specific detection and/or identification of target molecules. This aspect is dramatically important in DNA microarrays where several hybridization reactions are carried out simultaneously. If the thermal stability of the different probes used in the array is too different, a loss in the specificity of the hybridization can result, whereby "hybridization signals" are due to both perfect match between the probes and target but also some imperfectly matched hybrids, which is known as ambiguous hybridization.

Thermodynamic models have been developed in order to predict the free energy values and other thermodynamic parameters associated with the thermal stability of DNA duplexes. The most accurate model for oligonucleotides is based on stacking interactions between neighboring bases in the duplex, and it is named the nearest-neighbor interactions model.

The nearest-neighbor model can predict the thermal stability for both perfectly and imperfectly matched duplexes, and can thus be used for predicting whether oligonucleotides can hybridize under a given set of experimental conditions. We call such a theoretical approach Virtual Hybridization (VH). If accurate parameters for the nearest-neighbor model are used, then VH can simulate the results of hybridization experiments under defined experimental conditions with a high degree of accuracy. Parameters have been derived and disclosed herein to predict patterns of hybridization of PCR products derived from 16S rRNA genes of several bacterial species with arrays of 9-mer probes. In this section a more detailed description of the algorithm used for virtual hybridization is given.

The Nearest-Neighbor Model

The nearest-neighbor model considers thermal stability as sequence-dependent and in terms of base pair doublets (nearest-neighbors). In duplex DNA there are ten possible combinations of such nearest-neighbors:

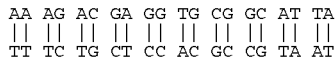

```
AA  AG  AC  GA  GG  TG  CG  GC  AT  TA
||  ||  ||  ||  ||  ||  ||  ||  ||  ||
TT  TC  TG  CT  CC  AC  GC  CG  TA  AT
```

The NN model assumes that the stability of a given base pair depends on the identity and the orientation of the neighboring base pairs. In the most simple format of the NN model, the free energies for oligonucleotide duplexes result from the sum of its nearest-neighbor interactions. It has been proven that the NN model also serves to estimate the contribution of other secondary structure components. Currently, the NN model has been extended to predict the contribution of several components of the secondary structure of DNA oligonucleotides such as: Stacking regions, Internal single mismatches, Dangling ends.

The Algorithm

Virtual Hybridization analysis has been conceived as a two-stage approach. The first stage aims to find the most probable sites within a target sequence where a particular probe can hybridize. This search includes two parameters called minbasescom and minblocksize. The values of these parameters are dependent on the probe size and, for a given probe length: $2 \leq \text{minblocksize} \leq \text{minbasescom} \leq L$, where L is the length of the probe, minblocksize is the minimal accepted length of contiguously paired bases between a probe and a potential hybridization site, and minbasescom is the minimal accepted number of complementary bases between a probe and a potential hybridization site. A Virtual Hybridization search begins by looking for sites in the target molecule where the number of contiguously paired bases or the number of complementary bases with the probe are equal to or greater than minblocksize or minbasescom, respectively. Sites found by means of this search are stored and considered as potential hybridization sites.

The second stage of the virtual hybridization approach is the calculation of the free energy associated with the formation of duplexes between the probe and the potential hybridization sites.

Bases between a particular site and the probe are compared in order to decide if bases can be paired (match) or not (mismatch). Matches and mismatches between bases are grouped by pairs. This approach does not presently consider gaps on that comparison. Different components of the secondary structure of the duplex can be found in this way. Table 1 summarizes several secondary structure components (substructures) and abbreviations used to represent them.

TABLE 1

Secondary Structure Components For DNA Duplexes

| Structure | Abbreviation |
| --- | --- |
| 5' Terminal mismatch | EndMis5 |
| 3' Terminal mismatch | EndMis3 |
| Double internal mismatch | DoubInt |
| 3' Double external mismatch | DoubEx3 |
| 5' Double external mismatch | DoubEx5 |
| Perfect paired dinucleotide | Perfect |
| Penultimate single mismatch close to 3' end | PenSing3 |
| Penultimate single mismatch close to 5' end | PenSing5 |
| Single internal mismatch | SingMis |

Figure 9:
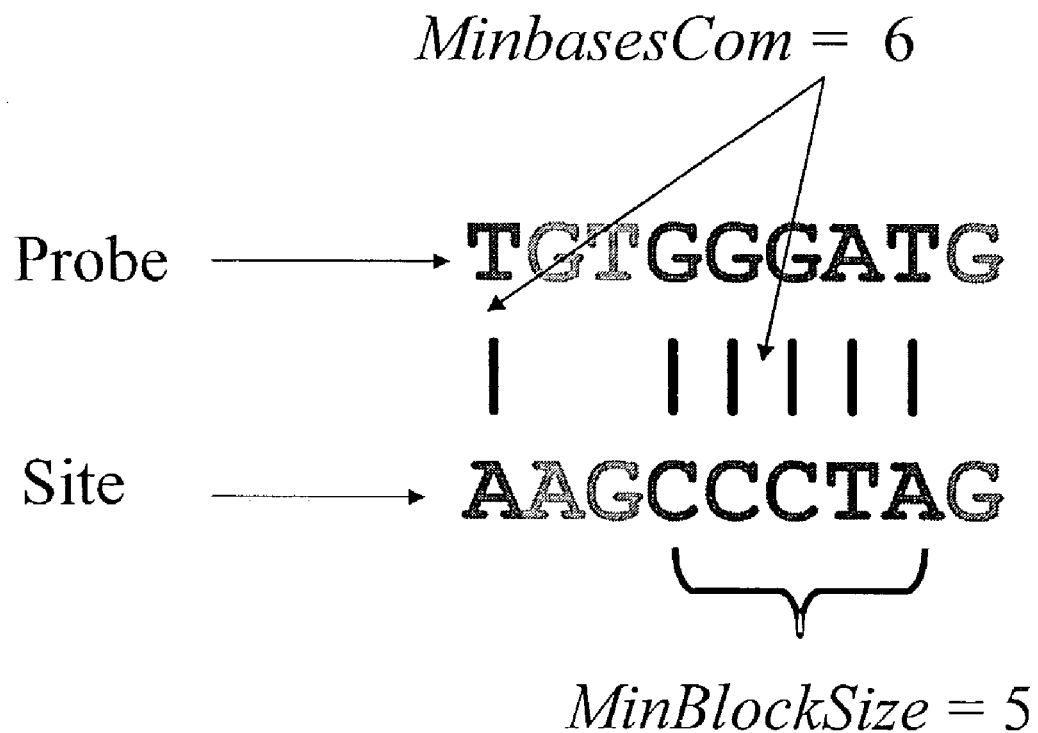
FIG. 9 shows the first step for the virtual hybridization algorithm. Potential hybridization sites are found by evaluating the number of complementary bases and the number of contiguously paired bases between sites in the target sequence (SEQ ID NO: 27) and the probe (SEQ ID NO: 26) (placing both in an anti-parallel form). Sites where the number of complementary bases or the size of a block with contiguously paired bases is greater than MinBasesCom and MinBlockSize respectively are stored as potential hybridization sites.

Matching patterns for each of the nearest-neighbors of the duplex can be combined with the positions of such patterns in the duplex in order to identify a secondary structure component as is illustrated in FIG. 9. Then, free energy values associated with each substructure can be calculated by means of a decision table as illustrated in FIG. 10. The free energy value for the duplex will be the sum of all the individual free energy values associated for each substructure.

The nearest-neighbor data set has not been completed to represent the contributions of all the secondary structure components of the DNA. For this reason some values need to be estimated from separate considerations.

Thermodynamic values for terminal mismatches are not published yet. However, some studies indicate that terminal mismatches have stabilizing values (negative free energy values). Free energy values for terminal mismatches in this prediction have been assumed to be zero, however, a more confident prediction of the thermal stability will be possible when precise values for these contributions are available.

Free energy values for double and multiple contiguous internal mismatches are also not published. Estimated values have been derived for these interactions assuming that internal mismatches have destabilizing values (positive free energies).

Figure 11:
FIG. 11 shows the effect of penultimate mismatches in oligonucleotide duplexes (SEQ ID NO: 30). The first structure where bases in both ends are paired is more unstable than the second where the bases in the ends are untied. (From Allawi and SantaLucia, 1997).

Penultimate mismatches deserve special attention. Free energy values for structures with penultimate mismatches are greater (more unstable) than values calculated by considering that the paired bases in the end adjacent to the penultimate mismatch are untied as shown in FIG. 11. Theses calculations are in agreement with experimental observations. When free energy values for such duplexes are calculated with the algorithm described before, ends are not untied. An additional analysis is performed when penultimate mismatches are found in order to untie the paired bases in the ends adjacent to the mismatches.

Once the free energy value for the duplex is calculated, it is compared with specified cut-off values. The cut-off values can be assigned for particular experimental conditions. If free energy of the duplex is less than or equal to the cut-off value (i.e., if it has a greater negative free energy value than the cut-off value), then site is marked as a high probability of hybridization site or probable signal.

EXAMPLE 2

Oligonucleotide Arrays Targeted to Microbial 16S rRNA Genes

Successful performance of algorithms implemented in the Genosensor Probe Designer program has been demonstrated through the discrimination of *Pseudomonas aeruginosa* and closely related bacterial strains via hybridization fingerprinting using genosensor chips. The seven test strains and the accession numbers for the 16S rRNA gene sequences are listed in Table 2.

TABLE 2

Accession Numbers

| Accession | Definition | Length (nt) |
|---|---|---|
| AB002661 | Bacillus sp. gene for 16S rRNA, complete sequence. | 1553 |
| AB020208 | Bacillus pumilus DNA for 16S ribosomal RNA. | 1471 |
| AF064460 | Pseudomonas veronii 16S ribosomal RNA gene, complete sequence. | 1521 |
| D84006 | Pseudomonas alcaligenes 16S rRNA gene, complete sequence. | 1530 |
| Z76662 | P. fluorescens 16S rRNA gene. | 1507 |
| AF017749 | Stenotrophomonas maltophilia 16S ribosomal RNA gene, complete sequence. | 1507 |
| D84020 | Pseudomonas putida 16S rRNA gene, complete sequence. | 1527 |
| X06684 | Pseudomonas aeruginosa DNA for 16S rRNA. | 1537 |
| AB001447 | Pseudomonas syringae pv. Myricae DNA for 16S ribosomal RNA. | 1538 |

DNA sequences encoding 16S rRNA genes of the seven microbial test strains (including closely related pseudomonads) were aligned with the aid of the Clustal X program (Thompson et al., 1997). From the analysis of the produced alignment, three conserved regions which delimit two highly variable regions (named "A" and "B") near the 5' end of the gene were found. The conserved regions were analyzed to find convenient PCR primers for the amplification of the regions A and B based on established rules for PCR primer selection (Rychlik, 1993). PCR forward primers were derivatized with a 5'-Biotin group to facilitate single-stranded target DNA purification. PCR reverse primers were derivatized with a 5'-fluorescent label (CY3 or CY5) to enable visualization of the hybridization patterns.

The primer sequences (5'->3') were as follows:

```
Region A forward primer
5'-CTCCTAQCGGGAGGCAGCAG-3'     (SEQ ID NO.2)

Region A reverse primer
5'-GTATTACCGCGGCTGCTGG-3'      (SEQ ID NO.3)

Region B forward primer
5'-CCAGCAGCCGCGGTAATAC-3'      (SEQ ID NO.4)

Region B reverse primer
5'-GGCGTGGACTACCAGGGTATC-3'    (SEQ ID NO.5)
```

For PCR amplification of the combined region AB, the 5'-biotin forward primer for Region A was used together with the 5'-fluorescent reverse primer for Region B. The PCR product from region "A" is located between nucleotides 356 and 554, yielding a 197 bp fragment for P. aeruginosa and a 198 bp fragment for the six other species. The PCR product from region "B" is positioned between nucleotides 533 and 830, forming a 293 bp fragment for P. aeruginosa and a 294 bp fragment for the remaining species. The distal pair of primers yields a larger "AB" PCR product encompassing regions "A" and "B" that has a length of 471 bp for P. aeruginosa and 473 bp for the other species.

The sequences of the seven PCR products for each region were realigned using Clustal X and the resultant alignment was analyzed using the aligned sequences module of the Genosensor Probe Designer program to select 9-mer probes. In this module an alignment of DNA sequences is read and then scanned column by column. Columns containing several base variations are selected and probes are derived from those columns in order to obtain a set that can be used to represent the maximum differences between the aligned sequences. In order to verify that probe sequences were present only within the intended target sites, all selected probes were tested for 100% degree of similarity against all sequences in the alignment.

As a result of this process a set of 87 nonamer probes (28 for region "A" and 59 for region "B") directed against the most highly variable regions of the alignment was selected (Table 3). FIG. 12 displays the sequence alignments and positions of 9 mer probes along the 16S rRNA gene sequences. These 9 mer probes were not designed for similar duplex stability (Tm value) and were not analyzed for similarity degree below 100% within the target sequences, thus it was anticipated that some of them could yield ambiguous hybridization with other sites within the 16S rRNA gene targets.

PCR products derived from each of the seven bacterial test species were hybridized to genosensor chips bearing the selected probes for each region. Results of these experiments showed unique hybridization patterns for each species. The experimental details of the PCR, oligonucleotide array formation, and hybridization experiments have been reported separately (Reyes-Lopez et al., 2003).

TABLE 3

Listing of Oligonucleotide Probe Sequences. Calculated Tm And $\Delta G^0$ Values. And Species To Which Each Probe Is Specific (Single Perfect Match)

| Probe | Sequence (5'->3') | Tm (° C.) | $\Delta G^0$ (Kcal/ mol) | Targeted Species (perfect sequence match with test strains) |
|---|---|---|---|---|
| 1 | AAGTCTGAC | 32.03 | -10.49 | B. pumilus |
| 2 | AGTCTGACG | 37.60 | -11.66 | B. pumilus |
| 3 | GGAGCAACG | 42.53 | -12.72 | B. pumilus |
| 4 | GTGAGTGAT | 32.18 | -10.54 | B. pumilus |
| 5 | TGAGTGATG | 32.22 | -10.55 | B. pumilus |

TABLE 3-continued

Listing of Oligonucleotide Probe Sequences. Calculated Tm And ΔG⁰ Values. And Species To Which Each Probe Is Specific (Single Perfect Match)

| Probe | Sequence (5'->3') | Tm (° C.) | ΔG⁰ (Kcal/mol) | Targeted Species (perfect sequence match with test strains) |
|---|---|---|---|---|
| 6 | GGAGAAGCC | 39.68 | -12.08 | - - - |
| 7 | GCAGTTACC | 35.95 | -11.27 | P. syringae, P. veronii |
| 8 | CAGTTACCT | 30.93 | -10.31 | P. syringae, P. veronii |
| 9 | CGAGAGTAA | 31.38 | -10.35 | B. pumilus |
| 10 | GAGAGTAAC | 28.35 | -9.62 | B. pumilus |
| 11 | GTAACTGCT | 33.02 | -10.71 | B. pumilus |
| 12 | ATACCTTGC | 32.77 | -10.71 | P. aeruginosa, P. alcaligenes |
| 13 | AACTGCTCG | 39.85 | -12.16 | B. pumilus |
| 14 | TACCTTGCT | 34.42 | -11.11 | P. aeruginosa, P. alcaligenes |
| 15 | TACGTTAGT | 28.85 | -9.93 | P. putida, P. fluorescens |
| 16 | CCTTGCTGT | 39.02 | -11.98 | P. aeruginosa, P. alcaligenes |
| 17 | CGTTAGTGT | 33.56 | -10.80 | P. putida, P. fluorescens |
| 18 | CGTGATTGT | 35.05 | -11.13 | P. syringae, P. veronii |
| 19 | GTTAGTGTT | 27.90 | -9.63 | P. putida, P. fluorescens |
| 20 | GCTGTITGA | 35.24 | -11.16 | P. aeruginosa, P. alcaligenes |
| 21 | GCTGTTTTG | 34.18 | -10.86 | P. syringae |
| 22 | AGTGTITCG | 34.90 | -11.08 | P. fluorescens |
| 23 | AGTGTTTTC | 29.30 | -9.91 | P. putida |
| 24 | GTTGGGATG | 35.50 | -11.20 | - - - |
| 25 | GTGTYFCGA | 35.04 | -11.10 | P. fluorescens |
| 26 | CCTTGACGG | 40.76 | -12.32 | B. pumilus |
| 27 | TTGACGTTA | 31.17 | -10.38 | P. syringae, P. aeruginosa, P. alcaligenes, P. veronii |
| 28 | GTACCTAAC | 28.08 | -9.60 | B. pumilus |
| 29 | GTGGTTCAG | 35.70 | -11.20 | P. aeruginosa, P. alcaligenes |
| 30 | TGGTTCAGC | 39.14 | -12.00 | P. aeruginosa, P. alcaligenes |
| 31 | GGTTCAGCA | 39.14 | -12.00 | P. aeruginosa, P. alcaligenes |
| 32 | GTTCAGCAA | 35.24 | -11.16 | P. aeruginosa, P. alcaligenes |
| 33 | TTCAGCAAG | 34.43 | -11.00 | P. aeruginosa |
| 34 | AGCAAGCTT | 37.74 | -11.77 | P. alcaligenes |
| 35 | AGCAAGTFG | 35.09 | -11.14 | P. aeruginosa |
| 36 | GCAAGCTTG | 39.04 | -11.94 | P. alcaligenes |
| 37 | GCAAGTTGG | 37.95 | -11.70 | P. aeruginosa |
| 38 | CAAGCTTGA | 34.43 | -11.00 | P. aeruginosa |
| 39 | AAGCTTGAT | 31.06 | -10.43 | - - - |
| 40 | AAGTCCGTT | 36.33 | -11.47 | B. pumilus |
| 41 | AAGTCTGAT | 28.56 | -9.93 | P. aeruginosa |

TABLE 3-continued

Listing of Oligonucleotide Probe Sequences. Calculated Tm And ΔG⁰ Values. And Species To Which Each Probe Is Specific (Single Perfect Match)

| Probe | Sequence (5'->3') | Tm (° C.) | ΔG⁰ (Kcal/ mol) | Targeted Species (perfect sequence match with test strains) |
|---|---|---|---|---|
| 42 | AGCTTGATG | 33.72 | -10.88 | - - - |
| 43 | AGTCCGTTG | 38.76 | -11.92 | B. pumilus |
| 44 | AGTCTGATG | 31.34 | -10.38 | P. aeruginosa |
| 45 | GCTTGATGT | 34.54 | -11.04 | - - - |
| 46 | GTCCGTTGT | 39.53 | -12.08 | B. pumilus |
| 47 | GTCTGATGT | 32.18 | -10.54 | P. aeruginosa |
| 48 | CTTGATGTG | 31.25 | -10.25 | - - - |
| 49 | TCCGTTGTG | 39.56 | -12.09 | B. pumilus |
| 50 | TCTGATGTG | 32.22 | -10.55 | - - - |
| 51 | GTGGATACT | 30.35 | -10.21 | P. aeruginosa |
| 52 | AAGCTACTG | 32.18 | -10.55 | P. alcaligenes |
| 53 | AACTACTGA | 27.89 | -9.77 | P. fluorescens, P. veronii |
| 54 | AACTGACTG | 32.75 | -10.64 | P. aeruginosa |
| 55 | AGCTACTGA | 33.22 | -10.85 | P. alcaligenes |
| 56 | ACTACTGAG | 29.78 | -10.05 | P. fluorescens, P. veronii |
| 57 | ACTGACTGA | 33.81 | -10.94 | P. syringae, P. putida |
| 58 | ACTGGCAAG | 39.02 | -11.98 | P. aeruginosa |
| 59 | GCTACTGAG | 34.03 | -10.85 | P. aeruginosa, P. alcaligenes |
| 60 | CTACTGAGC | 34.03 | -10.85 | P. fluorescens, P. veronji |
| 61 | CTGACTGAC | 34.57 | -10.94 | P. syringae, P. putida |
| 62 | CTGGCAAGC | 42.84 | -12.78 | P. aeruginosa, P. alcaligenes |
| 63 | CTACTGAGC | 34.03 | -10.85 | P. fluorescens, P. veronji |
| 64 | CTGACTGAC | 34.57 | -10.94 | - - - |
| 65 | CTGGATGAC | 34.36 | -10.94 | P. fluorescens, P. veronii |
| 66 | GACTGACTA | 29.96 | -10.07 | P. syringae, P. putida |
| 67 | GGCAAGCTA | 38.60 | -11.91 | P. fluorescens, P. veronii |
| 68 | ACTGACTAG | 29.78 | -10.05 | P. syringae, P. putida |
| 69 | GCAAGCTAG | 36.30 | -11.35 | P. aeruginosa, P. alcaligenes |
| 70 | TGAGCTAGA | 32.52 | -10.71 | P. syringae, P. putida |
| 71 | CAAGCTAGA | 31.51 | -10.41 | - - - |
| 72 | CTAGAATGT | 25.55 | -9.21 | P. aeruginosa |
| 73 | GTAGAGGTG | 32.85 | -10.61 | P. aeruginosa |
| 74 | TAGAGGTGG | 34.23 | -11.01 | P. aeruginosa |
| 75 | AGAGGTGGT | 38.26 | -11.87 | P. aeruginosa |
| 76 | GAGGTGGTA | 35.07 | -11.17 | P. aeruginosa |

TABLE 3-continued

Listing of Oligonucleotide Probe Sequences. Calculated
Tm And ΔG°Values. And Species To Which Each
Probe Is Specific (Single Perfect Match)

| Probe | Sequence (5'->3') | Tm (° C.) | ΔG° (Kcal/mol) | Targeted Species (perfect sequence match with test strains) |
|---|---|---|---|---|
| 77 | AGGTGGTAG | 34.92 | -11.15 | P. aeruginosa |
| 78 | GGTGGTAGA | 35.07 | -11.17 | P. aeruginosa |
| 79 | TGGTAGAAT | 27.55 | -9.77 | P. fluorescens |
| 80 | GTGGTGAAG | 35.70 | -11.20 | B. pumilus |
| 81 | CTCTCTGGT | 35.15 | -11.17 | B. pumilus |
| 82 | TCTCTGGTC | 35.30 | -11.19 | B. pumilus |
| 83 | CTCTGGTCT | 35.15 | -11.17 | - - - |
| 84 | TGGACCAAC | 38.01 | -11.76 | P.aeruginosa |
| 85 | ACTGTACTG | 31.36 | -10.36 | - - - |
| 86 | ACCAACATT | 31.39 | -10.50 | P.aeruginosa |
| 87 | CTGTACTGA | 30.68 | -10.22 | - - - |
| 88 | CATTGACAC | 32.10 | -10.41 | - - - |

Probes 1-28 were designed for region A and
probes 29-88 were designed for region B.
Probes designed for species other than the seven test strains are listed as "- - -" in column 5.

Figure 13:
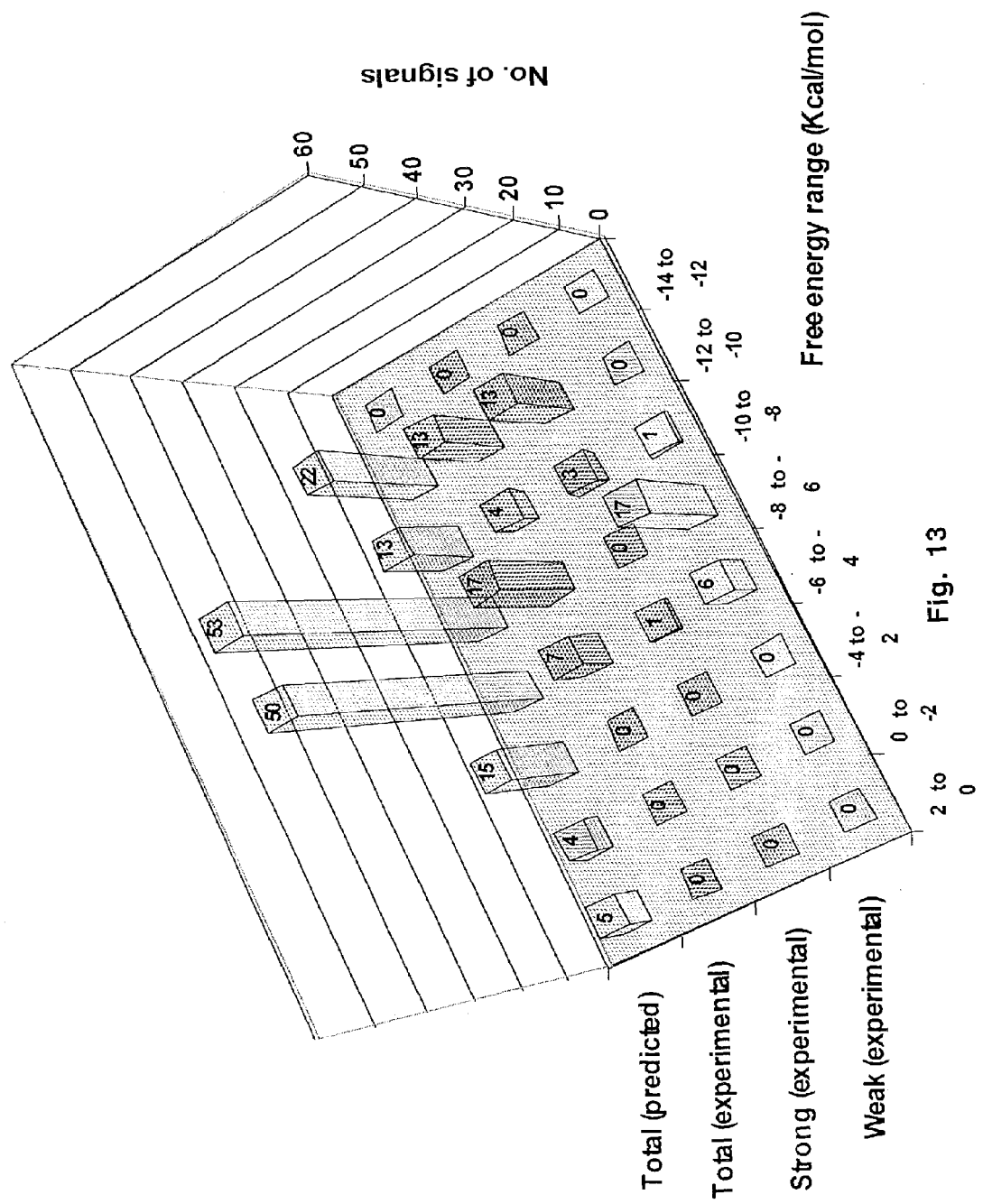
FIG. 13 displays the virtual hybridization results for all 90 9 mer probes in regions "A" for the seven bacteria tested.
Figure 14:
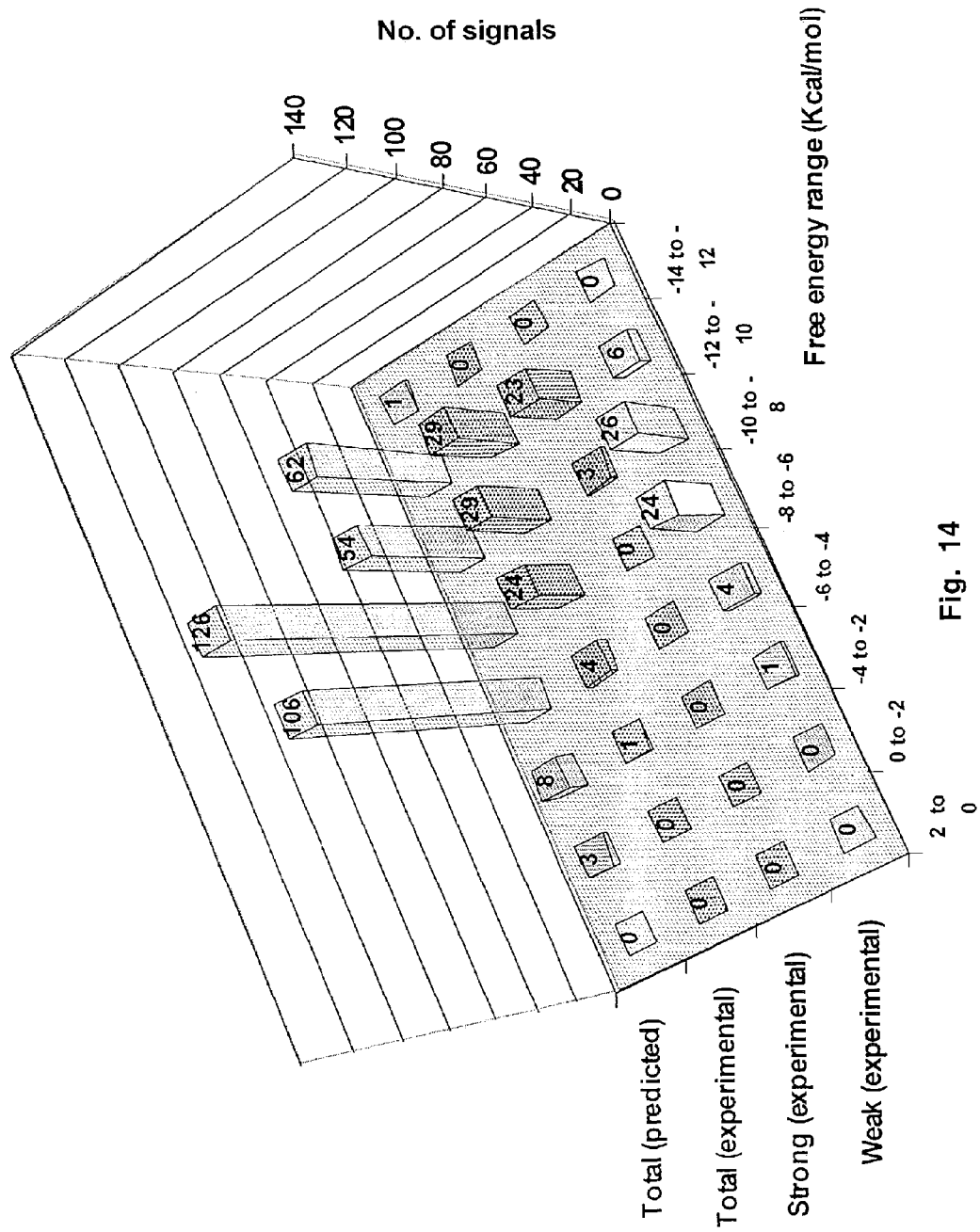
FIG. 14 displays the virtual hybridization results for all 90 9 mer probes in regions "B" for the seven bacteria tested.
Figure 15D:
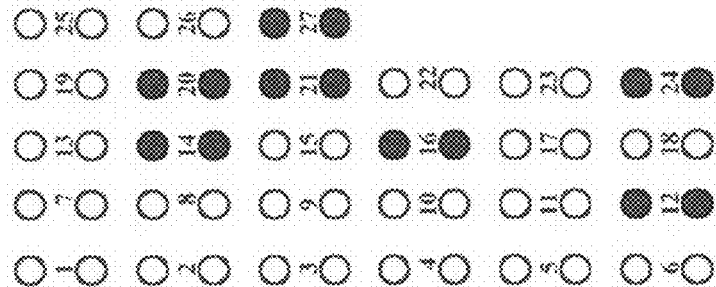
FIGS. 15A-15D display experimental and virtual hybridization patterns for Region A of *Pseudomonas aeruginosa* using oligonucleotide probes designed by the Genosensor Probe Designer program. The probes were spotted in duplicate.
Figure 15C:
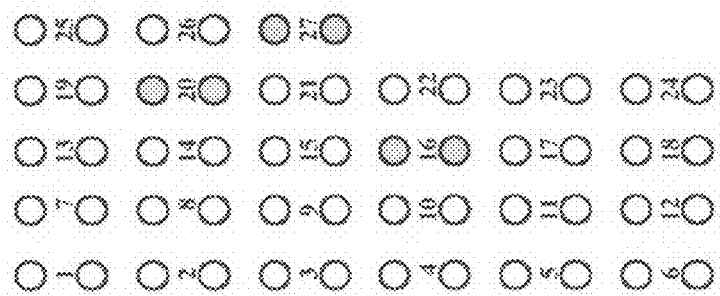
Figure 15B:
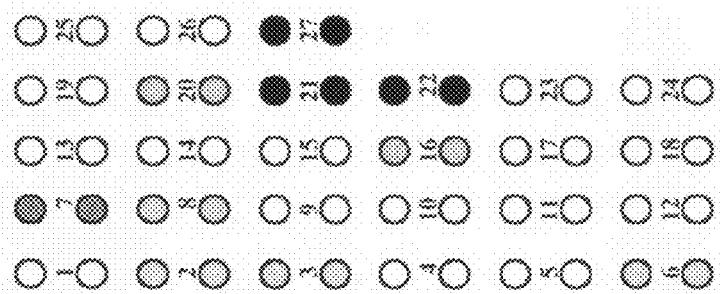
Figure 15A:
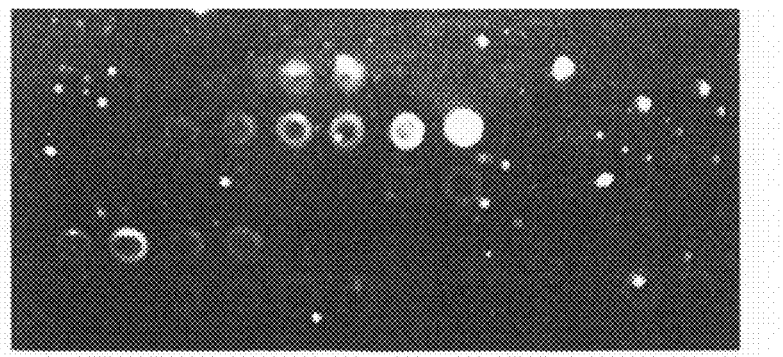

To help explain discrepancies between anticipated and observed hybridization results obtained with the 16S rRNA gene system, the virtual hybridization module of the Genosensor Probe Designer (GPD) software (described further in Example 3) was applied to the data. The virtual hybridization program calculates the Gibbs free energy (ΔG°) of mismatched or matched probes when aligned to target DNA (Table 4). The GPD software runs each probe along the full target DNA sequence (including all test strains) and calculates binding energy as ΔG° for each position. The selection can be adjusted to search for pairings with high, medium or low probability to produce stable hybridization under a given hybridization condition. FIGS. 13 and 14 display the virtual hybridization results for all 90 9 mer probes in regions "A" and "B" for the seven bacteria tested. The results were divided into eight stability groups of increasingly negative ΔG° values (+2 to 0, 0 to -2, -2 to -4, -4 to -6, -6 to -8, -8 to -10, -10 to -12 and -12 to -14 kcal/mol). The green bars in the back row represent the total number of predicted hybridization signals for each stability group, including both perfectly matched and mismatched hybrids. The bars in the remaining rows represent total (blue), strong (red) and weak (yellow) experimentally observed signals. On top of each bar is indicated the total number of signals for all bacterial species that were predicted (green bars) or experimentally observed (other colors) in each stability group. In theory, a Gaussian distribution of predicted ΔG° values (green bars) should be produced for a random collection of probes of a given length. However, in the design of probes, oligonucleotides having single mismatches at any site within the target sequences were generally excluded, and this restriction accounts for the reduced number of hybrids in the stability group with a ΔG° of -8 to -10 kcal/mol. For experimentally detected hybrids it can be seen that the number of signals detected generally decreased as the stability of the hybrid decreased. When the experimentally detected signals were divided into strong and weak signals (red and yellow bars, respectively), it could be seen that for region "A" (FIG. 13), in the group with the highest ΔG° value (-10 to -12 kcal/mol) all signals were strong (100%). In the next stability group (-8 to -10 kcal/mol) most hybridization signals (75%) were strong and the remaining (25%) were weak. In the next group with even lower stability (-6 to -8 kcal/mol) all the signals (100%) were weak. A similar result was seen with the -4 to -6 kcal/mol group, where 85% of the signals were weak and 15% were strong. The same analysis was conducted for region "B" with very similar results (FIG. 14). In general, these results suggest that, with few exceptions, the virtual hybridization analysis explains the perfectly matched and mismatched hybridization signals obtained. Assuming that hybridization signals arise primarily from the most stable duplex structure found for each probe within the target (Table 4), it can be seen that the experimentally detected mismatched hybrids generally contained mismatches positioned at their ends, where destabilization is minimal (Doktycz et al., 1995), and in many of these cases the mismatches were of a type known to have low destabilizing effect (Maldonado-Rodriguez and Beattie, 2001; Peyret et al., 1999; Doktycz et al., 1995; Yang et al., 1997). The good correlation between the experimentally observed hybridization signal intensity and the predicted free energy of binding raises our confidence in the data interpretation. In the case of the relatively small number of pairings with high negative ΔG° value that were not experimentally detected, these may be largely attributed to sequence differences between the samples and reference strains, or to the formation of secondary structure within the target (Matzura and Wennborg, 1996).

Hybridization signals that are observed but not predicted (i.e., involving mismatched hybrids) belong nevertheless to a specific target and consequently, can contribute to the identification of bacterial species via hybridization fingerprinting. As further detailed in Example 3, the hybridization data obtained in the 16S rRNA gene study provided the "working materials" for development of the Virtual Hybridization strategy which is useful in the interpretation of hybridization results, and can guide the selection of optimal sets of oligonucleotide probes for a given genosensor application.

TABLE 4

Comparison of Predicted Versus Experimentally Observed Hybridization In Region B of *P. Aeruginosa*.

| No | Sequence (5'->3') | Tm (° C.)[2] | Δ G° Kcal/mol | Position M.S.S. | Targeted site (3'->5') | Δ G° M.S.S. |
|---|---|---|---|---|---|---|
| 28 | GTACCTAAC | 28.1 | -9.60 | 257 | CCTCGTTTG | -2.54 |
| 29 | GTGGTTCAG | 35.7 | -11.20 | 59 | CACCAAGTC | -11.20 |
| 30 | TGGTTCAGC | 39.1 | -12.00 | 69 | ACCAAGTCG | -12.00 |
| 31 | GGTTCAGCA | 39.1 | -12.00 | 70 | CCAAGTCGT | -12.00 |
| 32 | GTTCAGCAA | 35.2 | -11.16 | 71 | CAAGTCGTT | -11.16 |
| 33 | TTCAGCAAG | 34.4 | -11.00 | 72 | AAGTCGTTC | -11.00 |
| 34 | AGCAAGCTT | 37.7 | -11.77 | 75 | TCGTTCGAA | -11.77 |
| 35 | AGCAAGTTG | 35.1 | -11.14 | 75 | TCGTTGGAA | -7.15 |
| 36 | GCAAGCTTG | 39.0 | -11.94 | 76 | CGTTCGAAC | -11.94 |
| 37 | GCAAGTTGG | 38.0 | -11.70 | 27 | CGTTCGCAA | -5.97 |
| 38 | CAAGCTTGA | 34.4 | -11.00 | 77 | GTTCGAACT | -11.00 |
| 39 | AAGCTTGAT | 31.1 | -10.43 | 78 | TTCGAACTA | -10.43 |
| 40 | AAGTCCGTT | 36.3 | -11.47 | 283 | ATCAGGTCC | -5.86 |
| 41 | AAGTCTGAT | 28.6 | -9.93 | 78 | TTCGAACTA | -4.66 |
| 42 | AGCTTGATG | 33.7 | -10.88 | 79 | TCGAACTAC | -10.88 |
| 43 | AGTCCGTTG | 38.8 | -11.92 | 284 | TCAGGTGCG | -5.86 |
| 44 | AGTCTGATG | 31.3 | -10.38 | 79 | TCGAACTAC | -5.11 |
| 45 | GCTTGATGT | 34.5 | -11.04 | 80 | CGAACTACA | -11.04 |
| 46 | GTCCGTTGT | 39.5 | -12.08 | 161 | AAGGACACA | -4.38 |
| 47 | GTCTGATGT | 32.2 | -10.54 | 80 | CGAACTACA | -7.12 |
| 48 | CTTGATGTG | 31.3 | -10.25 | 81 | GAACTACAC | -10.25 |
| 49 | TCCGTTGTG | 39.6 | -12.09 | 162 | AGGACACAT | -4.38 |
| 50 | TCTGATGTG | 32.2 | -10.55 | 81 | GAACTACAC | -7.97 |
| 51 | GTGGATACT | 30.4 | -10.21 | 103 | CATCTATAT | -4.10 |
| 52 | AAGCTACTG | 32.2 | -10.55 | 124 | TTCGATGAC | -10.55 |
| 53 | AACTACTGA | 27.9 | -9.77 | 125 | TCGATGACT | -7.33 |
| 54 | AACTGACTG | 32.8 | -10.64 | 230 | ATGACTGTG | -6.91 |
| 55 | AGCTACTGA | 33.2 | -10.85 | 125 | TCGATGACT | -10.85 |
| 56 | ACTACTGAG | 29.8 | -10.05 | 126 | CGATCACTC | -6.91 |
| 57 | ACTGACTGA | 33.8 | -10.94 | 231 | TGACTGTGA | -6.91 |
| 58 | ACTGGCAAG | 39.0 | -11.98 | 231 | TGACTGTGA | -6.12 |
| 59 | GCTACTGAG | 34.0 | -10.85 | 126 | CGATGACTC | -10.85 |
| 60 | CTACTGAGC | 34.0 | -10.85 | 127 | GATGACTCG | -10.85 |

TABLE 4-continued

Comparison of Predicted Versus Experimentally Observed Hybridization In Region B of *P. Aeruginosa*.

| No | Sequence (5'->3') | Tm (° C.)[2] | Δ G° Kcal/mol | Position M.S.S. | Targeted site (3'->5') | Δ G° M.S.S. |
|---|---|---|---|---|---|---|
| 61 | TGACTGAGC | 34.6 | -10.94 | 220 | ACATGACTG | -6.91 |
| 62 | CTGGCAAGC | 42.8 | -12.78 | 24 | CTACGTTCG | -8.21 |
| 63 | CTACTGAGC | 34.0 | -10.85 | 122 | GATGACTCG | -10.85 |
| 64 | CTGACTGAC | 34.6 | -10.94 | 228 | ACATGACTG | -4.91 |
| 65 | CTGGATGAC | 34.4 | -10.94 | 233 | GACCTGACA | -5.87 |
| 66 | GACTGACTA | 30.0 | -10.07 | 230 | ATGACTGAG | -6.91 |
| 67 | GGCAAGCTA | 38.6 | -13.91 | 75 | CGTTCGAAC | -9.49 |
| 68 | ACTGACTAG | 29.8 | -10.05 | 231 | ACTCGATCT | -6.91 |
| 69 | GCAAGCTAG | 36.3 | -11.35 | 76 | CGTTCGAAC | -9.49 |
| 70 | TGAGCTAGA | 32.5 | -10.71 | 131 | ACTCGATCT | -10.71 |
| 71 | CAAGCTAGA | 31.5 | -10.41 | 131 | ACTCGATCT | -7.96 |
| 72 | CTAGAATGT | 25.6 | -9.21 | 154 | CATCTTAAA | -5.04 |
| 73 | GTAGAGGTG | 32.9 | -10.61 | 145 | CATCTCCAC | -10.41 |
| 74 | TAGAGGTGG | 34.2 | -12.03 | 144 | ATCTCCACC | -11.01 |
| 75 | AGAGGTGGT | 38.3 | -11.97 | 147 | TCTCCACCA | -11.47 |
| 76 | GAGGTGGTA | 35.1 | -11.17 | 148 | CTCCACCAT | -11.17 |
| 77 | AGGTGGTAG | 34.9 | -11.15 | 149 | TCCACCATC | -11.15 |
| 78 | GGTGGTAGA | 35.1 | -11.17 | 150 | CCACCATCT | -11.17 |
| 79 | TGGTAGAAT | 27.6 | -9.77 | 152 | ACCATCTTA | -9.77 |
| 80 | GTGGTGAAG | 35.7 | -11.20 | 205 | CACCCCTTC | -9.41 |
| 81 | CTCTCTGGT | 35.2 | -11.27 | 275 | ATGGGACCA | -6.31 |
| 82 | TCTCTGGTC | 35.3 | -11.10 | 274 | TGTGACCAT | -6.21 |
| 83 | CTCTGGTCT | 35.2 | -11.17 | 277 | GCGACCATC | -6.31 |
| 84 | TGGACCAAC | 38.0 | -11.76 | 214 | GACTGGTCG | -4.53 |
| 85 | ACTGTACTG | 31.4 | -10.36 | 226 | TGACATGAC | -10.36 |
| 86 | ACCAACATT | 31.4 | -10.30 | 198 | TTGTGGTCA | -3.30 |
| 87 | CTGTACTGA | 30.7 | -10.22 | 227 | GACATGACT | -10.22 |
| 88 | CATTGACAC | 32.1 | -10.41 | 290 | ATGACTGTG | -6.26 |

The first column shows the 9 mer probe number as given in Table 3. The second column displays the 9 mer probe sequence (5'->3' direction). The third column lists the calculated Tm values for each 9 mer probe, paired with its complementary target sequence. The fourth column lists the binding energy (ΔG° in Kcal/mol) calculated for each probe, paired with its complementary target sequence. The fifth column lists the first nucleotide position of the most stable site (MSS) for binding of each probe within region B of *P. aeruginosa*. The sixth column displays the target sequence (3'->5' direction) for each MSS within region B of *P. aeruginosa*, with paired positions written in black and mispaired positions indicated in orange. The last (seventh) column lists the calculated binding energy (ΔG° in Kcal/mol) for hybridization of each probe at its MSS within region B of *P. aeruginosa*.

EXAMPLE 3

Virtual Hybridization

Using virtual hybridization (VH) analysis rules as described earlier, the set of selected 16S rRNA gene probes and target sequences were analyzed to predict virtual hybridization patterns. Table 5 represents the predicted and experimentally observed hybridization signals obtained in all of these experiments, grouped according to predicted free energy of probe-target hybrids. FIG. 15 shows a comparison of predicted and experimental hybridization patterns in a representative experiment.

TABLE 5

Occurrence of Potential Hybridization Sites, Experimental Hybridization Signals, And Probability of Hybridization As A Function of Predicted Free Energy Range.

| ΔG range | # of sites predicted | # of sites with perfect match | Strong experimental signals (S) | Weak experimental signals (W) | Total experimental signals (S + W) | Probability of hybridization |
|---|---|---|---|---|---|---|
| 0 to +2 | 5 | 0 | 0 | 0 | 0 | 0.00 |
| −2 to 0 | 7 | 0 | 0 | 0 | 0 | 0.00 |
| −4 to −2 | 23 | 0 | 0 | 1 | 1 | 0.04 |
| −6 to −4 | 156 | 0 | 1 | 10 | 11 | 0.07 |
| −8 to −6 | 179 | 0 | 0 | 41 | 41 | 0.23 |
| −10 to −8 | 67 | 8 | 6 | 27 | 33 | 0.49 |
| −12 to −10 | 84 | 82 | 36 | 6 | 42 | 0.50 |
| −14 to −12 | 1 | 1 | 0 | 0 | 0 | 0.00 |
| Total = | 522 | 91 | 43 | 85 | 128 | — |

Predicted free energy values for potential hybridization sites were compared with experimentally obtained hybridization signals in order to select idealized parameters for reliable virtual hybridization. These comparisons revealed that predictions of the hybridization of 9 mer probes could be made with the highest degree of accuracy using the set of parameters listed in Table 6. Moreover, it appears that the prediction of hybridization based on the evaluation of the number of contiguously paired bases and thermal stability of the bases involved in the hybridization could be sufficient for designing genosensor chips with the greatest capacity to manifest the desired characteristics of the analyzed sequences.

TABLE 6

Improved Parameters For Selecting Probes (9-Mer Length) By Virtual Hybridization

| Parameter | value |
|---|---|
| Minimal number of complementary bases (minbasescom) (nt) | 6 |
| Minimal size of block with contiguously paired bases (minblocksize) (nt) | 5 |
| First ΔG cut-off value (Gcutoff1) (Kcal/mol) | −10 |
| Second ΔG cut-off value (Gcutoff2) (Kcal/mol) | −8 |

Similar experiments can be readily performed to derive suitable parameters for Virtual Hybridization analysis of probes shorter and longer than 9 mer. An important feature of Virtual Hybridization analysis provided within the Genosensor Probe Designer software is that the program can accommodate future expansion of knowledge concerning the thermodynamics of unusual nucleic acid interactions. For example, as additional information becomes available on the free energy contributions of mismatched base pairs and secondary or tertiary structures, the new thermodynamic data sets can be directly used in the existing Virtual Hybridization software to provide a still more comprehensive and reliable prediction of hybridization patterns.

From the analysis of the VH results it can be seen that about 50% of the potential hybridization sites (perfect or ambiguous) with free energy range between −12 and −10 Kcal/mol yielded detectable experimental signal (strong signals for the most part). A similar situation existed for potential sites with free energy range between −10 and −8 Kcal/mol, where 49% of the sites gave experimental signal, but this time the proportion of weak signals was higher than the strong ones. This situation changes considerably for the free energy range of −8 to −6 Kcal/mol, where only 23% of the sites gave experimental signal (all weak signals). For weaker free energy ranges (above −6 Kcal/mol) the relative number of experimental signals with respect to the number of potential hybridization sites was even lower.

A Kolmogorov-Smirnov normality test showed that the distributions of free energy values for the potential hybridization sites and for the sum of weak and strong signals, differ considerably from the normality. However, strong and weak signals assume a normal distribution. In order to demonstrate if calculated free energy values for "strong" and "weak" experimental signals were significantly lower (more stable) than the free energy distribution for all potential hybridizations sites, we perform both parametric and nonparametric tests for all cases.

Statistical tests showed that free energies for strong signals differ considerably from the free energies for all potential hybridization sites for both PCR products. Free energies for weak signals at the PCR products for region A are not significantly different to the free energies for all potential hybridization sites, but the difference is significantly for PCR products for region B and also when we combine the results for both regions. In conclusion, this analysis showed that strong hybridization signals were significantly obtained at more negative free energies (more stable) while weak signals are usually found at negative free energies too, but the discrimination power between them and the energies for all potential sites is considerably lower than that for strong signals. Moreover, it can be seen that both signals as a whole are significantly present at more negative free energies.

Figure 16:
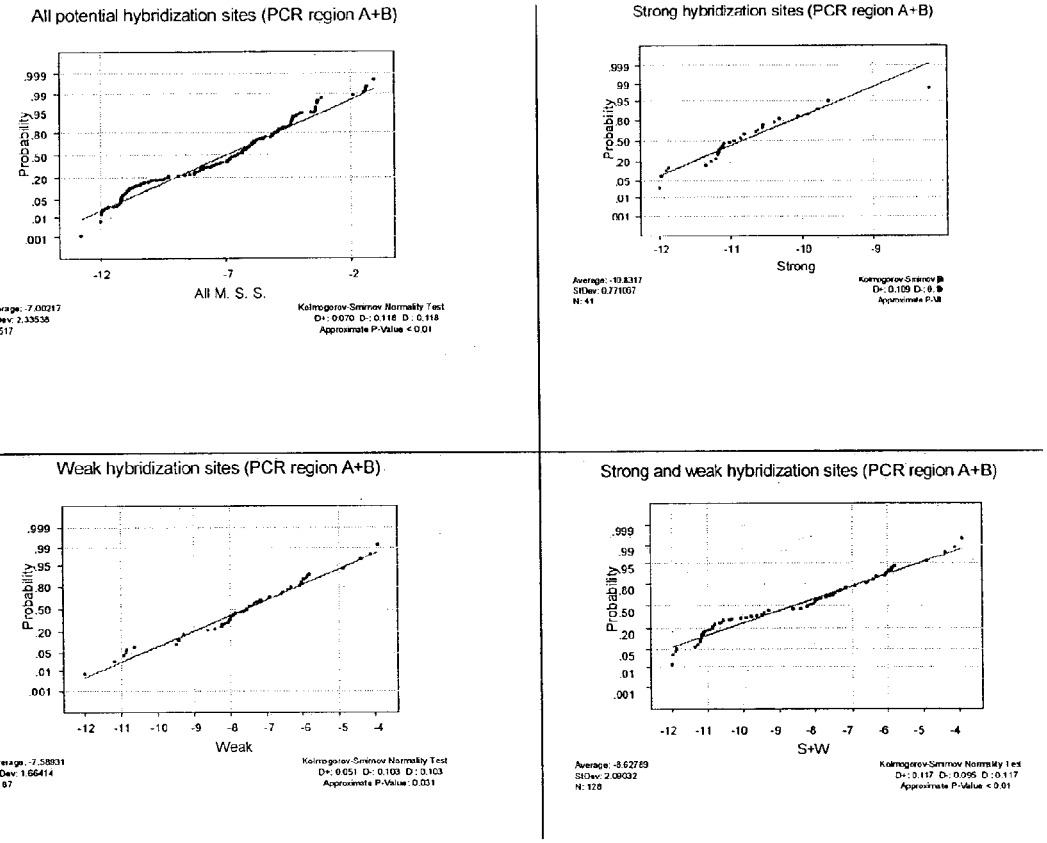
FIG. 16 displays the results of Kolmogorov-Smirnov normality test for distribution of calculated free energy values for all sites of potential hybridization and sites exhibiting strong experimental hybridization signals, sites of weak signal, and combined sites of strong+weak hybridization signals.

The results of statistical analyses for Regions A+B are shown in Table 7 and FIG. 16.

TABLE 7

Statistical Analyses of Virtual And Experimental Hybridization In Regions A + B.

| | Kolmogorov-Smirnov normality test for distribution of predicted free energies | | | | |
|---|---|---|---|---|---|
| Sites | n | Mean | Median | StDv. | p-value |
| All M.S.S. | 517 | −7.002 | −6.530 | 2.335 | <0.01 |
| Strong signals | 41 | −10.832 | −10.940 | 0.771 | >0.1;normal5 |

TABLE 7-continued

Statistical Analyses of Virtual And Experimental Hybridization In Regions A + B.

| Weak signals | 87 | −7.589 | −7.540 | 1.664 | 0.031 |
| Strong + weak | 128 | −8.628 | −8.220 | 2.090 | <0.01 | n = number of sites; StDv = Standard deviation; M.S.S. = most stable sites.

Calculated p-values for Mann-Whitney and 2-Sample t-test for comparison of predicted free energies

| Comparison | Man-Whitney | 2-Sample t-test |
|---|---|---|
| All M.S.S. vs strong signals | 0.0000 | 0.000 |
| All M.S.S. vs weak signals | 0.0011 | 0.005 |
| All M.S.S. vs strong + weak | 0.0000 | 0.000 |

M.S.S. = most stable sites.

It can be seen from the above Virtual Hybridization results that some probes that were predicted to hybridize perfectly or ambiguously by the VH analysis at stable ΔG ranges failed to yield experimental hybridization signals. For example, for region A of *P. aeruginosa* probes 12 and 14 were predicted to yield hybridization signals, however these signals were not observed. Some possible explanations of this phenomenon include:

(i) UNCERTAINTY OF TARGET SEQUENCES. Genbank reference sequences used to design the probes (cited in Example 2) may be different from the actual PCR product sequences derived from the environmentally isolated test strains. Thus, differences between experimental and virtual hybridization patterns (including both unexpected and unobserved signals) could be due to differences between reference and actual target sequences.

(ii) SECONDARY STRUCTURE OF THE PRODUCT. Hybridization reactions were carried out at low temperature which favors the formation of secondary structure within the target molecule. A simplified evaluation of the secondary structure of the target is provided within the Genosensor Probe Designer program. Self-complementary sections of the target molecules longer than a given value are searched for and listed. If target sites of the probes overlap with sections with potential secondary structure, these probes could have lower probability of yielding hybridization signals. Results in this case are somewhat equivocal, but they suggest than the absence of some hybridization signals could be due to the secondary structure of the target molecule.

Figure 17:
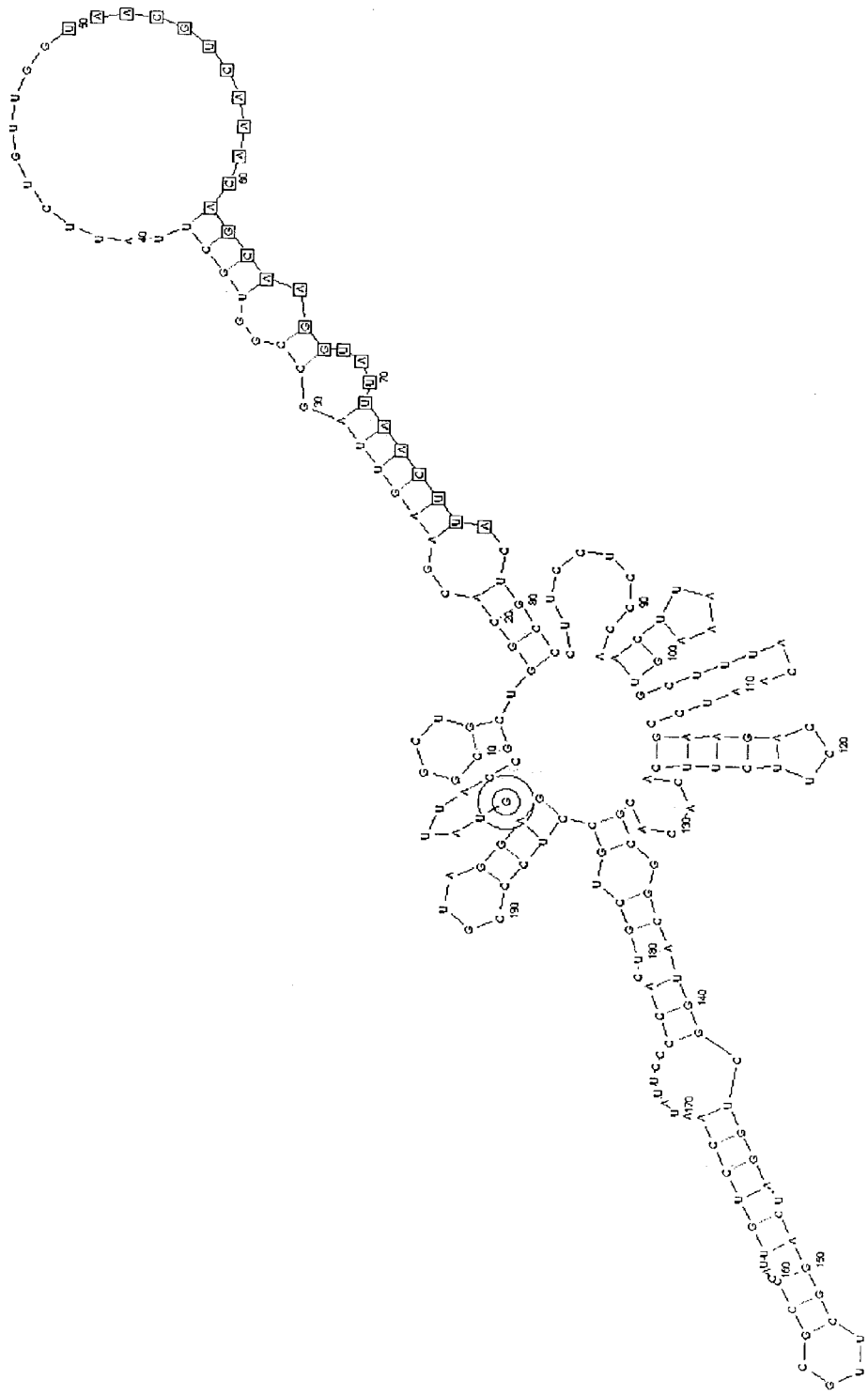
FIG. 17 shows secondary structure of region A of 16 s ribosomal RNA gene from *P. aerugionosa* (SEQ ID NO: 119) predicted with RNA draw v1.1. All GU pairs were forbidden. Regions correspond to important targeted sites for probes have bases marked with squares.
Figure 19:
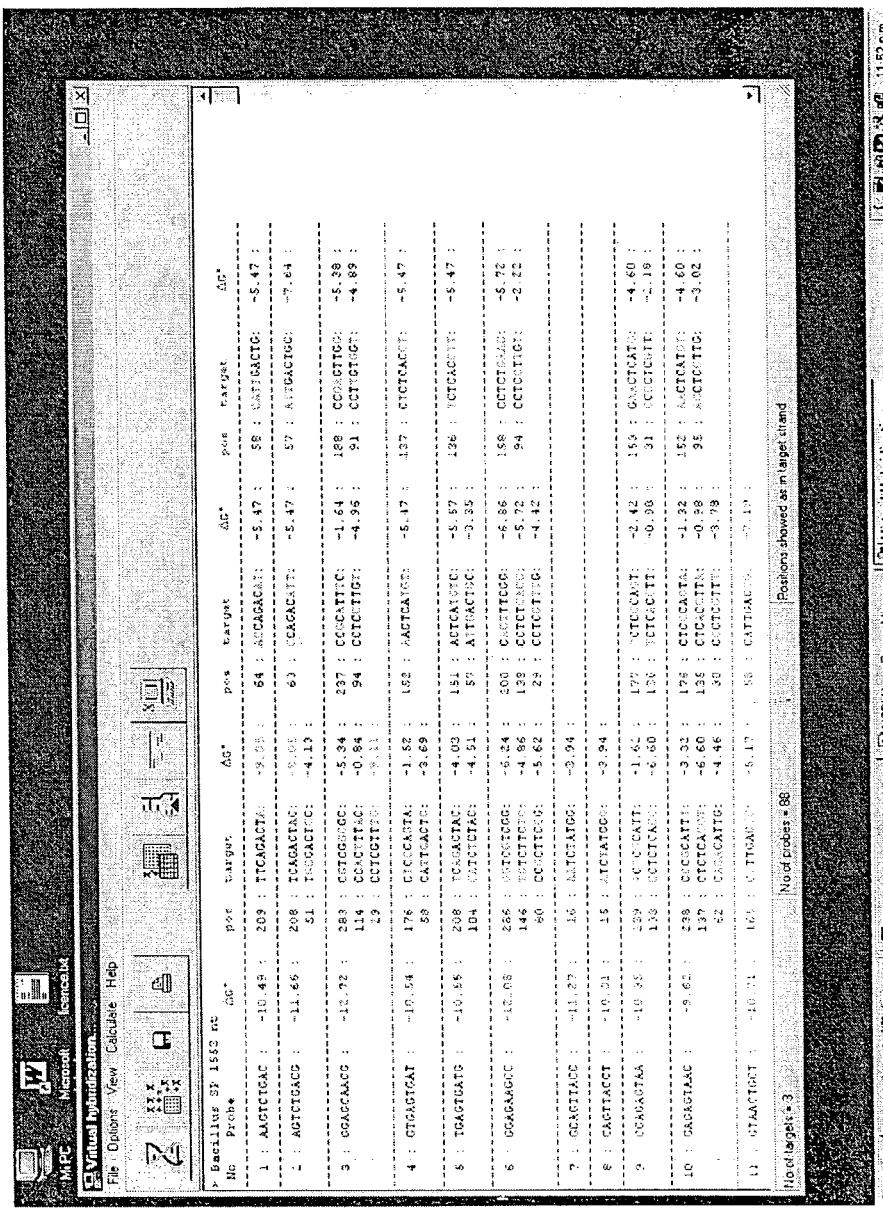
FIG. 19 shows Virtual Hybridization program running in the Windows Millenium Desktop. The program has an advanced user interface which is menu driven. Here is shown a part of an analysis of potential hybridization between several probes (SEQ ID NOS: 31-42) and a *Bacillus* target sequence (SEQ ID NOS: 122-157). Potential Hybridization sites are shown with their associated free energy values. Gray is used to show sites with free energy lower than specific cut-off values.
Figure 20:
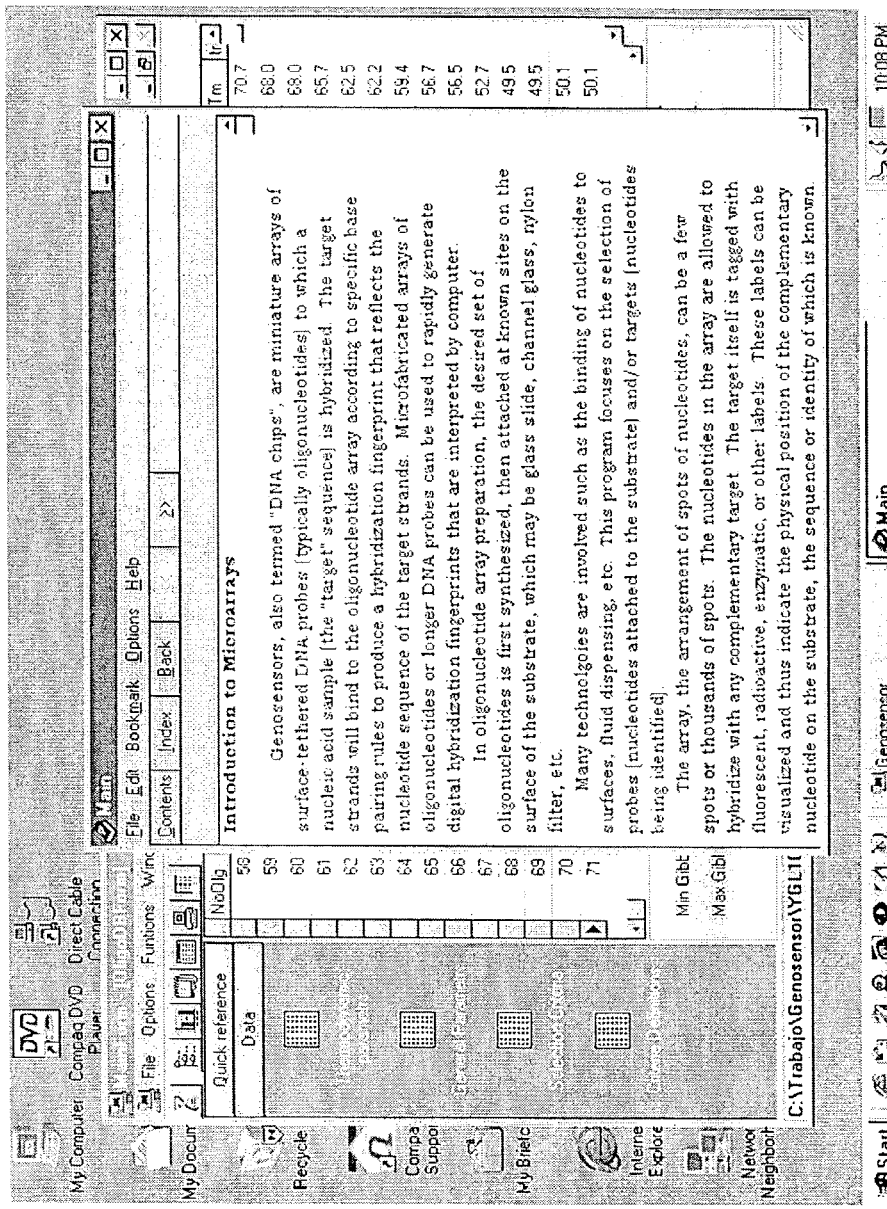
FIG. 20 shows the Help system of the Genosensor Probe Designer Program. The GPD program has a complex help system which describes each of the functions implemented in the program.
Figure 21:
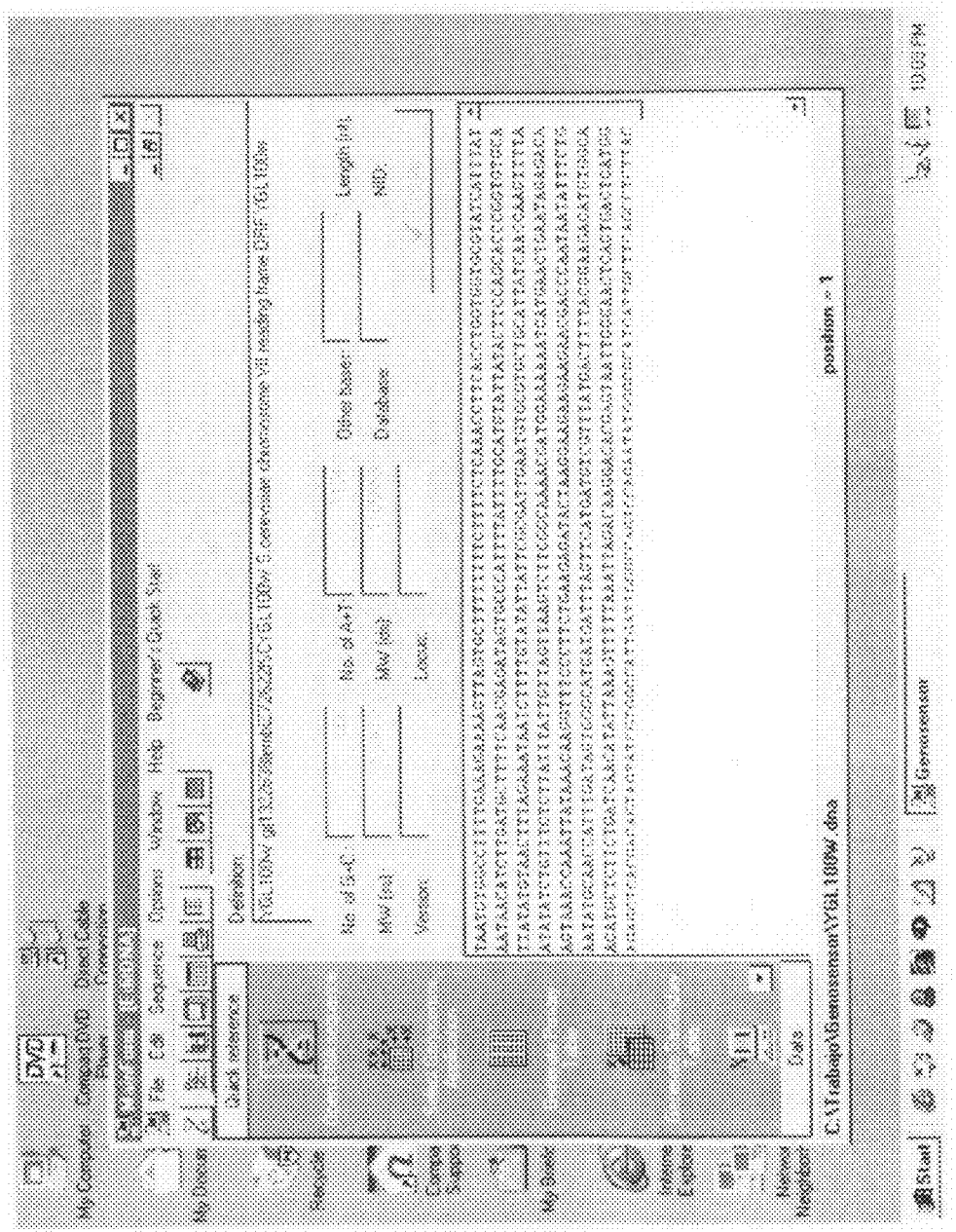
FIG. 21 shows the Sequence editor in the Genosensor Probe Designer Program. DNA sequences, e.g., SEQ ID NO: 158, can be edited directly from the GPD program in order to obtain the complementary sequence, cut, or copy sections of the sequence, search PCR products, etc.
Figure 22:
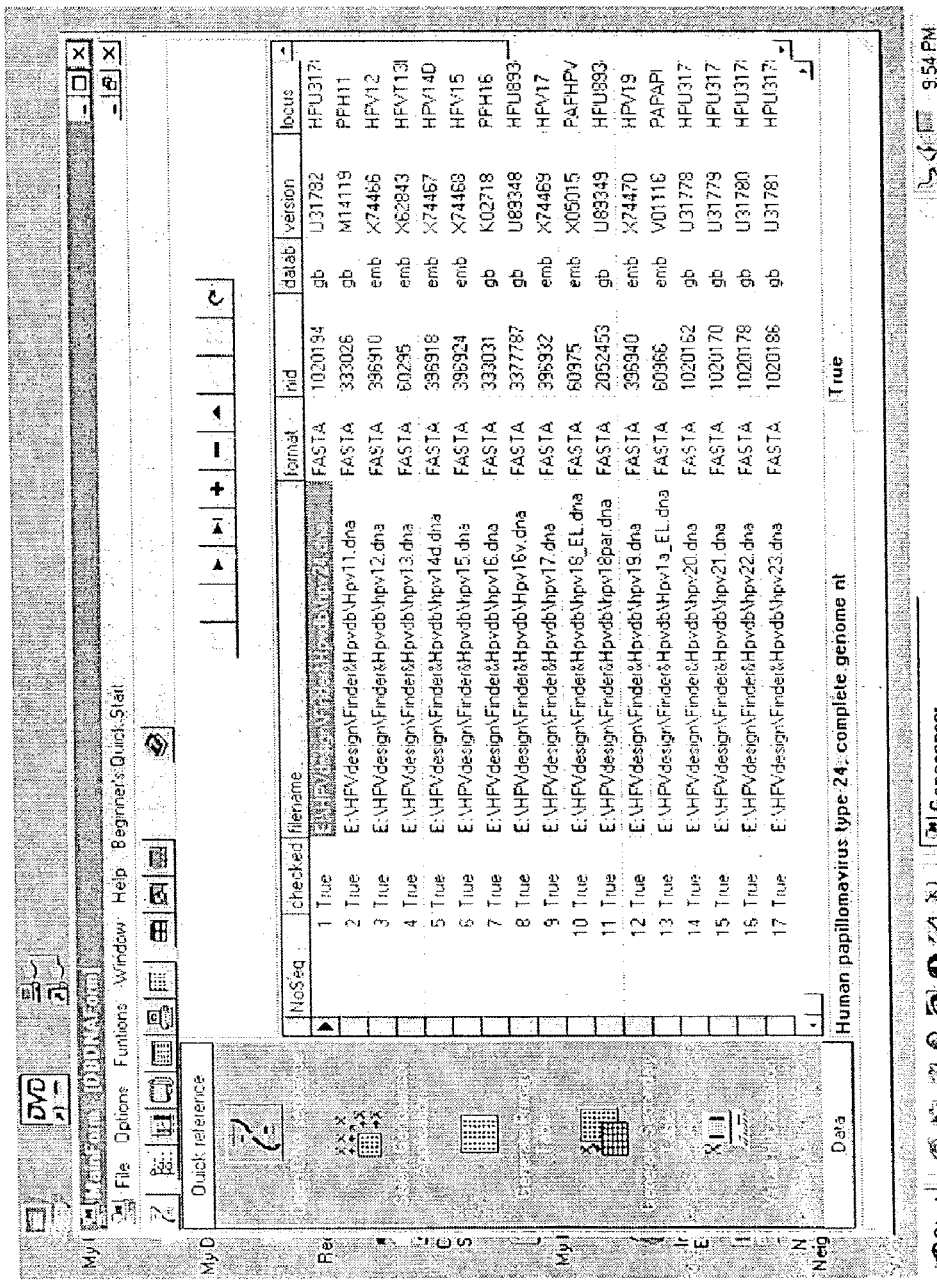
FIG. 22 shows the Databases in the Genosensor Probe Designer Program. The GPD program has database capabilities to organize DNA sequence data and selected probes.
Figure 23:
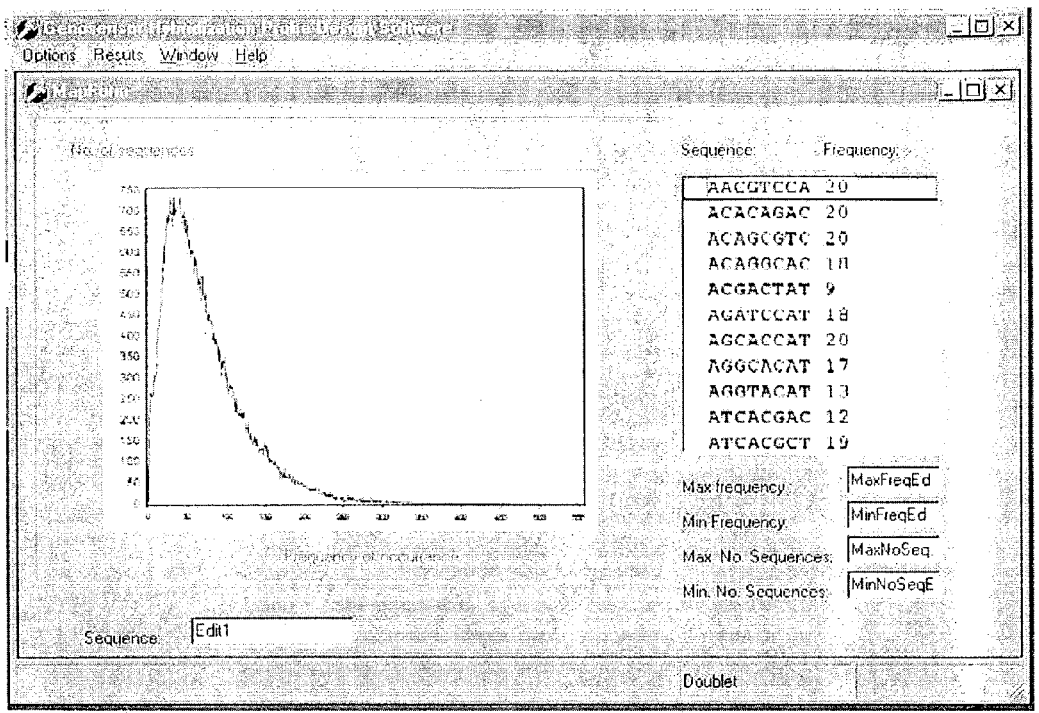
FIG. 23 shows an example of mapping of probes in the genome of an organism using the Genosensor Probe Designer Program. The program uses a very fast algorithm in order to find all the probes of a given size which are present in the genome sequence of a specific organism or database. The program can then produce a graph listing the number of probes that appear at different frequencies in that sequence or database. The program can show all the possible probes found and their frequencies.
Figure 24:
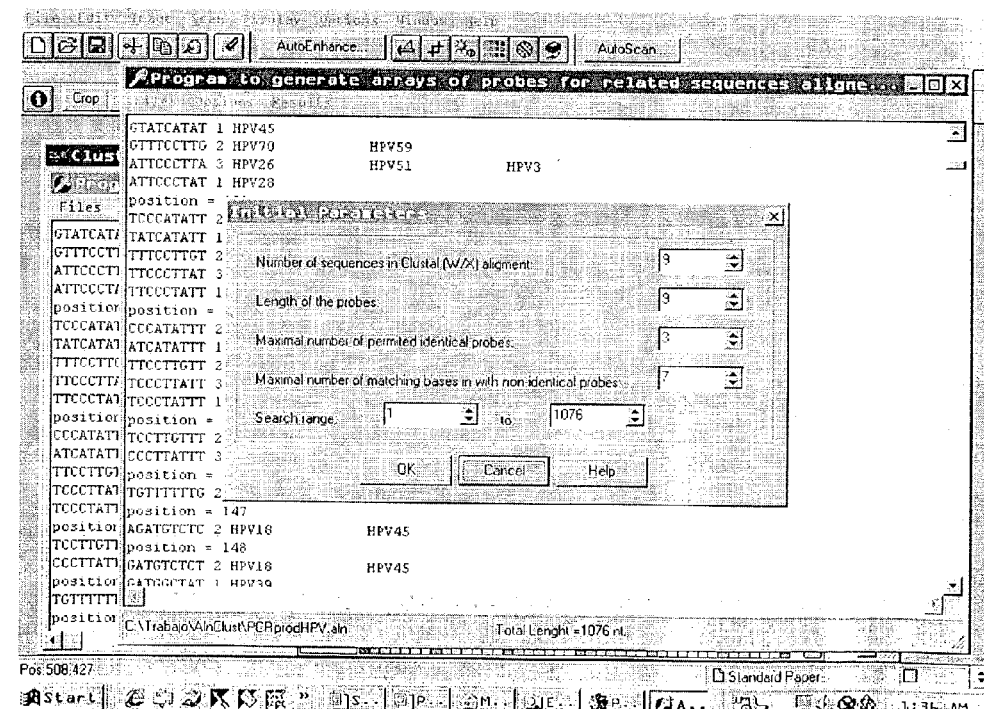
FIG. 24 displays search of probes from aligned sequences in the Genosensor Probe Designer Program. Sequences can be aligned with the help of any alignment tool such as Clustal W. The program scans the alignment column by column in order to find the most variable (or conserved) regions which will then be used to design specific (or universal) probes.

Secondary structure within the 16S rRNA gene sequences was further evaluated with the help of the program RNA draw v1.1. Since this program was designed to predict secondary structure of RNA sequences, the prediction will be just an approximation for DNA targets. In order to provide a closer prediction of the secondary structure of the DNA target, G-U pairs (common in RNA molecules) were forbidden (G-T pair are uncommon in DNA). For PCR product A of *P. aerugionosa*, an interesting region which includes bases 50 through 77 contains the targeted sites for probes 12, 14, 16, 20 and 27. As seen in FIG. 17, the complete sequence of probes 12, 14 and part of the sequence of probes 16 and 20 are positioned within a region capable of forming stable secondary structure. Probe 27, which yielded a hybridization signal, is positioned outside of this region. Although predicted secondary structures do not satisfactorily explain all the cases of missing hybridization signals, they may explain the absence of some predicted hybridization signals, especially since hybridization reactions were carried out at low temperatures.

EXAMPLE 4

Source Code of Genosensor Probe Designer Program and Associated Materials

The source code of the Genosensor Probe Designer Program, together with associated data and documents are provided in the computer program listings appendix.

The source code include: (1) the source code for the main Genosensor Probe Designer program; (2) the source code for objects and other tools used for representing DNA molecules, interactions and selection criteria; (3) the source code for dialog boxes that art part of the GPD program interface; (4) data files containing thermodynamic properties used by the GPD program; and (5) documents and Microsoft help projects for building the Help system of the GPD program.

The Genosensor Probe Designer Program is further described in the following Table 8, which includes a description of program units contained in the main GPD program.

TABLE 8

Description of Units for the Main GPD Program

| Pascal Unit (*.pas) | Delphi Form (*.DFM) | Type | Description |
|---|---|---|---|
| AboutBx | AboutBox | Dialog | Shows a Dialog box with the name of the program, version and credits. |
| AddProbe | AddProbeDlg | Dialog | Shows a dialog box where an oligonucletide sequence and properties can be introduced and added to a database. |
| Catch.pas | | Main interface | Unit to collect important information about data from the Genosensor Software as maximum and minimum thermodynamic values. |
| Combine | | Library | This unit contains procedures and functions for calculating all the possible combinations of sequences that can be obtained from a sequence with ambiguous bases. |

TABLE 8-continued

Description of Units for the Main GPD Program

| Pascal Unit (*.pas) | Delphi Form (*.DFM) | Type | Description |
|---|---|---|---|
| CritProDlg | CriteriaPropDlg | Dialog | Shows a dialog box where the values of the Criteria parameters used for probe selection can be visualized and edited. |
| CritDlg | CriteriaDlg | Dialog | Dialog box which permits the user to enable or disable the criteria parameters used for probe selection. |
| CriteriaSel | | Library | Contains the source code for the TCriteria class which contains all the information required to select or reject a potential probe except similarity data. The TCriteria object has specialized properties describing whether a particular property is active and its minimal and maximal values. Methods were implemented to verify whether a particular oligonucleotide property is between the minimum and maximum values. |
| DBDNAWin | DBDNAForm | Main interface | Displays a Form in which information about the DNA internal database is shown. |
| Destiny | ProbeDestDlg | Dialog | Displays a dialog box in which the destination of a probe (primary or secondary table) can be specified. |
| DNAclass | | Library | Contains the source code for the TDnaclass class and descendents for the object representating and manipulating long DNA sequences. |
| DNAoligo | | Library | Contains the source code for the TDNAoligo class and its descendents. These are combined classes obtained from TDNAclass and Toligoclass and are used to simulate the hybridization between long and short DNA sequences, and implements also several tools to compare both kinds of sequences |
| EdDNA | EditDNA | Main interface | Shows a form in which a DNA sequence from the internal DNA database can be edited. The editor implements traditional edit capabilities such as Cut, Paste, Delete and Select as well as several search capabilities specialized for DNA sequences (they permit, for example, the use of characters for representing ambiguous bases). The editor also contains some useful tools for obtaining the complementary sequence, or for modifying names. |
| FieldsDlg | VisibleFieldsDlg | Dialog | Shows a dialog box where the visible fields of the oligonucleotide database can be selected. This selection does not affect the structure of the database itself. |
| Formats | | Library | This unit contains procedures and functions for manipulation of DNA |

TABLE 8-continued

Description of Units for the Main GPD Program

| Pascal Unit (*.pas) | Delphi Form (*.DFM) | Type | Description |
|---|---|---|---|
| | | | sequence, especially for Format conversions (Genbank to FASTA). |
| GotoDl | GotoDlg | Dialog | Shows a dialog box which permits the user to jump to a desired position of the DNA sequence that is edited in the EditDNA window. |
| Graph2D | | Library | Contains the source code for the TgraphicXY class which is used to create a XY coordinate system. |
| Import | ImportDlg | Dialog | Shows a dialog box in which the user specifies the data contained in a text file for an oligonucleotide sequence that will be imported to the GPD program (Data can include the name of the sequence, the sequence, and concentrations of probe and salt. |
| Main | MainForm | Main interface | This is the main unit of the GPD program. It administrates the main form of the application and main menus. From this unit all Dialog boxes and Libraries are called and controlled throughout the entire design procedure. |
| OlgClass | | Library | Implements source code for the TOligoclass and its descendents used to represent and manipulate oligonucleotide sequences and their properties. |
| OlgDlg | OligoDlg | Dialog | Displays a Dialog box where an oligonucleotide sequence, derived from a specific position within a DNA sequence placed in the Editor Window, can be shown. This Dialog is used to see the thermidynamic properties of a single probe and also for manual selection of probes (probes can be sent to the primary or secondary tables from this dialog box). |
| OligoFrm | OligoDBForm | Main interface | Shows information about probes contained in the primary and secondary tables. It shows the final sequences of probes resulting from the design procedures. |
| OOPList | | Library | Object-oriented implementation of a singly linked list. Methods are included for creating the list, inserting data, deleting elements, counting the number of elements and disposing of the list. Code is based on example 5.3 from S. Sengputa and C. P. Korobkin, C++ Object-Oriented Data Structures (119994), pp: 145–156, but the code impemented here is in Delphi and avoids recursive calls. |
| Params | SimilParamsDlg | Dialog | Displays a dialog box where the parameter values for similarity searches can be shown and modified. |

TABLE 8-continued

Description of Units for the Main GPD Program

| Pascal Unit (*.pas) | Delphi Form (*.DFM) | Type | Description |
|---|---|---|---|
| PCRdlg | PCRsearchDlg | Dialog | Displays a dialog box used for the sequence editor where a pair of short sequences can be introduced in order to test whether a subsequence exists within the edited DNA sequence which is delimited by such pair of sequences. This unit is useful for finding PCR products. |
| Prjclass | | Library | Implements the source code of the Projects created for the GPD program. A project is a file that tracks all tables, properties and criteria used for the design procedure of probes. |
| ProjDlg | ProjectDlg | Dialog | Shows a dialog box where the properties of the design project can be specified or modified. |
| RichFmt | | Library | This unit has routines for writing documents in the Rich Text Format (RTF). Routines are based on the RTF Specification Version 1.3 (119994). All the RTF routines are encapsulated in the class TRichroutines. When an instance of TRichroutines is created an RTF file is produced. The RTF file is closed and saved into the disk when the instance is destroyed. |
| Rtfcolor | | Library | Contains values of the constants defined for RGB colors used in Rich Text Format Documents. |
| SearchB | SearchDlg | Dialog | Dialog box called for the Edit DNA windows to search for a particular short sequence within a DNA sequence. The short sequence can include characters for representing ambiguous bases. |
| SelApp | SelAppDlg | Dialog | This dialog box permits the user to specify the application to which the designed probes will be destined. |
| Simil | | Library | This unit contains the source code for Tsimilarityclass which holds functions and procedures for the similarity search in. It also implements functions for showing a detailed description of similarity between oligonucleotides and DNA sequences. |
| SimilDlg | SearchSimilarityDlg | Dialog | Dialog box called within the Edit DNA windows to search for a particular short sequence within a DNA sequence. This search reveals detailed information about the similarity degree between the probe and the specific DNA sequence. |
| SimResDlg | SimilResDlg | Dialog | Hidden Dialog box used only for testing some programming issues. It shows probes selected at any stage of the |

TABLE 8-continued

Description of Units for the Main GPD Program

| Pascal Unit (*.pas) | Delphi Form (*.DFM) | Type | Description |
|---|---|---|---|
| | | | design and is not available for the user. |
| SqModule | DataModule1 | Main interface | Datamodule for the GPD program. This module administrates the use of all the tables in different points of the program (DNA internal databases, primary and secondary tables). |
| Tables | | Library | Contains definition of all tables used in the GPD program and auxiliary procedures to create the tables and to insert data into them. |
| TablesDlg | TablesDialog | Dialog | This dialog box shows a list of all the available tables which have been created in a design project. The user can combine created tables to construct a query. |
| Tools | | Library | This unit contains procedures and functions for routines of miscellaneous and general use. |
| VHclass | | Library | Contains the source code for the Tvirtualhybridiza-tion class, which is used to predict hybridization patterns. |
| VHConf | VHDLG | Dialog | This dialog box shows parameters for configuration of the VH analysis. |
| VH_form | VHForm | Main interface | Form for showing the results of the VH analysis. |

EXAMPLE 5

Source Code of Accessory Programs

A number of accessory programs that extend the application of the Genosensor Probe Designer (GPD) software are also provided in the computer program listings appendix. The listed source codes include:

(1) The source code of the program Virtual Hyb. This program performs the Virtual Hybridization analysis independent of the GPD program (within which this function is also incorporated) and has some limited capabilites for manipulating files.

(2) The source code of a program called AlnClustal. This program is used to select "specific" or "universal" probes from a Clustal alignment of sequences.

(3) The source code of the program BuiltDB. This program is used to build a FASTA library of sequences (One file containing multiple sequences in FASTA format).

(4) The source code of a program called Genbank, which converts sequences from the Genbank format into the FASTA format.

(5) The source code of the program ProbesHom. This is an auxiliary application useful for evaluation of the similarity between multiple probes or primers and single or multiple DNA sequences. It implements a search algorithm which is similar to that used in the VH program, looking for sites with a number of total similar bases or with a block of contiguous similar bases.

(6) The source code of a program called Structure Windows. This is a program to a simplify evaluation of secondary structure of targets. This program simply locates zones inside of a target molecule that can be self-paired and calculates their free energy value. The program uses an algorithm similar to "build a dot graph," wherein the DNA sequence is placed on X and Y axes. Coordinates X,Y represent the potential pairing of the Base number X with the base number Y. If these two bases can be paired, a dot is placed in such coordinate. In a graph such as this, diagonals represent zones of the DNA molecules that can be self-paired. This program does not currently show the dot graph but it shows all the sequences in the diagonals.

(7) The source code of the program Tandem. Tandem is a program that selects sets of probes for the tandem hybridization approach including a capture probe and a stacking probe. This program may be readily modified to accommodate updated information on the thermodynamic properties of tandem hybridization.

(8) The source code of a program named AdjustLen. This program modifies the length of a set of probes in order to obtain a set probes with decreased Tm variation. The basic GPD program generates probes with the same length and a similar stability. However, stability criteria can be disabled in a GPD session, then the probes can be modified on their length using AdjustLen until their stability approaches a defined Tm value. The algorithm used in AdjustLen adds nucleotides to 3' or 5' end, then calculates Tm. Deletion of bases is not currently implemented, so after the AdjustLen program runs the probes will have the same or longer length.

(9) The source code of a program called MapSeq. This program uses a very fast algorithm to build a "map" of all possible sequences of a given size found within a given DNA sequence.

(10) The source code of a program named Stability. This program shows graphically the calculation of thermal stability for perfect and mismatched hybrids. Free energy calculations use the same algorithm implemented in the VH algorithm. This function can be conveniently used for fast visualization of energetic contributions in the hybridization between any given pair of strands, as illustrated in the screen image of FIG. 18.

The Genosensor Probe Design software system is further described in the following Table 9, which includes descriptions of program units contained in the GPD accessory programs.

TABLE 9

Description of Other Units Included in Auxiliary Applications for the GPD Program

| Pascal Unit (*.pas) | Delphi Form (*.DFM) | Type | Description |
|---|---|---|---|
| | | AdjustLen | |
| MainForm | Form1 | Main interface | Main Window of the Adjust Len program |
| Analysis | | Library | This unit implements procedures to adjust the length of probes in order to obtain a set o probes with similar stability but different length. The unit uses the DNA sequences located on both sides of the region within the DNA sequence from which the probe was derived. The program adds a nucleotide to one or other side, each time locating first the nucleotide that gives the minimal Tm contribution. The nucleotide addition is continued until the Tm values reaches a defined Tm value. This Tm value can be defined by the user or it can be automatically selected from the maximal Tm value of the original set of probes. Average, Minimal and Maximal Tm values are calculated for the original set of probes and for the adjusted set. Deletion of nucleotides from the ends is not currently allowed. |
| | | AlnClust | |
| Methods | MainForm | Main Interface | Main Window of the AlnClust program |
| Calculate | | Library | This unit implements procedures and functions to select specific (or universal) probes from a Clustal Alignment of DNA sequences. The number of DNA sequences in the alignment is currently limited to 50. The algorithm checks the alignment column by column and from each column the potential probes are derived considering bases to both sides of the column. Selected probes from a same column are checked for similarities or differences. If the number of similarities (for finding universal probes) or differences (for specific probes) exceeds a previous defined cut-off value, the probe is selected and saved in a text file where all selected probes are contained. These probes can then be analyzed in the GPD program to refine the selection procedure using thermodynamic criteria. |

TABLE 9-continued

Description of Other Units Included in Auxiliary Applications for the GPD Program

| Pascal Unit (*.pas) | Delphi Form (*.DFM) | Type | Description |
|---|---|---|---|
| | | | Routines are also included to write the alignment, calculate consensus sequences and indicate the number of bases per column. |
| ParDlg | ParamsDlg | Dialog | Displays a dialog box showing the selection parameters. |

Build

| | | | |
|---|---|---|---|
| BuildDB | Form1 | Main interface | Main Form of the Build program |
| ListBx | SelLisDlg | Dialog | Shows a dialog box where the user can select the DNA files to be used to built a FASTA library of the sequences (A file containing multiple DNA sequences). |

Stability

| | | | |
|---|---|---|---|
| Main | MainForm | Main interface | Main window of the stability program, which displays a detailed description of the thermodynamic interactions present in the hybridization between two short sequences (less than 50 nt). |

Structure

| | | | |
|---|---|---|---|
| Main | Form1 | Main Interface | Main Window of the Structure program |
| Secondary | | Library | Stores segments of the DNA sequence that can be paired (secondary structure elements) in a linked list. |
| DNAclass | | | A variant of the TDNAclass which includes methods to calculate a simplified description of the secondary structure of a DNA molecule. The algorithm considers that the DNA sequence is placed in the X and Y axes of a coordinate system. A search is performed through diagonals on such coordinate system. Coordinates X, Y represent bases at positions X and Y respectively of the DNA sequence. If any two bases can be paired a value of "1" is assigned to the point on the coordinate system corresponding to their X and Y positions, otherwise a "0" value is assigned to such a point. The existence of consecutive values of "1" in diagonals indicates stretches of contiguous bases in the DNA sequence that can pair with each other. Such bases have a high probability to be paired in the secondary structure of the molecule. Free energy values are calculated for each section of contiguously paired bases found. The GPD software can be readily modified to check whether selected probes can hybridize with sites that have high probability of forming stable secondary structure. Such probes can have a low |

TABLE 9-continued

Description of Other Units Included in Auxiliary Applications for the GPD Program

| Pascal Unit (*.pas) | Delphi Form (*.DFM) | Type | Description |
|---|---|---|---|
| DrawDNA | | Library | probability to give a hybridization signal. Draws a colored representation of the DNA sequence and saves it as a RTF file. |
| ConfigDlg | ConfDlg | | Displays a dialog box where the search for sites with potential stable secondary structure can be configured. |
| Genbank converter | | | |
| Main | Form1 | Main Interface | Main windows of the genbank converter program |
| Analysis | | Library | Contains procedures and functions to read files in the genbank format and to convert them in files in FASTA format. This unit was the predecessor for the Formats unit in the GPD program. |
| ProbesHom Calculate | Main Form | Main interface | Main window of the ProbesHom program |
| analysis | | Library | Implementes functions and procedures to evaluate the degree of similarity between probes and multiple DNA sequences. |
| Options | OptionsDlg | Dialog | Displays a dialog box where the search of similarity can be configured. |
| MapSeq | | | |
| Codigo | | Library | Contains procedure to convert DNA sequences to numeric representations on base 10 or vice versa (a preliminary step for mapping). DNA sequences are converted in a number between 0 and $4^N - 1$, where N is the length of the sequence. Several of these routines have been already implemented in the TDNAclass and Toligoclass objects. |
| Combina2 | | Library | Calculates all possible combinations of sequences that can be derived from a sequence with ambiguous bases. |
| MiniStr | | Libray | Contains source code for building binary maps of all the probes of a given size that can be derived from a particular DNA sequence. A binary map is a table where the rows have a number between 0 and $4^N - 1$. Each row thus represents a specific sequence of length N. The table has additional columns to show the frequency of each sequence and it can include the positions where such sequence was found. Such tables are commonly referred to in computer science as Look Up tables. Tables are built in binary format such that the access to each row is very fast. |
| Tandem | | | |
| Main | MainForm | Main Interface | Main window for the Tandem program |
| Analysis | | Library | Selects capture and stacking |

TABLE 9-continued

Description of Other Units Included in Auxiliary Applications for the GPD Program

| Pascal Unit (*.pas) | Delphi Form (*.DFM) | Type | Description |
|---|---|---|---|
| | | | probes from a particular DNA sequence, for the tandem hybridization approach. Selection is base on the thermal stability of the capture probe and the free energy of the bases located at the junction of both probes. The algorithm can be readily modified to consider future more complete knowledge of the stability of tandem probes. |
| Params | ParamsDlg | Dialog | Displays a dialog box where the parameters of the selection of tandem probes can be specified. |
| | | VirtualHyb | |
| Main | MainForm | Main Interface | Main Window of the Virtual Hyb program |
| Analysis | | Library | Implements all procedures to predict hybridization pattern by means of the VH algorithm. |
| DrawDNA | | Main Interface | Displays a map of the DNA sequence of interest and the location of the hybridization probes. |

EXAMPLE 6

Screen Images of the Genosensor Probe Designer Program

The operation of the Genosensor Probe Designer program is further illustrated in FIGS. 19-25, which display screen images produced by the program's user interface.

EXAMPLE 7

Installation of Programs

To install the GPD and VH programs on a PC, setup programs are created with the help of a tool called InstallShield Express for Delphi. The InstallShield Express program first creates files called scripts, which contain all the information required by InstallShield Express to build the setup programs. The scripts for GPD and VH are listed below. To build the setup program, the files called in the script must be saved in the directories specified in the script. The script for installation of Genosensor Probe Designer program [SCRIPT.DOC] is provided in the computer program listings appendix.

EXAMPLE 8

Tutorial on Use of GPD Program

A brief tutorial is provided to exemplify the use of the GPD/VH software disclosed herein.

Case 1: Completely Automatic Design
1. Run the GPD program from the "Genosensor Probe Designer" program group, which can be located in the "Programs" menu.
2. As soon as the program starts a Welcome Box is presented. Click OK to continue.
3. The GPD user interface has several menus, a two tool bars. The left toolbar is intended to be used as Quick Reference for Design.
4. Click the "New Project" item in the tool bar or from the menu. A dialog box asking for parameters is presented. The default project's name is "untitled" you need to specify a new name y you want to conserve the results because every time that the program starts the "untitled" project is overridden. For this example we write "Case1" (spaces are not allowed in the name) as the name for this project. The Dialog box permits to specify the initial characteristics for the project. The probe source specifies the origin of the probes. In this example probes will be derived from a specific set of DNA sequences, which will be loaded into an Internal DNA database, as it will be seen soon. The application option is for now disabled, you can select any possible application and it will not have any effect in the design. A target strand must be defined. If the sequence of the probes will be derived from the direct strand (so, the probes will have the same sequence as the direct strand) target strand must be set as "Complementary". In other words, target strand is the strand against the probes will hybridize. Probe length is the length that all probes selected for the program will have. This version of the program permits only the design of probes of the same length. Oligo concentration, salt concentration and thermodynamic model are required for calculation of Enthalpy, Entropy, Free energy and Tm. Although thermodynamic model permits to be set to Empirical, this option is disabled for now. The creation of an internal DNA database must be checked in this example. The parameters in this box can be changed at any time from the "Options menu" (Or in the left tool bar) in the "Project options" item. When the project is created, its name must be appearing in the text line located in the top tool bar.
5. The next step will be to add the DNA sequences, from which probes will be derived, to the internal DNA database. By pressing the "Open DNA sequences" button in the left tool bar a open dialog box is showed and files can be loaded in this box by selecting the desired file(s) and then pressing the "open" button. This dialog permits multiple selection of probes. In order to do this task, files can be selected with the mouse while the <control> or the <shift> keys are pressed. <control> key permits the selection of non-consecutive files in the list while <shift> is used to select multiple consecutive files. The extension "dna" is suggested for DNA sequence files, however other extensions can be used. The only requirement is that files MUST be in Genbank or FASTA formats and only one sequence is permitted by file. If the format of the sequence is not recognized a message indicating that problem is showed and the sequence will not be included in the database. The files used in this example are located in the installation folder. If the path for the installation is the default, this path will be "c:\program files\GPD\examples" For this example select the files "AveI.dna", "BpuI.dna", "BspI.dna" and "PaeI.dna". After pressing the "Open button" the sequences will be read and a table, where their properties are resumed, will be showed. The property "Checked" in this table can be turned to false by typing F and then <Enter>. This property permits include or exclude DNA from specific analysis. By default, all sequences are checked.

6. After the criteria has been verified, a primary table of probes will be generated by pressing the button "generate primary table" from the left toolbar. A primary table contains all the probes that can be derived from the checked DNA sequences contained in the internal DNA database. After that the search concludes, a dialog box is showed, indicating the number of different probes that have been found.

7. If the item "Selection Criteria" from the Options menu is selected, a Dialog Box is showed with the criteria used for the selection of probes. In the default case, all the options are selected, which means that probes will be selected according with their values of composition and thermodynamic properties resumed in this dialog box. Criteria can be conveniently enabled or disabled for the user. In this example the search of convenient probes will be performed with all the criteria. Specific values used for testing these criteria can be found in the "Criteria Properties" dialog box at the Option menu. Currently values of these properties can not be modified directly in the dialog box.

8. After the criteria has been verified, a secondary table must be built. This can be accomplished by pressing the button "Generate Secondary Table" from the left tool bar. When the search is finished a window is showed containing all the selected probes and their properties. Important properties from this window are the sequence, Tm an free energy values, and the file name of the DNA sequence from which the probe was obtained. If this window is empty, this means that the selection criteria used for design were too strong. A new search can be performed, by enabling or disabling some of the criteria used.

9. Probes selected in the previous step were selected by considering the frequency of the probe in the primary table if this option was enabled in the "Selection Criteria" dialog box. However probes still are not verified for similarity degree against the DNA sequences in primary table. This step could be necessary when probes, specific for particular targets, are required. Specificity can be checked against the DNA sequences contained in the Internal DNA database or with other DNA sequences (which can be placed in a external DNA database as is described below). Current users must be careful with the parameters of the Similarity search. Parameters can be accessed in the "Similarity Search Parameters" option from the "Options menu". If probes where derived from the "direct" strand of the DNA sequences contained in the internal DNA database, (which means that they will hybridize with the complementary sequence), similarity must be checked against the direct strand of these sequences in order to obtain probes with low probability of hybridize against the "complementary" sequence of such DNA sequences. Selection is based in the minimal number of total identical bases between probes and sites inside the target DNA sequence required for rejection or a minimal length of identical and consecutive bases between probes and sites. Similarity can be checked against External DNA databases. A external DNA database is a file containing multiple DNA sequences in FASTA format.

10. External DNA databases can be created from individual DNA sequences with the utility program "Build Sequence Lib" included in the Genosensor Probe Designer programs group or any other text editor. For this example the Build Sequence Lib program must be run. Then the directory were the individual DNA sequences are located must be specified in the left list. Select: "C:\program files\GPD\examples". Use the same path for the destination of the library. Set the name of the library to "Example.txt" and the press the "Select files" button. A list of all the files with the extension "*.dna" is showed. Press the button marked with ">>" to select all the files. And then "OK". Then press the button "Build FASTA library". Close the program and check that the sequence "Example.txt" was saved in the folder.

11. In the Similarity Search Parameters dialog box in the GPD program, check the option "External Database". A Dialog box asking for the name of the file is showed. Look for the "Example.txt" file in the "c:\program files\gpd\examples" path. In this example, the DNA sequences from which probes were selected, are included in the External database, and for this reason, this option must be checked as "YES" in the dialog box. Set the values for the number of similar bases and the block size to 8 for both, and press "OK".

12. Press the button "Search Specific Probes". Unspecific probes are then removed from the secondary table and a list with 20 specific probes is showed.

13. A virtual hybridization analysis (VH) can be performed in order to evaluate the possible hybridization patterns that can be obtained by hybridizing the probes against the sequences contained in the internal DNA database. Virtual Hybridization Parameters can be modified from the "Options" menu. VH analysis evaluates the possibility that such probes can be give a "experimental" hybridization signal, even if there is no perfect match with sites in the target sequences (cross-reaction). For the configuration, user must specify the strand against the probes will hybridize (Target strand), the selection criteria (which are similar to those of the "Similarity analysis, but here, complementarity more than similarity, is evaluated). Results will be formatted here to show only sites with free energy values more stable than the first cut-off value and showing the targeted sites from 3' to 5'.

14. Once the later parameters have been specified, press the "Virtual Hybridization" button in the left tool bar. A list of the probes and potential hybridization sites is shown for each target. This list includes the sequence of the probe and the free energy of its perfect-match hybrid with its specific target. If any probe has potential to hybridize against the tested target a site or sites are shown. Sites are referenced by their position, the sequence of the target at that position (3' to 5' in this example) and the free energy value for the hybridization at this site. Free energy values more stable than the first cut-off value, but lower than the second, are showed in red. Sites more stable than the second cut-off value are showed in green. Green sites are considered as the most probable hybridization sites. Usually the sites against the probes will hybridize perfectly, must be showed in this latter color. By combining the information of these list for each sequence a Virtual Hybridization pattern is generated. Patterns must be carefully reviewed in order to see if specific patterns were found for each sequence of the internal DNA database. For the example in case 1 Table 8 is built, representing the hybridization patterns that would be expected for each selected probe against all the DNA sequences tested. It can be seen that specific patterns were found for each sequence. Numbers in red correspond to potential hybridization signals that could be found if the hybridizations conditions are not too stringent.

open windows and going to the "Files" menu to select "Close project".
2. Create a new project calling it "Case2" in the project options dialog box and set the probe source to "Manual input".
3. Open the DNA sequence "Pae2.dna" located in the "Examples" folder. The sequence data must then appear in the table of the Internal DNA database.
4. Edit the sequence by using the "Edit Sequence" option from the "Edit menu" or with a double click with the mouse at the line of data for this sequence in the table. The sequence will be showed in the editor. This editor has several useful capabilities. The DNA sequence can be modified from here by adding or deleting bases. The editor has standard tools for Cut, Copy and Paste functions but also has specific functions for searching short sequences. The "Find" option in the "Functions" menu can search short sequences which can include letters for representing

TABLE 10

Virtual Hybridization Results Obtained For The Data In Case 1

| No. | Probe | SEQ ID No. | ΔG° (perfect match) | P. aeruginosa | B. pumilus | Bacillus sp | A. veronii |
|---|---|---|---|---|---|---|---|
| 1 | AAAGGTTGG | 240 | -10.85 | | | | -10.85 |
| 2 | AAGGFIGGT | 241 | -11.29 | | | | -11.29 |
| 3 | ACTTTCAGC | 242 | -10.99 | | | | -10.99 |
| 4 | AGGAAAGGT | 243 | -10.98 | | | | -10.98 |
| 5 | AGGTTGGTA | 244 | -10.87 | | | | -10.87 |
| 6 | ATAACTGCC | 245 | -10.71 | | -7.99 | | -10.71 |
| 7 | CGAGAGTAA | 246 | -10.35 | | -10.35 | | |
| 8 | CGITCGAAA | 247 | -11.38 | | | -11.38 | |
| 9 | CTGTTTGAC | 248 | -10.36 | 10.36 | | | |
| 10 | GAAAGGTTG | 249 | -10.31 | | | | -10.31 |
| 11 | GCTGTTTGA | 250 | -11.16 | -11.16 | | | |
| 12 | GGAAAGGTT | 251 | -10.70 | | | | -10.70 |
| 13 | GTAACTGCT | 252 | -10.71 | | -10.71 | | -7.99 |
| 14 | TAACTGCCA | 253 | -11.28 | | -7.99 | | -11.28 |
| 15 | TAACTGCTC | 254 | -10.57 | | -10.57 | | -7.99 |
| 16 | TGGTAGCTA | 255 | -10.69 | | | | -10.69 |
| 17 | TGTTTGACG | 256 | -11.25 | -11.25 | -7.36 | -7.36 | |
| 18 | TTCGAAAGG | 257 | -10.89 | | | -10.89 | |
| 19 | TTGGTAGCT | 258 | -11.11 | | | | -11.11 |
| 20 | TTTCAGCGA | 259 | -11.74 | | | | -11.74 |

Case 2: Manual selection of probes.
1. Sometimes, the selection of probes cannot be made automatically because probes must be directed against specific sites of the target sequences as in the case of probes for detecting specific mutations. In such cases, the program permits the selection directly from the sequence. For this example we will create a new project after closing all the ambiguous bases. The function "Search for similarity" permits to evaluate the similarity degree of a short sequence along the DNA sequence. There is also a function to obtain the complementary strand of the entire DNA sequence. The position of the cursor on the DNA sequence in the editor is showed in the status bar at the bottom of program. In this example, with the function "Go to" from the "Functions"

menu, go to the position 35. The cursor will be placed at this site. From the "Edit" menu, select "Edit oligonucleotide" and a dialog box will be showed. The dialog box shows information about the probe at that position, such as its length, sequence, complementary strand and thermodynamic properties. A graph of internal stability is included too. The internal stability graph shows the free energy values of groups of internal 5-mers of the probe and is useful for designing PCR primers and for the selection of probes for the tandem hybridization approach (documentation in development). The position of the probe in this dialog can be modified and the changes in the parameters are immediately showed in the dialog. Press the button "Add oligo to database" at the right bottom of this dialog box. A new dialog box asking for the destination of the probes is showed in the screen. If the user wants an automated evaluation of the probes that were manually selected from the sequence, it should be convenient to send the oligo to the primary table. If not evaluation is required, it should be better to send it to the secondary table. For the purposes of this example, the oligo sequence will be sent to the secondary table. From this dialog other probes can be included in the secondary table. Add the sequences corresponding to the positions 47 and 55 too. Close the dialog and the editor.

5. Go to the "Results" menu and select "show available tables". A table containing the selected oligos will be shown with all their thermodynamic properties.

6. Go to the "Open DNA sequences" option to add more sequences to the internal DNA database for the Virtual Hybridization analysis. For this example select the sequences "Bpu2.dna" and "Ppu2.dna" and run the VH analysis. In this manual selection all the selected probes have high probability of cross-reaction with all the DNA sequences tested.

The following references were cited herein:

Allawi and SantaLucia, (1997) *Biochemistry*, 36:10581-10594.
Allawi and SantaLucia, (1998a) *Biochemistry*, 37:2170-2179.
Allawi and SantaLucia, (1998b) *Nucl. Acids Res.*, 26:2694-2701.
Allawi and SantaLucia, (1998c) *Biochemistry*, 37:9435-9444.
Beattie, (1997a) Analytical microsystems: Emerging technologies for environmental biomonitoring. In Sayler, G. S., Sanseverino, J. and Davis, K. L. (eds), *Biotechnology In The Sustainable Environment*. Plenum Press, New York, pp. 249-260.
Beattie, (1997b) Genomic fingerprinting using oligonucleotide arrays. In Caetano-Anollés, G. and Gresshoff, P. M. (eds), *DNA Markers. Protocols, Applications, and Overviews*. Wiley-Liss, New York, pp. 213-224.
Bommarito et al., (2000) *Nuc. Acids Res.*, 28:1929-1934.
Bushnell et al., (1999) *Bioinformatics*, 15:348-355.
Cantor and Schimmel, (1980) *Biophysical Chemistry, Part III: The Behavior of Biological Macromolecules*. W. H. Freeman and Company, San Francisco, pp. 1109-1265.
Doktycz et al., (1995) *J. Biol. Chem*, 270:8439-8445.
Doktycz and Beattie, (1997) Genosensors and model hybridization studies, In Beugelsdijk, T. J. (ed), *Automation Technologies for Genome Characterization*. John Wiley & Sons, New York, pp. 205-225.
Duggan et al., (1999) *Nature Genetics Supplement*, 21:10-14.
Galper et al., (1993) Knowledge-based simulation of DNA metabolism: Prediction of action and envisionment of pathways. In Hunter, L. (ed), *Artificial Intelligence and Molecular Biology*, AAAI Press, pp. 365-395.
Hacia, (1999) *Nature Genetics Supplement*, 21:42-47.
Li and Stormo, (2001) *Bioinformatics* 17:1067-1076.
Maldonado-Rodriguez and Beattie, (2001) Analysis of nucleic acids by tandem hybridization on oligonucleotide microarrays. In Rampal, J. B. (ed), *DNA Arrays. Methods and Protocols*. Humana Press, Totowa, N. J., pp.170:157-71.
Maldonado-Rodríguez et al., (1999a) *Molec. Biotechnology*, 11:1-12.
Maldonado-Rodríguez et al., (1999b) *Molec. Biotechnology*, 11:13-25.
Matzura and Wennborg, (1996) *Comp. Appl. Biosci.*12:247-249.
Owczarzy et al., (1997) *Biopolymers*, 44:217-239.
Peyret et al., (1999) *Biochemistry*, 38:3468-3477.
Pozhitkov and Tautz (2002) *BMC Bioinformatics* 3:9.
Reyes-Lopez et al., (2003) *Nucl. Acids Res.*, 31:779-789.
Rychlik, (1993) Selection of primers for polymerase chain reaction. In White, B. A. (ed), *PCR Protocols: Current Methods and Applications*. Humana Press, Totowa, N. J., pp. 31-40.
SantaLucia, (1998) *Proc. Natl. Acad. Sci., USA*, 95:1460-1465.
Schütz and von Ahsen, (1999) *BioTechniques*, 27:1218-1224.
Southern et al., (1999) *Nature Genetics Supplement*, 21:5-9.
Thompson et al., (1997) *Nucl. Acids Res.*, 24:4876-4882.
Vahrson et al., (1996) *Comput. Appl. Biosci.*, 12:119-127.
Yang et al., (1997) *Anal. Chim. Acta*, 346:259-275.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method for designing and selecting oligonucleotide probes for use in DNA microarrays, using a computer program product-having program instructions executable on a computer, comprising the steps:

(a) inputting target DNA sequences;

(b) creating an internal DNA database table that includes the entire target DNA sequences from which oligonucleotide probes are selected;

(c) generating a primary table of oligonucleotide probes that contains all possible probes of a defined length that can be derived from said internal DNA database table;

(d) applying user-defined selection criteria to the probes contained in said primary table of oligonucleotide probes to generate a secondary table of oligonucleotide probes therefrom, said user-defined selection criteria including compositional and thermodynamic properties;

(e) evaluating the sequence similarity between probes of said secondary table and said inputted target DNA sequences, to generate a table of oligonucleotide probes of optimized sequence specificity; and (f) performing virtual hybridization of said oligonucleotide probes of optimized sequence specificity against said inputted target DNA sequences, wherein a nearest-neighbor predicted thermodynamic model of duplex formation is used to identify the sites of hybridization of said oligonucleotides within the target DNA sequences, including sites of perfectly matched hybrids as well as stably mismatched hybrids sequences, comprising;

(i) selecting a minimal value (minbasescom) for the number of complementary bases between probes and potential hybridization sites, wherein said minbasescom is defined as 2≦minbasescom≦L (a given probe length);

(ii) selecting a minimal value (minblocksize) for the length of contiguously paired bases within potential hybridization sites, wherein said minblocksize is specified as 2≦minblocksize≦L (a given probe length);

(iii) selecting potential hybridization sites by evaluating the complementarity degree between said oligonucleotide probes and potential hybridization sites along the target sequences, wherein said potential hybridization sites are defined as sites where the number of complementary bases between the probe and the evaluated sites is equal to or greater than minbasescom or sites where a block of contiguously paired bases is equal to or greater than minblocksize;

(iv) calculating the free energy value ($\Delta G°$) for the duplex stability of probes paired with their respective potential hybridization sites using said nearest-neighbor thermodynamic model of duplex formation; and (v) selecting sites of high hybridization probability, wherein said sites of high hybridization probability are potential hybridization sites corresponding to probe-target duplexes with ($\Delta G°$) values equal to or lower than pre-determined $\Delta G°$ cutoff values; and (g) showing to the user sequences for oligonucleotide probes selected by the virtual hybridization of step (f), wherein the selected oligonucleotide probes are designed to hybridize to the target DNAs in DNA microarrays.

2. The method of claim 1, wherein said target DNA sequences are selected from the group consisting of single DNA sequence, multiple DNA sequences, DNA sequence database, oligonucleotide sequences and oligonucleotide database.

3. The method of claim 1, wherein said user-defined selection criteria comprise criteria for rejecting or accepting oligonucleotide probes based upon [A+T] composition, [G+C] composition, melting temperature (Tm) range, enthalpy, entropy, free energy, internal repeated sequences, sequence symmetry of probes, or frequency of occurrence.

4. The method of claim 1, wherein said software program comprises program instructions for selecting oligonucleotide probes according to a program application selected from the group consisting of simple selection application, mapping application, non-aligned sequences application, aligned sequences application and tandem hybridization application.

5. The method of claim 1, wherein applying user-defined selection criteria of step (d) comprises adding or deleting nucleotides from one or both ends of oligonucleotide probes of said primary table.

6. The method of claim 1, wherein in said primary table comprises one or more probes with DNA sequences complementary to sequences comprising said inputted target DNA.

7. A method for designing and selecting optimized sets of oligonucleotide probes for use in DNA microarrays, using a computer program product having program instructions executable on a computer, for designing and selecting oligonucleotide probes comprising the steps of:

(a) inputting target DNA sequences;

(b) creating an internal DNA database table that includes the entire target DNA sequences from which oligonucleotide probes are selected;

(c) generating a primary table of oligonucleotides that contains all possible probes of a defined length that can be derived from said internal DNA database table;

(d) applying user-defined selection criteria to the probes contained in said primary table of oligonucleotide probes to generate a secondary table of oligonucleotide probes therefrom, said user-defined selection criteria including compositional and thermodynamic properties;

(e) performing virtual hybridization to predict the hybridization pattern of probes contained in said secondary table with said inputted target DNA sequences, comprising;

(i) selecting a minimal value (minbasescom) for the number of complementary bases between probes and potential hybridization sites, wherein said minbasescom is defined as 2≦minbasescom≦L (a given probe length);

(ii) selecting a minimal value (minblocksize) for the length of contiguously paired bases within potential hybridization sites, wherein said minblocksize is specified as 2≦minblocksize≦L (a given probe length);

(iii) selecting potential hybridization sites by evaluating the complementarity degree between said oligonucleotide probes and potential hybridization sites along the target sequences, wherein said potential hybridization sites are defined as sites where the number of complementary bases between the probe and the evaluated sites is equal to or greater than minbasescom or sites where a block of contiguously paired bases is equal to or greater than minblocksize;

(iv) calculating the free energy value ($\Delta G°$) for the duplex stability of probes paired with their respective potential hybridization sites using said nearest-neighbor thermodynamic model of duplex formation; and (v) selecting sites of high hybridization probability, wherein said sites of high hybridization probability are potential hybridization sites corresponding to probe-target duplexes with ($\Delta G°$) values equal to or lower than pre-determined $\Delta G°$ cutoff values;

(f) eliminating probes which have the potential for ambiguous hybridization; and (g) showing to the user optimized sets of sequences for oligonucleotide probes selected by the virtual hybridization of step (f), wherein the selected oligonucleotide probes are designed to hybridize to the target DNAs in DNA microarrays.

8. The method of claim 7, wherein said primary table comprises one or more probes with DNA sequences complementary to sequences comprising said inputted target DNA.

* * * * *

SEQUENCE LISTING

<160> NUMBER OF SEQ ID NOS: 23

<210> SEQ ID NO 1
<211> LENGTH: 17
<212> TYPE: DNA
<213> ORGANISM: Artificial Sequence
<220> FEATURE:
<223> OTHER INFORMATION: a hypothetical sequence

<400> SEQUENCE: 1

```
tatagtagaa accacaa                                                   17

<210> SEQ ID NO 2
<211> LENGTH: 19
<212> TYPE: DNA
<213> ORGANISM: Artificial Sequence
<220> FEATURE:
<221> NAME/KEY: primer_bind
<223> OTHER INFORMATION: forward primer for region A near the 5'
      end of the microbial 16S rRNA gene

<400> SEQUENCE: 2
ctcctacggg aggcagcag                                                 19

<210> SEQ ID NO 3
<211> LENGTH: 19
<212> TYPE: DNA
<213> ORGANISM: Artificial Sequence
<220> FEATURE:
<221> NAME/KEY: primer_bind
<223> OTHER INFORMATION: reverse primer for region A near the 5'
      end of the microbial 16S rRNA gene

<400> SEQUENCE: 3
gtattaccgc ggctgctgg                                                 19

<210> SEQ ID NO 4
<211> LENGTH: 19
<212> TYPE: DNA
<213> ORGANISM: Artificial Sequence
<220> FEATURE:
<221> NAME/KEY: primer_bind
<223> OTHER INFORMATION: forward primer for region B near the 5'
      end of the microbial 16S rRNA gene

<400> SEQUENCE: 4
ccagcagccg cggtaatac                                                 19

<210> SEQ ID NO 5
<211> LENGTH: 21
<212> TYPE: DNA
<213> ORGANISM: Artificial Sequence
<220> FEATURE:
<221> NAME/KEY: primer_bind
<223> OTHER INFORMATION: reverse primer for region B near the 5'
      end of the microbial 16S rRNA gene

<400> SEQUENCE: 5
ggcgtggact accagggtat c                                              21

<210> SEQ ID NO 6
<211> LENGTH: 197
<212> TYPE: DNA
<213> ORGANISM: P. aeruginosa
<220> FEATURE:
<221> NAME/KEY: gene
<223> OTHER INFORMATION: region A near the 5' end of the
      16S rRNA gene

<400> SEQUENCE: 6
ctcctacggg aggcagcagt ggggaatatt ggacaatggg cgcaagcctg              50
atccagccat gccgcgtgtg tgaagaaggt cttcggattg taaagcactt             100
taagttggga ggaagggcag taagttaata ccttgctgtt tgacgttacc             150
aacagaataa gcaccggcta acttcgtgcc agcagccgcg gtaatac                197
```

```
<210> SEQ ID NO 7
<211> LENGTH: 198
<212> TYPE: DNA
<213> ORGANISM: P. alcaligenes
<220> FEATURE:
<221> NAME/KEY: gene
<223> OTHER INFORMATION: region A near the 5' end of the
      16S rRNA gene

<400> SEQUENCE: 7
ctcctacggg aggcagcagt ggggaatatt ggacaatggg cgaaagcctg          50
atccagccat gccgcgtgtg tgaagaaggt cttcggattg taaagcactt         100
taagttggga ggaagggcag taagttaata ccttgctgtt ttgacgttac         150
caacagaata agcaccggct aactctgtgc cagcagccgc ggtaatac           198

<210> SEQ ID NO 8
<211> LENGTH: 198
<212> TYPE: DNA
<213> ORGANISM: P. fluorescens
<220> FEATURE:
<221> NAME/KEY: gene
<222> LOCATION: n = a, c, t, or g at positions 2, 10, 11,
      and 15; m = a or c at position 103
<223> OTHER INFORMATION: region A near the 5' end of the
      16S rRNA gene

<400> SEQUENCE: 8
cncctacggn nggcngcagt ggggaatatt ggacaatggg cgaaagcctg          50
atccagccat gccgcgtgtg tgaagaaggt cttcggattg taaagcactt         100
tamgttggga ggaagggcat taacctaata cgttagtgtt tcgacgttac         150
cgacagaata agcaccggct aactctgtgc cagcagccgc ggtaatac           198

<210> SEQ ID NO 9
<211> LENGTH: 198
<212> TYPE: DNA
<213> ORGANISM: P. putida
<220> FEATURE:
<221> NAME/KEY: gene
<223> OTHER INFORMATION: region A near the 5' end of the
      16S rRNA gene

<400> SEQUENCE: 9
ctcctacggg aggcagcagt ggggaatatt ggacaatggg cgaaagcctg          50
atccagccat gccgcgtgtg ttaagaaggt cttcggattg taaagcactt         100
taagttggga ggaagggcat taacctaata cgttagtgtt ttcacgttac         150
cgacagaata agcaccggct aactctgtgc cagcagccgc ggtaatac           198

<210> SEQ ID NO 10
<211> LENGTH: 198
<212> TYPE: DNA
<213> ORGANISM: P. veronii
<220> FEATURE:
<221> NAME/KEY: gene
<223> OTHER INFORMATION: region A near the 5' end of the
      16S rRNA gene

<400> SEQUENCE: 10
ctcctacggg aggcagcagt ggggaatatt ggacaatggg cgaaagcctg          50
atccagccat gccgcgtgtg tgaagaaggt cttcggattg taaagcactt         100
taagttggga ggaagggcag ttacctaata cgtgattgtt ttgacgttac         150
```

-continued

```
cgacagaata agcaccggct aactctgtgc cagcagccgc ggtaatac        198
```

```
<210> SEQ ID NO 11
<211> LENGTH: 198
<212> TYPE: DNA
<213> ORGANISM: P. syringae
<220> FEATURE:
<221> NAME/KEY: gene
<223> OTHER INFORMATION: region A near the 5' end of the
      16S rRNA gene

<400> SEQUENCE: 11
```

```
ctcctacggg aggcagcagt ggggaatatt ggacaatggg cgaaagcctg        50
atccagccat gccgcgtgtg tgaagaaggt cttcggattg taaagcactt       100
taagttggga ggaagggcag ttacctaata cgtgattgtt ttgacgttac       150
cgacagaata agcaccggct aactctgtgc cagcagccgc ggtaatac        198
```

```
<210> SEQ ID NO 12
<211> LENGTH: 197
<212> TYPE: DNA
<213> ORGANISM: S. maltophilia
<220> FEATURE:
<221> NAME/KEY: gene
<223> OTHER INFORMATION: region A near the 5' end of the
      16S rRNA gene

<400> SEQUENCE: 12
```

```
ctcctacggg aggcagcagt ggggaatatt ggacaatggg cgcaagcctg        50
atccagccat accgcgtggg tggagaagcc ttcgggttgt aaagcccttt       100
tgttgggaaa gaaatccagc tggttaatac ccggttggga tgacggtacc       150
caaagaataa gcaccggcta acttcgtgcc agcagccgcg gtaatac        197
```

```
<210> SEQ ID NO 13
<211> LENGTH: 198
<212> TYPE: DNA
<213> ORGANISM: B. pumilus
<220> FEATURE:
<221> NAME/KEY: gene
<223> OTHER INFORMATION: region A near the 5' end of the
      16S rRNA gene

<400> SEQUENCE: 13
```

```
ctcctacggg aggcagcagt agggaatctt ccgcaatgga cgaaagtctg        50
acggagcaac gccgcgtgag tgatgaaggt tttcggatcg taaagctctg       100
ttgttaggga agaacaagtg cgagagtaac tgctcgcacc ttgacggtac       150
ctaaccagaa agccacggct aactacgtgc cagcagccgc ggtaatac        198
```

```
<210> SEQ ID NO 14
<211> LENGTH: 198
<212> TYPE: DNA
<213> ORGANISM: Bacillus
<220> FEATURE:
<221> NAME/KEY: gene
<223> OTHER INFORMATION: region A near the 5' end of the
      16S rRNA gene

<400> SEQUENCE: 14
```

```
ctcctacggg aggcagcagt agggaatctt ccgcaatgga cgaaagtctg        50
acggagcaac gccgcgtgag tgatgaaggt tttcggatcg taaaactctg       100
ttgttaggga agaacaagtg ccgttcgaaa gggcggcacc ttgacggtac       150
```

```
ctaacgagaa agccacggct aactacgtgc cagcagccgc ggtaatac          198

<210> SEQ ID NO 15
<211> LENGTH: 294
<212> TYPE: DNA
<213> ORGANISM: P. fluorescens
<220> FEATURE:
<221> NAME/KEY: gene
<223> OTHER INFORMATION: region B near the 5' end of the
      16S rRNA gene

<400> SEQUENCE: 15
ccagcagccg cggtaataca gagggtgcaa gcgttaatcg gaattactgg           50
gcgtaaagcg cgcgtaggtg gtttgttaag ttggatgtga atccccggg           100 ctcaacctgg gaactgcatc caaaactgac tgactagagt atggtagagg          150
gtggtggaat ttcctgtgta gyggtgaaat gcgttgatat aggaaggaac          200
accagtggtg aaggcgacca cctggactaa tactgacact gaggtgcgaa          250
agcgtgggga gcaaacagga ttagataccc tggtagtcca cgcc               294

<210> SEQ ID NO 16
<211> LENGTH: 294
<212> TYPE: DNA
<213> ORGANISM: P. veronii
<220> FEATURE:
<221> NAME/KEY: gene
<223> OTHER INFORMATION: region B near the 5' end of the
      16S rRNA gene

<400> SEQUENCE: 16
ccagcagccg cggtaataca gagggtgcaa gcgttaatcg gaattactgg           50
gcgtaaagcg cgcgtaggtg gttagttaag ttggatgtga atccccggg           100 ctcaacctgg gaactgcatt caaaactgac tgactagagt atggtagagg          150
gtggtggaat ttcctgtgta gcggtgaaat gcgtagatat aggaaggaac          200
accagtggcg aaggcgacca cctggactga tactgacact gaggtgcgaa          250
agcgtgggga gcaaacagga ttagataccc tggtagtcca cgcc               294

<210> SEQ ID NO 17
<211> LENGTH: 294
<212> TYPE: DNA
<213> ORGANISM: P. syringae
<220> FEATURE:
<221> NAME/KEY: gene
<223> OTHER INFORMATION: region B near the 5' end of the
      16S rRNA gene

<400> SEQUENCE: 17
ccagcagccg cggtaataca gagggtgcaa gcgttaatcg gaattactgg           50
gcgtaaagcg cgcgtaggtg gtttgttaag ttggatgtga atccccggg           100 ctcaacctgg gaactgcatc caaaactggc aagctagagt atggtagagg          150
gtggtggaat ttcctgtgta gcggtgaaat gcgtagatat aggaaggaac          200
accagtggcg aaggcgacca cctggactga tactgacact gaggtgcgaa          250
agcgtgggga gcaaacagga ttagataccc tggtagtcca cgcc               294

<210> SEQ ID NO 18
<211> LENGTH: 294
<212> TYPE: DNA
```

<210> SEQ ID NO 18
<211> LENGTH: 294
<212> TYPE: DNA
<213> ORGANISM: P. putida
<220> FEATURE:
<221> NAME/KEY: gene
<223> OTHER INFORMATION: region B near the 5' end of the
    16S rRNA gene

<400> SEQUENCE: 18
ccagcagccg cggtaataca gagggtgcaa gcgttaatcg gaattactgg         50
gcgtaaagcg cgcgtgggtg gtttgttaag ttggatgtga aagccccggg        100
ctcaacctgg gaactgcatc caaaactggc aagctagagt acggtagagg        150
gtggtggaat ttcctgtgta gcggtgaaat gcgtagatat aggaaggaac        200
accagtggcg aaagcgacca cctggactga tactgacact gaggtgcgaa        250
agcgtgggga gcaaacagga ttagataccc tggtagtcca cgcc              294

<210> SEQ ID NO 19
<211> LENGTH: 293
<212> TYPE: DNA
<213> ORGANISM: P. aeruginosa
<220> FEATURE:
<221> NAME/KEY: gene
<223> OTHER INFORMATION: region B near the 5' end of the
    16S rRNA gene

<400> SEQUENCE: 19
ccagcagccg cggtaatacg aagggtgcaa gcgttaatcg gaattactgg         50
gcgtaaagcg cgcgtaagtg gttcagcaag cttgatgtga atccccggg         100 ctcaacctgg gaactgcatc caaaagctac tgagctagag tacggtagag        150
gtggtagaat ttcctgtgta gcggtgaaat gcgtagatat aggaaggaac        200
accagtggcg aaggcgacca cctggactgt actgacactg aggtgcgaaa        250
gcgtggggag caaacaggat tagataccct ggtagtccac gcc               293

<210> SEQ ID NO 20
<211> LENGTH: 294
<212> TYPE: DNA
<213> ORGANISM: P. alcaligenes
<220> FEATURE:
<221> NAME/KEY: gene
<223> OTHER INFORMATION: region B near the 5' end of the
    16S rRNA gene

<400> SEQUENCE: 20
ccagcagccg cggtaataca gagggtgcaa gcgttaatcg gaattactgg         50
gcgtaaagcg cgcgtaggtg gttcagcaag ttggaggtga atccccggg         100 ctcaacctgg gaactgcctc caaaactact gagctagagt acggtagagg        150
gtagtggaat ttcctgtgta gcggtgaaat gcgtagatat aggaaggaac        200
accagtggcg aaggcgacta cctggactga tactgacact gaggtgcgaa        250
agcgtgggga gcaaacagga ttagataccc tggtagtcca cgcc              294

<210> SEQ ID NO 21
<211> LENGTH: 294
<212> TYPE: DNA
<213> ORGANISM: S. maltophilia
<220> FEATURE:
<221> NAME/KEY: gene
<223> OTHER INFORMATION: region B near the 5' end of the
    16S rRNA gene

<400> SEQUENCE: 21

```
                                    -continued ccagcagccg cggtaatacg aagggtgcaa gcgttactcg gaattactgg              50
gcgtaaagcg tgcgtaggtg gttatttaag tccgttgtga aagccctggg             100
ctcaacctgg gaactgcagt ggatactgga tgactagaat gtggtagagg             150
gtagcggaat tcctggtgta gcagtgaaat gcgtagagat caggaggaac             200
atccatggcg aaggcagcta cctggaccaa cattgacact gaggcacgaa             250
agcgtgggga gcaaacagga ttagataccc tggtagtcca cgcc                   294

<210> SEQ ID NO 22
<211> LENGTH: 294
<212> TYPE: DNA
<213> ORGANISM: B. pumilus
<220> FEATURE:
<221> NAME/KEY: gene
<223> OTHER INFORMATION: region B near the 5' end of the
      16S rRNA gene

<400> SEQUENCE: 22
ccagcagccg cggtaatacg taggtggcaa gcgttgtccg gaattattgg              50
gcgtaaaggg ctcgcaggcg gtttcttaag tctgatgtga aagcccccgg             100
ctcaaccggg gagggtcatt ggaaactggg aaacttgagt gcagaagagg             150
agagtggaat tccacgtgta gcggtgaaat gcgtagagat gtggaggaac             200
accagtggcg aaggcgactc tctggtctgt aactgacgct gaggagcgaa             250
agcgtgggga gcaaacagga ttagataccc tggtagtcca cgcc                   294

<210> SEQ ID NO 23
<211> LENGTH: 294
<212> TYPE: DNA
<213> ORGANISM: Bacillus
<220> FEATURE:
<221> NAME/KEY: gene
<223> OTHER INFORMATION: region B near the 5' end of the
      16S rRNA gene

<400> SEQUENCE: 23
ccagcagccg cggtaatacg taggtggcaa gcgttgtccg gaattattgg              50
gcgtaaagcg cgcgcaggcg gtctcttaag tctgatgtga aagcccccgg             100
ctcaaccggg gagggtcatt ggaaactggg agacttgagt acagaagagg             150
agagtggaat tccacgtgta gcggtgaaat gcgtagagat gtggaggaac             200
accagtggcg aaggcgactc tctggtctgt aactgacgct gaggcgcgaa             250
agcgtgggga gcaaacagga ttagataccc tggtagtcca cgcc                   294
```